US007071340B2

(12) United States Patent
Balme et al.

(10) Patent No.: US 7,071,340 B2
(45) Date of Patent: Jul. 4, 2006

(54) FUNGICIDAL 1-BENZOXEPIN DERIVATIVES

(75) Inventors: Genevieve Balme, Miribel (FR); Isabelle Coudanne, Paris (FR); Philippe Desbordes, Lyons (FR); Nathalie Huser, Lyons (FR); Philippe Lemaire, Lyons (FR); Adeline Mousques, Lyons (FR); Alex Nivlet, Carlisle (GB); Jean-Pierre Vors, Lyons (FR)

(73) Assignee: Bayer Cropscience S.A. (FR)

( * ) Notice: Subject to any disclaimer, the term of this patent is extended or adjusted under 35 U.S.C. 154(b) by 0 days.

(21) Appl. No.: 10/486,128

(22) PCT Filed: Aug. 8, 2002

(86) PCT No.: PCT/FR02/02826

§ 371 (c)(1),
(2), (4) Date: Jul. 20, 2004

(87) PCT Pub. No.: WO03/014104

PCT Pub. Date: Feb. 20, 2003

(65) Prior Publication Data

US 2004/0249173 A1 Dec. 9, 2004

(30) Foreign Application Priority Data

Aug. 8, 2001 (FR) .................................. 01 10575

(51) Int. Cl.
*C07D 313/08* (2006.01)
(52) U.S. Cl. ..................................................... 549/355
(58) Field of Classification Search ................. 549/355
See application file for complete search history.

(56) References Cited

U.S. PATENT DOCUMENTS 3,517,031 A * 6/1970 Beereboo et al. ........... 260/333

OTHER PUBLICATIONS

Lachapelle et al, Can. J. Chem., vol., 65, pp. 2575-2594, 1987.*
Chemical Abstracts, vol. 115, No. 23, 1991, Columbus, OH, US; abstract No. 25597f, Biswas, S.: "Intramolecular Acylation", p. 844, col. 1; XP002194766, abstract & Synth. Commun., vol. 21, No. 18-19, 1991, pp. 1865-1874, Engl.
J.B.P.A. Wynberg: Novel Monochlorinated Metabolites With a 1-Benzoxepin Skeleton, Tetrahedron Letters, vol. 40, No. 31, 1999, pp. 5767-5770, XP004171562, Elsevier Science Publishers, Amsterdam., NL, ISSN: 0040-4039, pp. 5767-5769 (cited in the application).
P. Kahnberg: "Synthesis of the Antifungal 1-Benzoxepin Pterulone", Tetrahedron, vol. 57, No. 33, 2001, pp. 7181-7184, XP004298068, Elsevier Science Publishers, Amsterdam, NL, ISSN:0040-4020, pp. 7181-7184 (cited in the appplication).
Michaela Engler et al., "Pterulinic Acid and Pterulone, Two Novel Inhibitors of NADH: Ubiquinone Oxidoreductase (Complex I) Produced by a *Pterula* Species", The Journal of Antibiotics, vol. 50, No. 4, pp. 325-333 (Apr. 1997).
Joannes B.P.A. Winjberg, et al., "Novel monochlorinated metabolites with a 1-benzoxepin skeleton from *Mycena galopus*", Tetrahedron Letters 40 (1999) 5767-5770.
Michaela Engler et al., "Production of Antibiotics by *Collybia nivalis, Omphalotus olearius*, a *Favolaschia* and a *Pterula* Species on Natural Substrates", Z. Naturforsch. 53c, 318-324 (1998).
Frank Eilbert et al., "Effects of Antifungal Compounds on Conidial Germination and on the Induction of Appressorium Formation of *Magnaporthe griesea*", Z. Naturforsch 54c, 903-908 (1999).
Pia Kahnberg, et al., "Synthesis of the antifungal 1-benzoxepin pterulone" Tetrahedron Letters 57 (2001) 7181-7184.
Sheng-Tung Huang et al., "Total synthesis of NADH:ubiquinone oxidoreductase (complex I) antagonist pterulone and its analogue", Tetrahedron Letters 42 (2001) 7473-7475.
Bas W.T. Gruijters et al., "Total Synthesis and Bioactivity of Some Naturally Occurring Pterulones", *J. Nat. Prod.*, 2002, 65, pp. 558-561.

* cited by examiner

*Primary Examiner*—Celia Chang
(74) *Attorney, Agent, or Firm*—Ostrolenk, Farber, Gerb & Soffen, LLP

(57) ABSTRACT

The invention concerns novel 1-benzoxepin derivatives, methods for preparing them, their use as fungicides, in particular in the form of fungicidal compositions, as well as methods for controlling phytopathogenic fungi of crops using said compounds or said compositions.

26 Claims, No Drawings

FUNGICIDAL 1-BENZOXEPIN DERIVATIVES

CROSS REFERENCE TO RELATED APPLICATIONS

The present application is a 35 U.S.C. Section 371 national phase conversion of PCT/FR02/02826, filed Aug. 8, 2002, which claims priority of French Application No. 01/10575 filed Aug. 8, 2001.

FIELD OF THE INVENTION

The present invention relates to novel 1-benzoxepin derivatives, to their processes of preparation, to their use as fungicides, in particular in the form of fungicidal compositions, and to the processes for controlling phytopathogenic fungi on crops using these compounds or these compositions.

STATE OF THE ART

Compounds with a 1-benzoxepin structure have already been described in the literature. Thus, the studies by M. Engler et al. (*The Journal of Antibiotics*, 50(4), (1997), 325–329 and 330–33 and *Zeitschrift fuer Naturforschung, C: Biosciences*, 53(5/6), (1998), 318–324) present three compounds in particular, pterulone A, pterulone B and pterulinic acid, comprising a benzoxepin backbone, obtained from fermentation liquors:

pterulone A

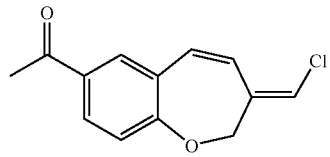

pterulone B

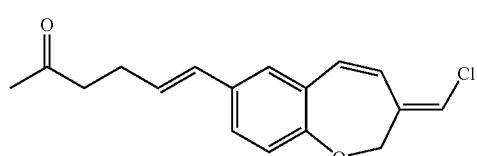

pterulinic acid

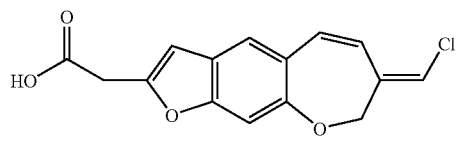

Likewise, J. Wijnberg et al. (*Tetrahedron Letters*, 40, (1999), 5767–5770) also present two compounds with structures related to pterulone A, 6-hydroxypterulone A and the hydroxymethyl analog, also obtained from fermentation liquors:

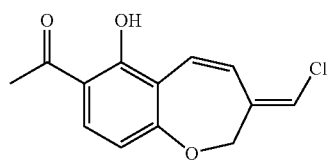

-continued

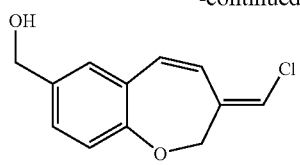

These publications, and the studies by F. Eilbert et al. (*Zeitschrift fuer Naturforschung, C: Biosciences*, 54(11), 903–908) mention an antifungal activity for these compounds: in vitro tests indeed make it possible to demonstrate some active effects with regard to certain phytopathogenic fungi. However, none of these publications gives an indication of solutions which allow the fungicidal activity of these compounds to be increased. In addition, these disclosures give no means (apart from extraction from natural products) of access by the chemical route to these compounds or to their homologs.

The recent studies by P. Kahnberg et al. (*Tetrahedron*, 57, (2001), 7181–7184) and then by S-T. Huang et al. (*Tetrahedron Letters*, 42, (2001), 7473–7475) and by B. Gruijters et al. (*Journal of Natural Products*, 65, (2002), 558–561) describe several routes for the chemical synthesis of pterulone A or of its hydroxymethyl analog from 1-benzoxepin-3-one or from a phenol which is suitably substituted. However, no synthetic route for pterulone derivatives is described. Furthermore, no indication appears in these publications with regard to novel antifungal activities of non-natural pterulone derivatives.

Compounds with the 3,4-dihydro-[(2H)-benzoxepin-3-one structure have also already been described in the literature. Thus, J. Berrebomm et al. (U.S. Pat. No. 3,799,892 (1974), U.S. Pat. No. 3,647,479 (1972) and U.S. Pat. No. 3,517,031 (1970)) claim odoriferous activities for these compounds.

In the field of combating phytopathogenic fungi on plants, there is a constant search for new families of fungicidal compounds. This is because the compounds which are known and already commercially available often exhibit many disadvantages, such as, for example, low activity, compounds effective with regard to a relatively small range of fungal diseases, low selectivity, toxicity, indeed even ecotoxicity, or problems of resistance. It is the same for the natural products, which, although exhibiting an antifungal activity, are not sufficiently active to be able to be marketed, in particular in the field of agriculture.

In other words, the known fungicidal compounds are not always sufficiently active and/or have a relatively narrow spectrum of activity. In order to eradicate all the various species of fungi which attack plants, the user must, for example, use several products, the spectrum and the application doses of which have to be precisely known. In addition, the use of several products conflicts with the methods for treating crops recommended today, where the application doses have to be as low as possible with the obvious aim of protecting the environment.

Furthermore, the use of large amounts of fungicidal products and/or of several different fungicidal products is very often very harmful to the crops (toxicity of the products). The use of large amounts of products in the treatment of fungal diseases leads in some cases to the appearance of fungal strains which are resistant to these products. This is the reason why it is always necessary to provide the user with novel antifungal molecules.

One object of the present invention is to provide a novel family of compounds having a broad spectrum of action with regard to phytopathogenic fungi on crops.

Another object of the present invention is to provide a novel family of compounds having a broad spectrum of action with regard to phytopathogenic fungi on crops which makes it possible to solve the specific problems encountered.

Another object of the present invention is to provide a novel family of compounds having an improved broad spectrum of action with regard to phytopathogenic fungi on crops and having a reduced toxicity and/or ecotoxicity.

Another object of the present invention is to provide a novel family of compounds having an improved broad spectrum of action with regard to phytopathogenic fungi on crops such as cereals, rice, corn, sunflower, fruit trees, fruit, forest trees, the vine, oleaginous crops, truck farming crops, vegetable crops, protein-yielding crops, members of the Solanaceae family, beetroot, and the like.

Another object of the present invention is to provide a synthetic route for access to this novel family of compounds, which are active at low doses, having an improved broad spectrum of action with regard to phytopathogenic fungi on crops.

DEFINITION OF THE INVENTION

In an entirely surprising way, it has been found that these objects can be achieved, in all or in part, by compounds comprising a 1-benzoxepin unit with the general structure and the process of synthesis defined below.

Thus, the present invention relates first of all to the compounds of general formula (Ia) or (Ib):

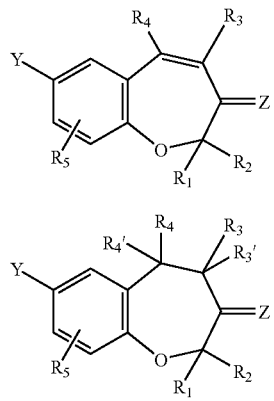

in which:
  Y is chosen from hydrogen, a halogen atom chosen from fluorine, chlorine, bromine and iodine, the formyl radical, the carboxyl radical, an alkoxy radical, the linear or branched alkyl part comprising from 1 to 6 carbon atoms, a cycloalkoxy radical, the cycloalkyl part comprising from 3 to 7 carbon atoms, a hydroxyalkyl radical, the linear or branched alkyl part comprising from 1 to 6 carbon atoms, the nitro radical, an alkylcarbonyl radical, the linear or branched alkyl part comprising from 1 to 6 carbon atoms, a cycloalkylcarbonyl radical, the cycloalkyl part comprising from 3 to 7 carbon atoms, an alkoxycarbonyl radical, the linear or branched alkyl part comprising from 1 to 6 carbon atoms, a cycloalkoxycarbonyl radical, the cycloalkyl part comprising from 3 to 7 carbon atoms, a heterocyclyl-oxycarbonyl radical, an alkylcarbonyloxy radical, the linear or branched alkyl part comprising from 1 to 6 carbon atoms, a cycloalkylcarbonyloxy radical, the cycloalkyl part comprising from 3 to 7 carbon atoms, an —$SR_1$, —$SOR_1$, —$SO_2R_1$, —$C(O)NR_1R_6$, —$C(O)NR_1(OR_2)$, —$C(O)NR_1(NR_2R_6)$, —$C(S)NR_1R_6$, —$NR_1C(O)NR_2R_6$, —$NR_1C(S)NR_2R_6$, —$OC(O)NR_1R_6$, —$NR_1R_6$, —$NR_1(OR_2)$, —$C(R_1)=NR_6$, —$C(R_1)=NR_6(OR_2)$, —$C(R_1)=NR_6(NR_2R_6)$ or —$N=NR_1R_6$ radical, a linear or branched alkyl radical comprising from 1 to 20 carbon atoms, a linear or branched alkenyl radical comprising from 1 to 20 carbon atoms, a cycloalkyl radical comprising from 3 to 7 carbon atoms, an aryl, aryloxy, heteroaryl, heteroaryloxy, arylalkyl, arylalkyloxy, heteroarylalkyl, heteroarylalkyloxy, arylcarbonyl, heteroarylcarbonyl, arylcarbonyloxy or heteroarylcarbonyloxy radical, the hydroxyl radical and the cyano radical;

Z is a divalent radical chosen from =O, =$CR_1X$, =CXX', =$CR_1(CN)$, =$CR_1R_2$, =$CR_1(OR_2)$, =$CR_1$—$C(O)R_2$, =$CR_1$—$C(O)OR_2$, =$CR_1(SR_2)$, =$CR_1(NR_2R_6)$, =$NR_1$, =$N(OR_1)$ or =$N(NR_1R_6)$;

X and X' are identical or different and are chosen from fluorine, chlorine, bromine and iodine;

$R_1$, $R_2$, $R_3$, $R_3$', $R_4$ and $R_4$' are identical or different and are chosen from hydrogen, a linear or branched alkyl radical comprising from 1 to 20 carbon atoms, a cycloalkyl radical comprising from 3 to 7 carbon atoms, an aryl radical, an arylalkyl radical, a heteroaryl radical and a heteroarylalkyl radical;

the two substituents $R_1$ and $R_2$ can together form a saturated or unsaturated ring or heterocycle comprising 3 to 8 atoms;

the two substituents $R_3$ and $R_4$ can together form a saturated or unsaturated ring or heterocycle comprising 3 to 8 atoms;

$R_5$ is chosen from the hydrogen atom, the hydroxyl radical, a linear or branched alkyl radical comprising from 1 to 6 carbon atoms, a halogen atom chosen from fluorine, chlorine, bromine and iodine, the formyl radical, the carboxyl radical, an alkoxy radical, the linear or branched alkyl part comprising from 1 to 6 carbon atoms, a cycloalkoxy radical, the cycloalkyl part comprising from 3 to 7 carbon atoms, the nitro radical, an alkylcarbonyl radical, the linear or branched alkyl part comprising from 1 to 6 carbon atoms, a cycloalkylcarbonyl radical, the cycloalkyl part comprising from 3 to 7 carbon atoms, an alkoxycarbonyl radical, the linear or branched alkyl part comprising from 1 to 6 carbon atoms, a cycloalkoxycarbonyl radical, the cycloalkyl part comprising from 3 to 7 carbon atoms, a heterocyclyloxycarbonyl radical, a cycloalkoxy-carbonyl radical, the cycloalkyl part comprising from 3 to 7 carbon atoms, an alkylcarbonyloxy radical, the linear or branched alkyl part comprising from 1 to 6 carbon atoms, a cycloalkylcarbonyloxy radical, the cycloalkyl part comprising from 3 to 7 carbon atoms, an —$SR_1$, —$SOR_1$, —$SO_2R_1$, —$C(O)NR_1R_6$, —$NR_1R_6$, —$NR_1C(O)NR_1R_6$, —$NR_1(OR_2)$, —$C(R_1)=NR_6$ or —$N=NR_1R_2$ radical, a linear or branched alkyl radical comprising from 1 to 6 carbon atoms, a linear or branched alkenyl radical comprising from 1 to 6 carbon atoms, a cycloalkyl radical comprising from 3 to 7 carbon atoms, an aryl, aryloxy, heteroaryl, heteroaryloxy, arylalkyl, arylalkyloxy, heteroarylalkyl, heteroarylalkyloxy, arylcarbonyl, heteroarylcarbonyl, arylcarbonyloxy or heteroarylcarbonyloxy radical, the cyanato radical, the thiocyanato radical, the azido radical and the cyano radical;

$R_6$ is chosen from the hydrogen atom, a linear or branched alkyl radical comprising from 1 to 6 carbon atoms, a phenyl radical, a naphthyl radical, a phenylalkyl radical, the alkyl part being linear or branched and comprising from 1 to 6 carbon atoms, a naphthylalkyl radical, the alkyl part being linear or branched and comprising from 1 to 6 carbon atoms, an alkylcarbonyl radical, the linear or branched alkyl part comprising from 1 to 6 carbon atoms, an alkoxycarbonyl radical, the linear or branched alkyl part comprising from 1 to 6 carbon atoms, an N,N'-dialkylaminocarbamoyl radical, the linear or branched alkyl parts comprising from 1 to 6 carbon atoms, an alkylsulfonyl radical, the linear or branched alkyl part comprising from 1 to 6 carbon atoms, an arylsulfonyl radical and an N,N'-dialkylaminosulfonyl radical, the linear or branched alkyl parts comprising from 1 to 6 carbon atoms;

with the restriction that, for the compounds of formula (Ia), when Z represents the =CHCl radical and $R_1$, $R_2$, $R_3$, $R_4$ and $R_5$ each represent a hydrogen atom, then Y cannot represent the methylcarbonyl radical or the methoxycarbonyl radical, the formyl radical, the hydroxymethyl radical, the carboxyl radical, the bromo radical or the cyano radical, when Z represents the =CH$_2$ radical and $R_1$, $R_2$, $R_3$, $R_4$ and $R_5$ each represent a hydrogen atom, then Y cannot represent the methoxycarbonyl radical or the bromo radical, when Z represents the =O radical and $R_1$, $R_2$, $R_3$, $R_4$ and $R_5$ each represent a hydrogen atom, then Y cannot represent the bromo radical;

and that, for the compounds of formula (Ib), when Z represents the =CHCl radical and $R_1$, $R_2$, $R_3$, $R_3'$, $R_4$, $R_4'$ and $R_5$ each represent a hydrogen atom, then Y cannot represent the methylcarbonyl radical, when Z represents the =O radical and $R_2$, $R_3$, $R_3'$, $R_4$, $R_4'$ and $R_5$ each represent a hydrogen atom, then Y and $R_1$ cannot represent, both or independently of one another, a hydrogen atom or an alkyl radical comprising 1 to 4 carbon atoms;

and to their possible geometrical and/or optical isomers, to their possible tautomeric forms and to the salts, N-oxides and metal and semimetal complexes of the compounds as just defined.

The restrictions which have just been defined for the compounds of formula (Ia) or (Ib) apply for the compounds defined both generally and particularly or preferably.

Among the compounds of formula (Ia) or of formula (Ib) of the present invention, preference is also given to the compounds for which $R_3$ represents the hydrogen atom, the other substituents being as defined above.

Among the compounds of formula (Ia) or of formula (Ib) of the present invention, preference is also given to the compounds for which $R_2$ represents the hydrogen atom, the other substituents being as defined above.

Among the compounds of formula (Ia) or of formula (Ib) of the present invention, preference is also given to the compounds for which $R_1$ represents the hydrogen atom, the other substituents being as defined above.

Very particularly, the present invention relates to the compounds of formula (Ia) or of formula (Ib) for which $R_1$, $R_2$, $R_3$, $R_3'$ and $R_4'$ each represent the hydrogen atom, the other substituents being as defined above.

Among the compounds of formula (Ib) of the present invention, preference is given to the compounds for which $R_3'$ represents the hydrogen atom, the other substituents being as defined above.

The compounds of general formula (Ia) or of general formula (Ib) and the compounds which may possibly be used as intermediates in the preparation processes, and which will be defined on the occasion of the description of these processes, can exist in one or more forms of optical or chiral isomers, depending on the number of asymmetric centers in the compound. The invention thus relates just as well to all the optical isomers as to their racemic or scalemic mixtures (the term "scalemic" denotes a mixture of enantiomers in different proportions), and to the mixtures of all the possible stereoisomers in all proportions. The diastereoisomers and/or the optical isomers can be separated according to methods known to a person skilled in the art.

In the definitions of the compounds of formula (Ia) or of formula (Ib) presented above, it should be understood that, unless otherwise specified, the various radicals can optionally be substituted by one or more chemical entities chosen from the hydroxyl radical, a halogen atom chosen from fluorine, chlorine, bromine and iodine, the formyl radical, the carboxyl radical, a linear or branched alkyl radical comprising from 1 to 6 carbon atoms, a cycloalkyl radical comprising from 3 to 7 carbon atoms, a linear or branched alkoxy radical comprising from 1 to 6 carbon atoms, a cycloalkoxy radical comprising from 3 to 7 carbon atoms, an alkylcarbonyl radical, the linear or branched alkyl part comprising from 1 to 6 carbon atoms, a cycloalkylcarbonyl radical comprising from 3 to 7 carbon atoms, an alkoxycarbonyl radical, the linear or branched alkyl part comprising from 1 to 6 carbon atoms, a cycloalkyloxycarbonyl radical comprising from 3 to 7 carbon atoms, a heterocyclyloxycarbonyl radical, an —$SR_1$, —$SOR_1$, —$SO_2R_1$, —$C(O)NR_1R_6$ or —$NR_1R_6$ radical, the nitro radical, the cyanato radical, the thiocyanato radical, the azido radical, the pentafluorosulfonyl radical and the cyano radical.

In the context of the present invention, the term "aryl" means phenyl or naphthyl, the term "arylcarbonyl" meaning benzoyl or naphthoyl, and the term "arylalkyl" then meaning phenylalkyl or naphthylalkyl, more particularly benzyl, phenethyl, phenylpropyl, phenylbutyl, naphthylmethyl, naphthylethyl, naphthylpropyl or naphthylbutyl. It is understood that these various radicals can optionally be substituted by one or more identical or different $R_5$ and/or aryl and/or arylalkyl radicals.

Still in the context of the present invention, the term "heteroaryl" means a monocyclic or bicyclic aromatic system having from 4 to 10 ring members and comprising at least one heteroatom chosen from nitrogen, oxygen, sulfur, silicon and phosphorus. By way of example, such a heteroaryl radical can, inter alia, be chosen from furyl, pyrrolyl, thiophenyl, pyrazolyl, imidazolyl, oxazolyl, isoxazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1,2,3-triazolyl, 1,2,4-triazolyl, tetrazolyl, pyridyl, pyrimidinyl, pyrazinyl, pyridazinyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, benzimidazolyl, indazolyl, benzotriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 1,2,5-benzoxadiazolyl, 1,2,3-benzothiadiazolyl, 1,2,5-benzothiadiazolyl, quinolyl, isoquinolyl, quinoxazolinyl, quinazolinyl, cinnolyl, phthalazyl, pteridinyl, benzotriazinyl, 1,5-naphthyridinyl, 1,6-naphthyridinyl, 1,7-naphthyridinyl, 1,8-naphthyridinyl, imidazo[2,1-b]thiazolyl, thieno[3,4-b]pyridyl, puriny] or pyrrolo[1,2-b]thiazolyl.

Preparation Processes

The present invention also relates to the process for the preparation of the compounds of general formula (Ia) or of general formula (Ib), or their possible geometrical and/or optical isomers or their possible tautomeric forms, and their possible salts, N-oxides and metal and semimetal complexes of the compounds of formula (Ia) or of formula (Ib) as just defined.

The compounds of the present invention of general formula (Ia) or of general formula (Ib) and the compounds which may possibly be used as intermediates in the preparation processes can be prepared by at least one of the general preparation methods described below: methods A to L.

The preparation of the reactants used in one or other of the general preparation methods is usually known to a person skilled in the art and is usually specifically described in the prior art or is generally described, such that a person skilled in the art can adapt it to the desired purpose. The prior art which can be used by a person skilled in the art to establish the conditions for the preparation of the reactants can be found in numerous general chemical works, such as "Advanced Organic Chemistry" by J. March, published by Wiley (1992), "Methoden der Organischen Chemie" (Houben-Weyl), published by Georg Thieme Verlag, or "Chemical Abstracts", published by the American Chemical Society, and in the computer databases accessible to the public.

Method A:

The compounds of general formula (Ia) in which Y, $R_1$, $R_2$, $R_3$, $R_4$, $R_5$ and $R_6$ are as defined in the general formula and Z is the divalent radical =CWW', for which W is a halogen atom or the $R_1$ radical and W' is a halogen atom or a radical chosen from the $R_2$, $OR_2$, $SR_2$ or $NR_1R_6$ radicals, can be prepared by reaction of a compound of formula (IIa):

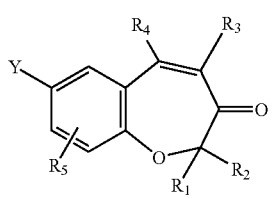

(IIa)

in which Y, $R_1$, $R_2$, $R_3$, $R_4$, $R_5$ and $R_6$ are as defined above, with a Wittig reagent of formula (XIII):

(Ph)$_3$P$^+$—CHW(W') X"$^-$ (XIII)

in which W is a halogen atom or the $R_1$ radical and W' is a halogen atom or a radical chosen from the $R_2$, $OR_2$, $SR_2$ or $NR_1R_6$ radicals, and X" is a halogen counterion, by the action of one or more equivalents of a base, such as alkali metal or alkaline earth metal alkoxides, preferably sodium ethoxide, sodium methoxide or potassium tert-butoxide, or alkali metal and alkaline earth metal hydrides, preferably sodium hydride or potassium hydride, or of an organometallic derivative, such as alkyllithium compounds, preferably butyllithium, alkylmagnesium halides or lithium diisopropylamide, in an aprotic solvent, such as ethers, preferably diethyl ether or tetrahydrofuran, at a temperature of −78° C. to 50° C., preferably −70° C. to 20° C., according to J. March, ibid., pages 956–963.

Similarly, the compounds of general formula (Ia) in which Y, $R_1$, $R_2$, $R_3$, $R_4$, $R_5$ and $R_6$ are as defined in the general formula and Z is the divalent radical =CWW', for which W is the $R_1$ radical and W' is a radical chosen from the cyano, C(O)$R_2$ or C(O)O$R_2$ radicals, can be prepared by reaction of a compound of formula (IIa), in which Y, $R_1$, $R_2$, $R_3$, $R_4$, $R_5$ and $R_6$ are as defined above, with a Wittig-Horner reagent of formula (XIV):

(EtO)$_2$P(O)CHWW' (XIV)

in which W is the $R_1$ radical and W' is a radical chosen from the cyano, C(O)$R_2$ or C(O)O$R_2$ radicals, by the action of one or more equivalents of a base, such as alkali metal or alkaline earth metal alkoxides, preferably sodium ethoxide, sodium methoxide or potassium tert-butoxide, or alkali metal and alkaline earth metal hydrides, preferably sodium hydride or potassium hydride, or of an organometallic derivative, such as alkyllithium compounds, preferably butyllithium, alkylmagnesium halides or lithium diisopropylamide, in an aprotic solvent, such as ethers, preferably diethyl ether or tetrahydrofuran, at a temperature of −78° C. to 50° C., preferably −70° C. to 20° C., according to J. March, ibid., pages 956–963.

The compounds of general formula (IIa) in which Y, $R_1$, $R_2$, $R_3$, $R_4$, $R_5$ and $R_6$ are as defined above can be prepared by elimination of a sulfinate group from a compound of formula (IIIa):

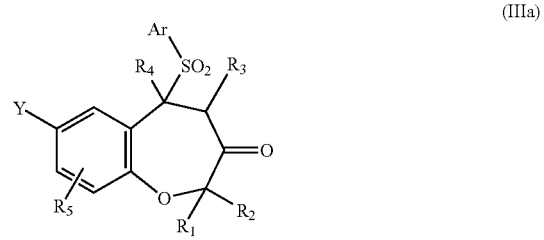

(IIIa)

in which Y, $R_1$, $R_2$, $R_3$, $R_4$, $R_5$ and $R_6$ are as defined above and Ar is a phenyl or toluyl radical, by the action of one or more equivalents of a base, such as sodium hydroxide or potassium hydroxide, alkali metal or alkaline earth metal alkoxides, such as sodium methoxide or potassium ethoxide, or nitrogenous bases optionally supported on resin, such as pyridine, triethylamine, diethylisopropylamine, 1,5-diaza-bicyclo[4.3.0]non-5-ene or 1,8-diazabicyclo[5.4.0]-undec-7-ene. The appropriate solvent for this reaction can be a halogenated hydrocarbon, such as dichloromethane, chloroform, 1,2-dichloroethane or 1,1,1-trichloroethane, an ether, such as diethyl ether, diisopropyl ether, tetrahydrofuran, dioxane or dimethoxyethane, or a protic solvent, such as alcohols (in particular methanol, ethanol, propanol, isopropanol or tert-butanol) or water. Mixtures of these various solvents can also be used.

The reaction time depends on the conditions used and is generally between 0.1 and 48 h and is generally carried out at a temperature of between −80° C. and 180° C. (preferably between 0° C. and 100° C.) in the absence or in the presence of a catalytic or noncatalytic amount of an acid. There is no absolute limit for the relative proportions of compound of formula (IIIa) and of base. However, it is advantageous to choose a base/(IIIa) molar ratio of between 0.1 and 20, preferably 1 to 5.

The compounds of general formula (IIIa) in which Y, $R_1$, $R_2$, $R_3$, $R_4$, $R_5$ and $R_6$ are as defined above and Ar is a phenyl or toluyl radical can be prepared by oxidation of a compound of formula (IVa):

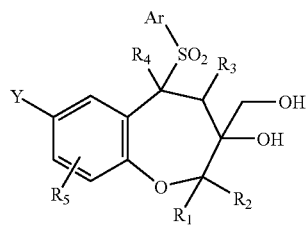

(IVa)

in which Y, $R_1$, $R_2$, $R_3$, $R_4$, $R_5$ and $R_6$ are as defined above and Ar is a phenyl or toluyl radical, by the action of one or more equivalents of an oxidizing agent, such as molecular oxygen, peroxides (in particular hydrogen peroxide or tert-butyl peroxide), chromium derivatives, such as chromium oxide or pyridinium dichromate, metal oxides, such as manganese oxide or potassium permanganate, lead tetraacetate, sodium bismuthate, periodates, such as periodic acid or sodium periodate, or metal nitrates, such as silver nitrate, manganese nitrate or thallium nitrate. The appropriate solvent for this reaction can be an aromatic hydrocarbon, such as benzene, a halogenated hydrocarbon, such as dichloromethane, chloroform, 1,2-dichloroethane or 1,1,1-trichloro-ethane, an ester, such as methyl acetate or ethyl acetate, a nitrile, such as acetonitrile, propionitrile or benzonitrile, a nitrogenous solvent, such as pyridine, 2,6-lutidine or 2,4,6-collidine, or a protic solvent, such as alcohols (in particular methanol, ethanol, propanol, isopropanol or tert-butanol), a carboxylic acid, such as acetic acid or propanoic acid, or water. Mixtures of these various solvents can also be used.

The reaction time depends on the conditions used and is generally between 0.1 and 48 h and is generally carried out at a temperature of between −80° C. and 180° C. (preferably between 0° C. and 150° C.) in the absence or in the presence of a catalytic or noncatalytic amount of an acid. There is no absolute limit for the relative proportions of compound of formula (IVa) and of oxidizing agent. However, it is advantageous to choose an oxidizing agent/(IVa) molar ratio of between 0.1 and 100, preferably 1 to 20.

The compounds of general formula (IVa) in which Y, $R_1$, $R_2$, $R_3$, $R_4$, $R_5$ and $R_6$ are as defined above and Ar is a phenyl or toluyl radical can be prepared by oxidation of a compound of formula (Va):

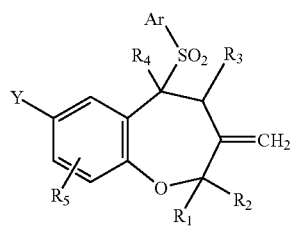

(Va)

in which Y, $R_1$, $R_2$, $R_3$, $R_4$, $R_5$ and $R_6$ are as defined above and Ar is a phenyl or toluyl radical, by the action of a catalytic amount or of one or more equivalents of an oxidizing agent, such as molecular oxygen, ozone, peroxides (in particular hydrogen peroxide, tert-butyl peroxide, dimethyldioxirane or 3-chloroperoxybenzoic acid), potassium permanganate, cerium ammonium nitrate, lead tetraacetate, osmium tetroxide or the osmium tetroxide/ $(DHQD)_2$-PHAL complex.

The appropriate solvent for this reaction can be an aromatic or aliphatic hydrocarbon, such as benzene or alkanes, a halogenated hydrocarbon, such as dichloromethane, chloroform, 1,2-dichloroethane or 1,1,1-trichloroethane, an ether, such as diethyl ether or diisopropyl ether, a ketone, such as acetone or methyl ethyl ketone, an ester, such as methyl acetate or ethyl acetate, a nitrile, such as acetonitrile, propionitrile or benzonitrile, a nitrogenous solvent, such as pyridine, 2,6-lutidine or 2,4,6-collidine, or a protic solvent, such as alcohols (in particular methanol, ethanol, propanol, isopropanol or tert-butanol) or water. Mixtures of these various solvents can also be used.

The reaction time depends on the conditions used and is generally between 0.1 and 48 h and is generally carried out at a temperature of between −80° C. and 180° C. (preferably between 0° C. and 150° C.) in the absence or in the presence of one or more equivalents of a cooxidant, such as 4-methylmorpholine N-oxide, trimethylamine N-oxide or potassium ferricyanide. There is no absolute limit for the relative proportions of compound of formula (Va) and of oxidizing agent. However, it is advantageous to choose an oxidizing agent/(Va) molar ratio of between 0.1 and 100, preferably 0.2 to 20.

The compounds of general formula (IIIa) in which Y, $R_1$, $R_2$, $R_3$, $R_4$, $R_5$ and $R_6$ are as defined above and Ar is a phenyl or toluyl radical can be prepared directly by oxidation of a compound of formula (Va), in which Y, $R_1$, $R_2$, $R_3$, $R_4$, $R_5$ and $R_6$ are as defined above and Ar is a phenyl or toluyl radical, by the action of one or more equivalents of an oxidizing agent, such as ozone, in the presence or absence of dimethyl sulfide or trimethylphosphine. The appropriate solvent for this reaction can be a halogenated hydrocarbon, such as dichloromethane, chloroform, 1,2-dichloroethane or 1,1,1-trichloro-ethane, a ketone, such as acetone or methyl ethyl ketone, a nitrogenous solvent, such as pyridine, 2,6-lutidine or 2,4,6-collidine, or a protic solvent, such as alcohols (in particular methanol, ethanol, propanol, isopropanol or tert-butanol), a carboxylic acid, such as acetic acid or propanoic acid, or water. Mixtures of these various solvents can also be used.

The reaction time depends on the conditions used and is generally between 0.1 and 48 h and is generally carried out at a temperature of between −80° C. and 180° C. (preferably between −20° C. and 50° C.). There is no absolute limit for the relative proportions of compound of formula (Va) and ozone. However, it is advantageous to choose an ozone/(Va) molar ratio of between 0.1 and 100, preferably 1 to 20.

The compounds of general formula (IIa) in which Y, $R_1$, $R_2$, $R_3$, $R_4$, $R_5$ and $R_6$ are as defined above and Ar is a phenyl or toluyl radical can be prepared directly from a compound of formula (Va), in which Y, $R_1$, $R_2$, $R_3$, $R_4$, $R_5$ and $R_6$ are as defined above and Ar is a phenyl or toluyl radical, by the action of one or more equivalents of an oxidizing agent, such as ozone, followed by the action of a base, in a way in every respect similar to that described in method A for the oxidation of the compounds (Va) to (IIIa) and the elimination of a sulfinate group from the compounds (IIIa) to give (IIa).

The compounds of general formula (Va) in which Y, $R_1$, $R_2$, $R_3$, $R_4$, $R_5$ and $R_6$ are as defined above and Ar is a phenyl or toluyl radical can be prepared by cyclization of a compound of formula (VIa):

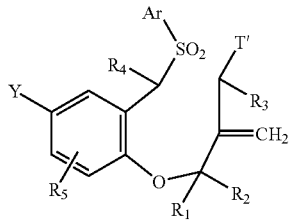

(VIa)

in which Y, $R_1$, $R_2$, $R_3$, $R_4$, $R_5$ and $R_6$ are as defined above, Ar is a phenyl or toluyl radical and T' is a halogen atom, preferably chlorine or bromine, or a sulfonate, such as phenylsulfonate, 4-methylphenylsulfonate, methylsulfonate or trifluoromethylsulfonate, by the action of one or more equivalents of a base, such as potassium tert-butoxide, alkali metal hydrides, such as sodium hydride or potassium hydride, alkyllithium compounds, such as butyllithium, sec-butyllithium or tert-butyllithium, or alkali metal salts of nitrogenous bases optionally supported on a resin, such as lithium diisopropylamide, potassium diisopropylamide, lithium bis(trimethylsilyl)amide or potassium bis(trimethylsilyl)amide, in the presence of a catalytic amount or of one or more equivalents of hexamethylphosphoramide or of dimethylpropyleneurea. The appropriate solvent for this reaction can be an ether, such as diethyl ether, diisopropyl ether, tetrahydrofuran, dioxane, dimethoxyethane or glyme. The reaction time depends on the conditions used and is generally between 0.1 and 48 h and is generally carried out at a temperature of between −80° C. and 180° C. (preferably between 0° C. and 50° C.). There is no absolute limit for the relative proportions of compound of formula (VIa) and of base. However, it is advantageous to choose a base/(VIa) molar ratio of between 0.1 and 100, preferably 1 to 5. There is no absolute limit for the concentration of the compound of formula (VIa) in the solvent. However, it is advantageous to choose a 1 molar to 0.001 molar concentration of compound of formula (VIa) in the solvent, preferably 0.1 to 0.01 molar.

The general conditions of this reaction are described in particular by D. Crich et al. (*Journal of the Chemical Society; Chemical Communication*, (1995), 85) and P. Lansbury et al. (*Tetrahedron Letters*, 31, (1990), 3965).

The compounds of general formula (VIa) in which Y, $R_1$, $R_2$, $R_3$, $R_4$, $R_5$ and $R_6$ are as defined above, Ar is a phenyl or toluyl radical and T' is a halogen atom, preferably chorine or bromine, or a sulfonate, such as phenylsulfonate, 4-methylphenylsulfonate, methyl-sulfonate or trifluoromethylsulfonate, can be prepared by condensation of a compound of formula (VII):

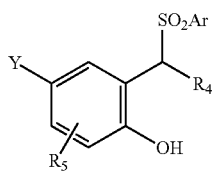

(VII)

in which Y, $R_4$, $R_5$ and $R_6$ are as defined above and Ar is a phenyl or toluyl radical, with a compound of formula (VIIIa):

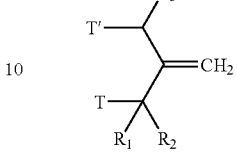

(VIIIa)

in which $R_1$, $R_2$ and $R_3$ are as defined above and T and T' are, independently of one another, a halogen atom, preferably chlorine or bromine, or a sulfonate, such as phenylsulfonate, 4-methylphenylsulfonate, methyl-sulfonate or trifluoromethylsulfonate, by the action of one or more equivalents of a base, such as alkali metal and alkaline earth metal hydroxides, in particular sodium hydroxide, potassium hydroxide, cesium hydroxide or calcium hydroxide, alkali metal and alkaline earth metal alkoxides, such as potassium tert-butoxide, alkali metal and alkaline earth metal hydrides, such as sodium hydride, potassium hydride or cesium hydride, alkali metal and alkaline earth metal carbonates and bicarbonates, such as sodium carbonate, potassium carbonate, calcium carbonate, sodium bicarbonate, potassium bicarbonate or calcium bicarbonate, alkali metal salts of nitrogenous bases optionally supported on a resin, such as lithium diisopropylamide, potassium diisopropylamide, lithium bis(trimethylsilyl)amide or potassium bis(trimethylsilyl)amide, or nitrogenous bases optionally supported on a resin, such as trimethylamine, triethylamine, diisopropylethylamine, 1,5-diazabicyclo[4.3.0]non-5-ene, 1,8-diazabicyclo[5.4.0]undec-7-ene or tris(dimethylamino)-N-(tert-butyl)phosphinimine, in the presence of a catalytic or noncatalytic amount of iodide salt, such as lithium iodide, sodium iodide, potassium iodide or tetraalkylammonium iodides.

The appropriate solvent for this reaction can be an ether, such as diethyl ether, diisopropyl ether, tetrahydrofuran, dioxane or dimethoxyethane, a ketone, such as acetone or methyl ethyl ketone, a nitrile, such as acetonitrile, propionitrile or benzonitrile, a dipolar aprotic solvent, such as dimethylformamide, dimethylacetamide, N-methylpyrrolidone, dimethylpropyleneurea or dimethyl sulfoxide, or a protic solvent, such as alcohols (in particular methanol, ethanol, propanol, isopropanol or tert-butanol) or water. The reaction time depends on the conditions used and is generally between 0.1 and 48 h and is generally carried out at a temperature of between −80° C. and 180° C. (preferably between 0° C. and 50° C.). There is no absolute limit for the relative proportions of compound of formula (VII), of compound of formula (VIIIa) and of base. However, it is advantageous to choose a base/(VII) molar ratio of between 0.1 and 100, preferably 1 to 5, and an (VIIIa)/(VII) molar ratio of between 0.1 and 20, preferably 1 to 3. There is no absolute limit for the concentration of the compound of formula (VII) in the solvent. However, it is advantageous to choose a 1 molar to 0.001 molar concentration of compound of formula (VII) in the solvent, preferably 0.1 to 0.01 molar.

The compounds of formula (VII) can more particularly be prepared according to a great many processes known to a person skilled in the art and described in particular by R. Collins et al. (*Journal of the Chemical Society; C*, (1966), 873–880) and C. Kaiser et al. (*Journal of Medicinal Chemistry*, 18, (1975), 674–683).

The compounds of formula (VIIIa) can be prepared according to a great many processes known to a person skilled in the art.

Method B:

The compounds of general formula (Ib) in which Y, $R_1$, $R_2$, $R_3$, $R_3'$, $R_4$, $R_5$ and $R_6$ are as defined in the general formula, $R_4'$ is a hydrogen atom and Z is the divalent radical =CWW', for which W is a halogen atom or the $R_1$ radical and W' is a halogen atom or a radical chosen from the $R_2$, $OR_2$, $SR_2$ or $NR_1R_6$ radicals, can be prepared by reaction of a compound of formula (IIb):

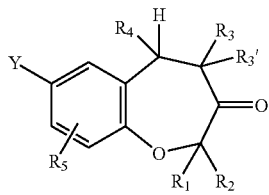

(IIb)

in which Y, $R_1$, $R_2$, $R_3$, $R_3'$, $R_4$, $R_5$ and $R_6$ are as defined above, with a Wittig reagent of formula (XIII):

$(Ph)_3P^+$—CHW(W')X"$^-$ (XIII)

in which W is a halogen atom or the $R_1$ radical and W' is a halogen atom or a radical chosen from the $R_2$, $OR_2$, $SR_2$ or $NR_1R_6$ radicals, and X" is a halogen counterion, by the action of one or more equivalents of a base, such as alkali metal or alkaline earth metal alkoxides, preferably sodium ethoxide, sodium methoxide or potassium tert-butoxide, or alkali metal and alkaline earth metal hydrides, preferably sodium hydride or potassium hydride, or of an organometallic derivative, such as alkyllithium compounds, preferably butyllithium, alkylmagnesium halides or lithium diisopropylamide, in an aprotic solvent, such as ethers, preferably diethyl ether or tetrahydrofuran, at a temperature of −78° C. to 50° C., preferably −70° C. to 20° C., according to J. March, ibid., pages 956–963.

Similarly, the compounds of general formula (Ib) in which Y, $R_1$, $R_2$, $R_3$, $R_3'$, $R_4$, $R_5$ and $R_6$ are as defined in the general formula, $R_4'$ is the hydrogen atom and Z is the divalent radical =CWW', for which W is the $R_1$ radical and W' is a radical chosen from the cyano, $C(O)R_2$ or $C(O)OR_2$ radicals, can be prepared by reaction of a compound of formula (IIb), in which Y, $R_1$, $R_2/R_3$, $R_3'$, $R_4$, $R_5$ and $R_6$ are as defined above, with a Wittig-Horner reagent of formula (XIV):

$(EtO)_2P(O)CHWW'$ (XIV)

in which W is the $R_1$ radical and W' is a radical chosen from the cyano, $C(O)R_2$ or $C(O)OR_2$ radicals, by the action of one or more equivalents of a base, such as alkali metal or alkaline earth metal alkoxides, preferably sodium ethoxide, sodium methoxide or potassium tert-butoxide, or alkali metal and alkaline earth metal hydrides, preferably sodium hydride or potassium hydride, or of an organometallic derivative, such as alkyllithium compounds, preferably butyllithium, alkylmagnesium halides or lithium diisopropylamide, in an aprotic solvent, such as ethers, preferably diethyl ether or tetrahydrofuran, at a temperature of −78° C. to 50° C., preferably −70° C. to 20° C., according to J. March, ibid., pages 956–963.

The compounds of general formula (IIb) in which Y, $R_1$, $R_2$, $R_3$, $R_3'$, $R_4$, $R_5$ and $R_6$ are as defined above can also be prepared by oxidation of a compound of formula (IXb):

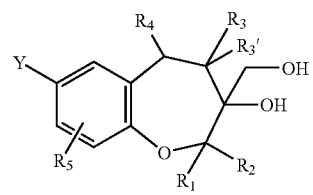

(IXb)

in which Y, $R_1$, $R_2$, $R_3$, $R_3'$, $R_4$, $R_5$ and $R_6$ are as defined above, in a way in every respect similar to that described in method A for the oxidation of the compounds (IVa) to (IIIa).

The compounds of general formula (IXb) in which Y, $R_1$, $R_2$, $R_3$, $R_3'$, $R_4$, $R_5$ and $R_6$ are as defined above can also be prepared by oxidation of the exocyclic double bond of a compound of formula (Xb):

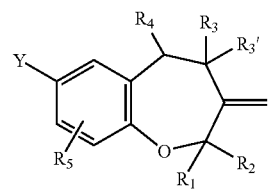

(Xb)

in which Y, $R_1$, $R_2$, $R_3$, $R_3'$, $R_4$, $R_5$ and $R_6$ are as defined above, in a way in every respect similar to that described in method A for the oxidation of the compounds (Va) to (IVa).

The compounds of general formula (IIa) in which Y, $R_1$, $R_2$, $R_3$, $R_4$, $R_5$ and $R_6$ are as defined above and Ar is a phenyl or toluyl radical can be prepared directly by oxidation of a compound of formula (Xb), in which Y, $R_1$, $R_2$, $R_3$, $R_4$, $R_5$ and $R_6$ are as defined above and Ar is a phenyl or toluyl radical, by the action of one or more equivalents of an oxidizing agent, such as ozone, in a way in every respect similar to that described in method A for the oxidation of the compounds (Va) to (IIIa).

The compounds of general formula (Xb) in which Y, $R_1$, $R_2$, $R_3$, $R_3'$, $R_4$, $R_5$ and $R_6$ are as defined above and Ar is a phenyl or toluyl radical can be prepared by reduction of a compound of formula (Vb):

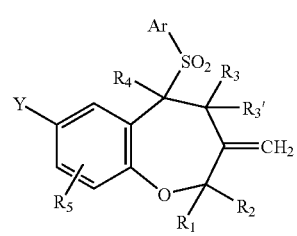

(Vb)

in which Y, $R_1$, $R_2$, $R_3$, $R_3'$, $R_4$, $R_5$ and $R_6$ are as defined above and Ar is a phenyl or toluyl radical, by the action of one or more equivalents of a reducing agent, such as amalgams, in particular sodium amalgam, potassium amalgam or aluminum amalgam, metals, such as zinc, samarium or magnesium with optional addition of one or more equivalents of mercuric chloride, trialkyltin hydrides, such as tributyltin hydride, or samarium iodide. The appropriate solvent for this reaction can be a halogenated hydrocarbon, such as dichloromethane or chloroform, an ether, such as diethyl ether, diisopropyl ether, tetrahydrofuran, dioxane or dimethoxyethane, or a protic solvent, such as alcohols, in particular methanol, ethanol, propanol, isopropanol or tert-butanol, a carboxylic acid, such as acid acid or propionic acid, or water. Mixtures of these various solvents can also be used.

The reaction time depends on the conditions used and is generally between 0.1 and 48 h and is generally carried out at a temperature of between −80° C. and 180° C. (preferably between 0° C. and 100° C.) in the absence or in the presence of a catalytic or noncatalytic amount of an acid. There is no absolute limit for the relative proportions of compound of formula (Vb) and of reducing agent. However, it is advantageous to choose a reducing agent/(Vb) molar ratio of between 0.1 and 20, preferably 1 to 5.

The compounds of general formula (Vb) in which Y, $R_1$, $R_2$, $R_3$, $R_3'$, $R_4$, $R_5$ and $R_6$ are as defined above and Ar is a phenyl or toluyl radical can be prepared by cyclization of a compound of formula (VIb):

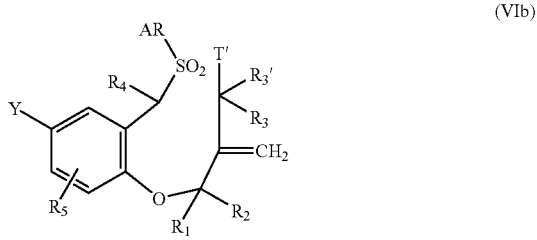

(VIb)

in which Y, $R_1$, $R_2$, $R_3$, $R_3'$, $R_4$, $R_5$ and $R_6$ are as defined above, Ar is a phenyl or toluyl radical and T' is a halogen atom, preferably chorine or bromine, or a sulfonate, such as phenylsulfonate, 4-methylphenylsulfonate, methylsulfonate or trifluoromethylsulfonate, by the action of one or more equivalents of a base, such as potassium tert-butoxide, alkali metal hydrides, such as sodium hydride or potassium hydride, alkyllithium compounds, such as butyllithium, sec-butyllithium or tert-butyllithium, or alkali metal salts of nitrogenous bases optionally supported on a resin, such as lithium diisopropylamide, potassium diisopropylamide, lithium bis(trimethylsilyl)amide or potassium bis(trimethylsilyl)amide, in the presence of a catalytic amount or of one or more equivalents of hexamethylphosphoramide or of dimethylpropyleneurea. The appropriate solvent for this reaction can be an ether, such as diethyl ether, diisopropyl ether, tetrahydrofuran, dioxane, dimethoxyethane or glyme. The reaction time depends on the conditions used and is generally between 0.1 and 48 h and is generally carried out at a temperature of between −80° C. and 180° C. (preferably between 0° C. and 50° C.). There is no absolute limit for the relative proportions of compound of formula (VIb) and of base. However, it is advantageous to choose a base/(VIb) molar ratio of between 0.1 and 100, preferably 1 to 5. There is no absolute limit for the concentration of the compound of formula (VIb) in the solvent. However, it is advantageous to choose a 1 molar to 0.001 molar concentration of compound of formula (VIb) in the solvent, preferably 0.1 to 0.01 molar.

The general conditions of this reaction are described in particular by D. Crich et al. (*Journal of the Chemical Society; Chemical Communication*, (1995), 85) and P. Lansbury et al. (*Tetrahedron Letters,* 31, (1990), 3965).

The compounds of general formula (VIb) in which Y, $R_1$, $R_2$, $R_3$, $R_3'$, $R_4$, $R_5$ and $R_6$ are as defined above, Ar is a phenyl or toluyl radical and T' is a halogen atom, preferably chlorine or bromine, or a sulfonate, such as phenylsulfonate, 4-methylphenylsulfonate, methyl-sulfonate or trifluoromethylsulfonate, can be prepared by condensation of a compound of formula (VII), in which Y, $R_4$, $R_5$ and $R_6$ are as defined above and Ar is a phenyl or toluyl radical, with a compound of formula (VIIIb):

(VIIIb)

in which $R_1$, $R_2$, $R_3$ and $R_3'$ are as defined above and T and T' are, independently of one another, a halogen atom, preferably chlorine or bromine, or a sulfonate, such as phenylsulfonate, 4-methylphenylsulfonate, methylsulfonate or trifluoromethylsulfonate, by the action of one or more equivalents of a base, such as alkali metal and alkaline earth metal hydroxides, in particular sodium hydroxide, potassium hydroxide, cesium hydroxide or calcium hydroxide, alkali metal and alkaline earth metal alkoxides, such as potassium tert-butoxide, alkali metal and alkaline earth metal hydrides, such as sodium hydride, potassium hydride or cesium hydride, alkali metal and alkaline earth metal carbonates and bicarbonates, such as sodium carbonate, potassium carbonate, calcium carbonate, sodium bicarbonate, potassium bicarbonate or calcium bicarbonate, alkali metal salts of nitrogenous bases optionally supported on a resin, such as lithium diisopropylamide, potassium diisopropylamide, lithium bis(trimethylsilyl) amide or potassium bis(trimethylsilyl)amide, or nitrogenous bases optionally supported on a resin, such as trimethylamine, triethylamine, diisopropylethylamine, 1,5-diazabicyclo[4.3.0]non-5-ene, 1,8-diazabicyclo[5.4.0]undec-7-ene or tris(dimethylamino)-N-(tert-butyl)phosphinimine, in the presence of a catalytic or noncatalytic amount of iodide salt, such as lithium iodide, sodium iodide, potassium iodide or tetraalkylammonium iodides.

The appropriate solvent for this reaction can be an ether, such as diethyl ether, diisopropyl ether, tetrahydrofuran, dioxane or dimethoxyethane, a ketone, such as acetone or methyl ethyl ketone, a nitrile, such as acetonitrile, propionitrile or benzonitrile, a dipolar aprotic solvent, such as dimethylformamide, dimethylacetamide, N-methylpyrrolidone, dimethylpropyleneurea or dimethyl sulfoxide, or a protic solvent, such as alcohols (in particular methanol, ethanol, propanol, isopropanol or tert-butanol) or water. The reaction time depends on the conditions used and is generally between 0.1 and 48 h and is generally carried out at a temperature of between −80° C. and 180° C. (preferably between 0° C. and 50° C.). There is no absolute limit for the relative proportions of compound of formula (VII), of compound of formula (VIIIb) and of base. However, it is advantageous to choose a base/(VII) molar ratio of between 0.1 and 100, preferably 1 to 5, and an (VIIIb)/(VII) molar ratio of between 0.1 and 20, preferably 1 to 3. There is no absolute limit for the concentration of the compound of formula (VII) in the solvent. However, it is advantageous to choose a 1 molar to 0.001 molar concentration of compound of formula (VII) in the solvent, preferably 0.1 to 0.01 molar.

The compounds of formula (VIIIb) can be prepared according to a great many processes known to a person skilled in the art.

Method C:

The compounds of general formula (Ia) in which Y, $R_1$, $R_2$, $R_3$, $R_4$, $R_5$ and $R_6$ are as defined in the general formula and Z is the divalent radical =CWW', in which W is a halogen atom or the $R_1$ radical and W' is a halogen atom or a radical chosen from the $R_2$, $OR_2$, $SR_2$, $NR_1R_6$, cyano, $C(O)R_2$ or $C(O)OR_2$ radicals, the exocyclic double bond being of E stereochemistry, can be prepared by isomerization of a compound of general formula (Ia) in which Y, $R_1$, $R_2$, $R_3$, $R_4$, $R_5$ and $R_6$ are as defined in the general formula and Z is the divalent radical =CWW' for which W is a halogen atom or the $R_1$ radical and W' is a halogen atom or a radical chosen from the $R_2$, $OR_2$, $SR_2$, $NR_1R_6$, cyano, $C(O)R_2$ or $C(O)OR_2$ radicals, the exocyclic double bond being of Z stereochemistry, by heating in a solvent, preferably under ultraviolet irradiation, in the absence of or with a catalyst, in particular an acid catalyst or molecular iodine. The reaction time is chosen so as to obtain complete conversion of the Z isomer to the E isomer or a high proportion of E isomer in the mixture. The reaction is generally carried out at a temperature of between 0° C. and the boiling point of the solvent. The appropriate solvent for this reaction can be an aliphatic hydrocarbon, such as pentane, hexane, heptane or octane; an aromatic hydrocarbon, such as benzene, toluene, or xylenes; an ether, such as diethyl ether, diisopropyl ether, tetrahydrofuran, dioxane or dimethoxyethane; a halogenated hydrocarbon, such as dichloromethane, chloroform, 1,2-dichloroethane or 1,1,1-trichloroethane; an ester, such as methyl acetate or ethyl acetate; a nitrile, such as acetonitrile, propionitrile or benzonitrile; an alcohol, such as methanol, ethanol, propanol or isopropanol; a dipolar aprotic solvent, such as dimethylformamide, dimethylacetamide, N-methylpyrrolidone, dimethylpropyleneurea or dimethyl sulfoxide; or water. Mixtures of these various solvents can also be used.

The solvent will preferably be an aromatic solvent, such as toluene or xylenes, or an ether, such as diisopropyl ether. The catalyst, preferably an acid catalyst, will be chosen from anhydrous hydracids, such as hydrogen chloride, carboxylic acids, such as acetic acid, propionic acid or trifluoroacetic acid, sulfonic acids, such as methanesulfonic, trifluoromethanesulfonic or 4-methylphenylsulfonic acid, or sulfuric acid.

Method D:

The compounds of general formula (Ib) in which Y, $R_1$, $R_2$, $R_3$, $R_3'$, $R_4$, $R_4'$, $R_5$ and $R_6$ are as defined in the general formula and Z is the divalent radical =CWW', in which W is a halogen atom or the $R_1$ radical and W' is a halogen atom or a radical chosen from the $R_2$, $OR_2$, $SR_2$, $NR_1R_6$, cyano, $C(O)R_2$ or $C(O)OR_2$ radicals, the exocyclic double bond being of E stereochemistry, can be prepared by isomerization of a compound of general formula (Ib) in which Y, $R_1$, $R_2$, $R_3$, $R_3'$, $R_4$, $R_4'$, $R_5$ and $R_6$ are as defined in the general formula and Z is the divalent radical =CWW' for which W is a halogen atom or the $R_1$ radical and W' is a halogen atom or a radical chosen from the $R_2$, $OR_2$, $SR_2$, $NR_1R_6$, cyano, $C(O)R_2$ or $C(O)OR_2$ radicals, the exocyclic double bond being of Z stereochemistry, by heating in a solvent, preferably under ultraviolet irradiation, in the absence of or with a catalyst, in particular an acid catalyst or molecular iodine. The reaction time is chosen so as to obtain complete conversion of the Z isomer to the E isomer or a high proportion of E isomer in the mixture. The reaction is generally carried out at a temperature of between 0° C. and the boiling point of the solvent. The appropriate solvent for this reaction can be an aliphatic hydrocarbon, such as pentane, hexane, heptane or octane; an aromatic hydrocarbon, such as benzene, toluene, or xylenes; an ether, such as diethyl ether, diisopropyl ether, tetrahydrofuran, dioxane or dimethoxyethane; a halogenated hydrocarbon, such as dichloromethane, chloroform, 1,2-dichloroethane or 1,1,1-trichloroethane; an ester, such as methyl acetate or ethyl acetate; a nitrile, such as acetonitrile, propionitrile or benzonitrile; an alcohol, such as methanol, ethanol, propanol or isopropanol; a dipolar aprotic solvent, such as dimethylformamide, dimethylacetamide, N-methylpyrrolidone, dimethylpropyleneurea or dimethyl sulfoxide; or water. Mixtures of these various solvents can also be used.

The solvent will preferably be an aromatic solvent, such as toluene or xylenes, or an ether, such as diisopropyl ether. The catalyst, preferably an acid catalyst, will be chosen from anhydrous hydracids, such as hydrogen chloride, carboxylic acids, such as acetic acid, propionic acid or trifluoroacetic acid, sulfonic acids, such as methanesulfonic, trifluoromethanesulfonic or 4-methylphenylsulfonic acid, or sulfuric acid.

Method E:

The compounds of general formula (Ia) in which $R_1$, $R_2$, $R_3$, $R_4$, $R_5$ and $R_6$ are as defined in the general formula, Z is the divalent radical =CWW', for which W is a halogen atom or the $R_1$ radical and W' is a halogen atom or a radical chosen from the $R_2$, $OR_2$, $SR_2$ or $NR_1R_6$ radicals, and Y is the alkylcarbonyl, arylcarbonyl or heteroarylcarbonyl radical, can be prepared by regioselective reaction of a compound of formula (IIa), in which $R_1$, $R_2$, $R_3$, $R_4$, $R_5$ and $R_6$ are as defined above and Y is the alkylcarbonyl, arylcarbonyl or heteroarylcarbonyl radical, with a Wittig reagent of formula (XIII) in which W is a halogen atom or the $R_1$ radical and W' is a halogen atom or a radical chosen from the $R_2$, $OR_2$, $SR_2$ or $NR_1R_6$ radicals, and X" is a halogen counterion, in a way in every respect similar to that described in method A.

Similarly, the compounds of general formula (Ia) in which $R_1$, $R_2$, $R_3$, $R_4$, $R_5$ and $R_6$ are as defined in the general formula, Z is the divalent radical =CWW', for which W is the $R_1$ radical and W' is a radical chosen from the cyano, $C(O)R_2$ or $C(O)OR_2$ radicals, and Y is the alkylcarbonyl, arylcarbonyl or heteroarylcarbonyl radical, can be prepared by regioselective reaction of a compound of formula (IIa), in which $R_1$, $R_2$, $R_3$, $R_4$, $R_5$ and $R_6$ are as defined above and Y is the alkylcarbonyl, arylcarbonyl or heteroarylcarbonyl radical, with a Wittig-Horner reagent of formula (XIV) in which W is the $R_1$ radical and W' is a radical chosen from the cyano, $C(O)R_2$ or $C(O)OR_2$ radicals, in a way in every respect similar to that described in method A.

Method F:

The compounds of general formula (Ib) in which $R_1$, $R_2$, $R_3$, $R_3'$, $R_4$, $R_4'$, $R_5$ and $R_6$ are as defined in the general formula, Z is the divalent radical =CWW', for which W is a halogen atom or the $R_1$ radical and W' is a halogen atom or a radical chosen from the $R_2$, $OR_2$, $SR_2$ or $NR_1R_6$ radicals, and Y is the alkylcarbonyl, arylcarbonyl or heteroarylcarbonyl radical, can be prepared by regioselective reaction of a compound of formula (IIa), in which $R_1$, $R_2$, $R_3$, $R_3'$, $R_4$, $R_4'$, $R_5$ and $R_6$ are as defined above and Y is the alkylcarbonyl, arylcarbonyl or heteroarylcarbonyl radical, with a Wittig reagent of formula (XIII) in which W is a halogen atom or the $R_1$ radical and WI is a halogen atom or a radical chosen from the $R_2$, $OR_2$, $SR_2$ or $NR_1R_6$ radicals, and X" is a halogen counterion, in a way in every respect similar to that described in method A.

Similarly, the compounds of general formula (Ib) in which $R_1$, $R_2$, $R_3$, $R_3'$, $R_4$, $R_4'$, $R_5$ and $R_6$ are as defined in the general formula, Z is the divalent radical =CWW', for which W is the $R_1$ radical and W' is a radical chosen from the cyano, $C(O)R_2$ or $C(O)OR_2$ radicals, and Y is the alkylcarbonyl, arylcarbonyl or heteroarylcarbonyl radical, can be prepared by regioselective reaction of a compound of formula (IIb), in which $R_1$, $R_2$, $R_3$, $R_3'$, $R_4$, $R_4'$, $R_5$ and $R_6$ are as defined above and Y is the alkylcarbonyl, arylcarbonyl or heteroarylcarbonyl radical, with a Wittig-Horner reagent of formula (XIV) in which W is the $R_1$ radical and W' is a radical chosen from the cyano, $C(O)R_2$ or $C(O)OR_2$ radicals, in a way in every respect similar to that described in method A.

Method G:

The compounds of general formula (IIa) in which Y, $R_1$, $R_2$, $R_3$, $R_4$, $R_5$ and $R_6$ are as defined above can also be prepared by oxidation of a compound of formula (IXa):

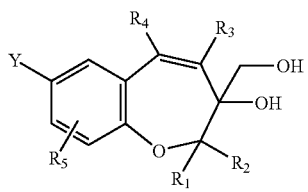

(IXa)

in which Y, $R_1$, $R_2$, $R_3$, $R_4$, $R_5$ and $R_6$ are as defined above, in a way in every respect similar to that described in method A for the oxidation of the compounds (IVa) to (IIIa).

The compounds of general formula (IXa) in which Y, $R_1$, $R_2$, $R_3$, $R_4$, $R_5$ and $R_6$ are as defined above can also be prepared by oxidation of the exocyclic double bond of a compound of formula (Xa):

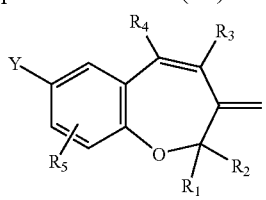

(Xa)

in which Y, $R_1$, $R_2$, $R_3$, $R_4$, $R_5$ and $R_6$ are as defined above, in a way in every respect similar to that described in method A for the oxidation of the compounds (Va) to (IVa).

The compounds of general formula (IIa) in which Y, $R_1$, $R_2/R_3$, $R_4$, $R_5$ and $R_6$ are as defined above can also be prepared by ozonolysis of the exocyclic double bond of a compound of formula (Xa) in which Y, $R_1$, $R_2$, $R_3$, $R_4$, $R_5$ and $R_6$ are as defined above, in a way in every respect similar to that described in method A for the ozonolysis of the compounds (Va) to (IIIa).

The compounds of general formula (Xa) in which Y, $R_1$, $R_2$, $R_3$, $R_4$, $R_5$ and $R_6$ are as defined above can also be prepared by cyclization of a compound of formula (XIa):

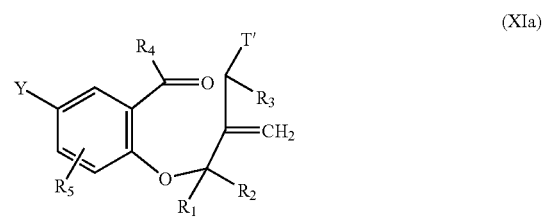

(XIa)

in which Y, $R_1$, $R_2$, $R_3$, $R_4$, $R_5$ and $R_6$ are as defined above, by the successive action of one or more equivalents of triphenylphosphine at reflux of the solvent and then addition of one or more equivalents of a base, such as alkali metal or alkaline earth metal alkoxides, preferably sodium ethoxide, sodium methoxide or potassium tert-butoxide, or alkali metal and alkaline earth metal hydrides, preferably sodium hydride or potassium hydride, or of an organometallic derivative, such as alkyllithium compounds, preferably butyllithium, alkylmagnesium halides or lithium diisopropylamide.

The appropriate solvent for this reaction can be an ether, such as diethyl ether, diisopropyl ether, tetrahydrofuran, dioxane or dimethoxyethane, a nitrile, such as acetonitrile, propionitrile or benzonitrile, or a dipolar aprotic solvent, such as dimethylformamide, dimethylacetamide, N-methylpyrrolidone, dimethylpropyleneurea or dimethyl sulfoxide. The reaction time depends on the conditions used and is generally between 0.1 and 48 h and is generally carried out at a temperature of between −80° C. and 180° C. (preferably between 0° C. and 100° C.) or at the boiling point of the solvent used. There is no absolute limit for the relative proportions of compound of formula (XIa) and of base. However, it is advantageous to choose a base/(XIa) molar ratio of between 0.1 and 100, preferably 1 to 5.

The compounds of general formula (XIa) in which Y, $R_1$, $R_2$, $R_3$, $R_4$, $R_5$ and $R_6$ are as defined above can also be prepared by condensation of a compound of formula (XIIa):

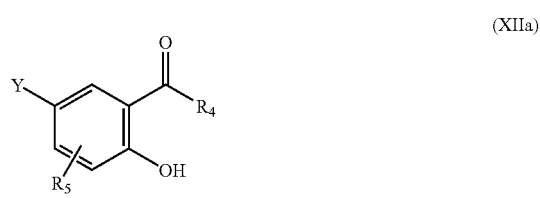

(XIIa)

in which Y, $R_4$, $R_5$ and $R_6$ are as defined above, with a compound of formula (VIIIa) in which $R_1$, $R_2$ and $R_3$ are as defined above and T and T' are, independently of one another, a halogen atom, preferably chlorine or bromine, by the action of one or more equivalents of a base, in a way identical in every respect similar to that described in method A for condensation of the compound (VII) with the compound (VIIIa).

The compounds of formula (XII) can be prepared according to a great many processes known to a person skilled in the art.

Method H:

The compounds of general formula (Ia) or of general formula (Ib) in which Y, $R_1$, $R_2$, $R_3$, $R_3'$, $R_4$, $R_4'$, $R_5$ and $R_6$ are as defined in the general formula and Z is the divalent radical chosen from the =$NR_1$, =$N(OR_1)$ or =$N(NR_1R_6)$ radicals can be prepared by reaction of a compound of formula (IIa) or of formula (IIb) in which Y, $R_1$, $R_2$, $R_3$, $R_3'$, $R_4$, $R_4'$, $R_5$ and $R_6$ are as defined above with respectively an amine of formula $NH_2$—$R_1$, a hydroxylamine of formula $NH_2$—$OR_1$ or a hydrazine of formula $NH_2$—$NR_1R_6$, for which $R_1$ and $R_6$ are as defined above, in the absence or in the presence of a solvent. The reaction is generally carried out at a temperature of between −80° C. and 180° C. (preferably between −20° C. and 20° C.) or at the boiling point of the solvent used. The appropriate solvent for this reaction can be a protic solvent, such as alcohols, in particular methanol, ethanol or propanol, or water. Mixtures of these various solvents can also be used. The reaction time depends on the conditions used and is generally between 0.1 and 48 h. There is no absolute limit for the relative proportions of compound of formula (IIa) or compound of formula (IIb) and of "amine". However, it is advantageous to choose an "amine"/(IIa) or "amine"/(IIb) molar ratio of between 0.1 and 50, preferably 1 to 5.

Method I:

The compounds of general formula (IIIa) in which Y, $R_1$, $R_2$, $R_3$, $R_5$ and $R_6$ are as defined above, Ar is a phenyl or toluyl radical and $R_4$ is chosen from the alkyl, arylalkyl or heteroarylalkyl radicals can be prepared by alkylation of a compound of general formula (IIIa) in which Y, $R_1$, $R_2$, $R_3$, $R_5$ and $R_6$ are as defined above, Ar is a phenyl or toluyl radical and $R_4$ is a hydrogen atom, with an alkyl halide, respectively arylalkyl halide or heteroarylalkyl halide, by the action of one or more equivalents of an organic or inorganic base, such as alkali metal and alkaline earth metal hydroxides, preferably sodium hydroxide, potassium hydroxide, cesium hydroxide or calcium hydroxide, alkali metal and alkaline earth metal alkoxides, such as potassium tert-butoxide, alkali metal and alkaline earth metal hydrides, such as sodium hydride, potassium hydride or cesium hydride, alkali metal and alkaline earth metal carbonates and bicarbonates, such as sodium carbonate, potassium carbonate, calcium carbonate, sodium bicarbonate, potassium bicarbonate or calcium bicarbonate, organic bases, preferably nitrogenous organic bases, such as pyridine, alkylpyridines, alkylamines, such as trimethylamine, triethylamine or diisopropylethylamine, or aza derivatives, such as 1,5-diazabicyclo[4.3.0]non-5-ene or 1,8-diazabicyclo[5.4.0]undec-7-ene, alkyllithium compounds, such as butyllithium, sec-butyllithium or tert-butyllithium, or alkali metal salts of nitrogenous bases optionally supported on a resin, such as lithium diisopropylamide, potassium diisopropylamide, lithium bis(trimethylsilyl)amide or potassium bis(trimethylsilyl)amide, in the presence of a catalytic amount or of one or more equivalents of hexamethylphosphoramide or of dimethylpropyleneurea. The reaction is generally carried out in the absence or in the presence of a solvent, at a temperature of between −80° C. and 180° C. (preferably between 0° C. and 150° C.) or at the boiling point of the solvent used. The appropriate solvent for this reaction can be an aliphatic hydrocarbon, such as pentane, hexane, heptane or octane, an aromatic hydrocarbon, such as benzene, toluene, xylenes or halobenzenes, an ether, such as diethyl ether, diisopropyl ether, tetrahydrofuran, dioxane or dimethoxyethane, a halogenated hydrocarbon, such as dichloromethane, chloroform, 1,2-dichloroethane or 1,1,1-trichloroethane, an ester, such as methyl acetate or ethyl acetate, a nitrile, such as acetonitrile, propionitrile or benzonitrile, a dipolar aprotic solvent, such as dimethylformamide, dimethylacetamide, N-methylpyrrolidone, dimethylpropyleneurea or dimethyl sulfoxide, or water. Mixtures of these various solvents can also be used. The reaction time depends on the conditions used and is generally between 0.1 and 48 h. There is no absolute limit for the relative proportions of compound of formula (IIIa), of halide and of base. However, it is advantageous to choose a base/(IIIa) molar ratio of between 0.1 and 100, preferably 1 to 5, and a halide/(IIIa) molar ratio of between 0.1 and 20, preferably 1 to 2.

Method J:

The compounds of general formula (IIIb) in which Y, $R_1$, $R_2$, $R_3$, $R_3'$, $R_5$ and $R_6$ are as defined above, Ar is a phenyl or a toluyl radical and $R_4$ is chosen from the alkyl, arylalkyl or heteroarylalkyl radicals can be prepared by alkylation of a compound of general formula (IIIb), in which Y, $R_1$, $R_2$, $R_3$, $R_3'$, $R_5$ and $R_6$ are as defined above, Ar is a phenyl or toluyl radical and $R_4$ is a hydrogen atom, with an alkyl halide, respectively arylalkyl halide or heteroarylalkyl halide, by the action of one or more equivalents of an organic or inorganic base, in a way identical in every respect similar to that described in method I.

Method K:

The compounds of general formula (Va) in which Y, $R_1$, $R_2$, $R_3$, $R_5$ and $R_6$ are as defined above, Ar is a phenyl or toluyl radical and $R_4$ is chosen from the alkyl, arylalkyl or heteroarylalkyl radicals can be prepared by alkylation of a compound of general formula (Va), in which Y, $R_1$, $R_2$, $R_3$, $R_5$ and $R_6$ are as defined above, Ar is a phenyl or toluyl radical and $R_4$ is a hydrogen atom, with an alkyl halide, respectively arylalkyl halide or heteroarylalkyl halide, by the action of one or more equivalents of an organic or inorganic base, in a way identical in every respect similar to that described in method I.

Method L:

The compounds of general formula (Vb) in which Y, $R_1$, $R_2$, $R_3$, $R_3'$, $R_5$ and $R_6$ are as defined above, Ar is a phenyl or toluyl radical and $R_4$ is chosen from the alkyl, arylalkyl or heteroarylalkyl radicals can be prepared by alkylation of a compound of general formula (Vb) in which Y, $R_1$, $R_2$, $R_3$, $R_5$ and $R_6$ are as defined above, Ar is a phenyl or toluyl radical and $R_4$ is a hydrogen atom, with an alkyl halide, respectively arylalkyl halide or heteroarylalkyl halide, by the action of one or more equivalents of an organic or inorganic base, in a way identical in every respect similar to that described in method I.

The various processes for the preparation of the compounds of the invention form an integral part of the invention, both in their entirety and for the stages taken individually and forming the various methods which have just been described.

The invention also relates to fungicidal compositions comprising an effective amount of at least one active material of formula (Ia) or (Ib). Thus, the fungicidal compositions according to the invention comprise a compound of formula (Ia) or (Ib) or one of their salts which are acceptable in agriculture or metal or semimetal complexes of these compounds, in combination with a solid or liquid carrier which is acceptable in agriculture and/or a surface-active agent, also acceptable in agriculture, and optionally one or more other fungicides, insecticides, herbicides, acaricides, attractants or pheromones and other compounds possessing biological activity. In particular, conventional inert carriers and conventional surface-active agents can be used.

Generally, the compositions according to the invention usually comprise from 0.05 to 99% (by weight) of active material, one or more solid or liquid carriers and, optionally, one or more surface-active agents.

Unless otherwise indicated, the percentages given in this description are percentages by weight.

These compositions cover not only compositions ready to be applied to the plant or seed to be treated by means of a suitable device, such as a spray device or dusting device, but also commercial concentrated compositions which have to be diluted before application to the crop or the reproduction material of said crop.

These fungicidal compositions according to the invention can also comprise any kind of other ingredient, such as, for example, protective colloids, adhesives, thickening agents, thixotropic agents, penetrating agents, stabilizing agents or sequestering agents. More generally, the active materials can be combined with any solid or liquid additive corresponding to conventional formulating techniques.

In the present account, the term "carrier" denotes an organic or inorganic and natural or synthetic material with which the active material is combined to facilitate its application to the parts of the plant or its reproduction materials or the soil in which they are growing or are capable of growing. This carrier is therefore generally inert and it must be acceptable in agriculture. The carrier can be solid (clays, natural or synthetic silicates, silica, resins, waxes, solid fertilizers, and the like) or liquid (water, alcohols, in particular butanol, and the like).

The surface-active agent can be an emulsifying, dispersing or wetting agent of ionic or nonionic type or a mixture of such surface-active agents. Mention may be made, for example, of salts of polyacrylic acids, salts of lignosulfonic acids, salts of phenolsulfonic or naphthalenesulfonic acids, polycondensates of ethylene oxide with fatty alcohols or with fatty acids or with fatty amines, substituted phenols (in particular alkylphenols or arylphenols), salts of esters of sulfosuccinic acids, taurine derivatives (in particular alkyltaurates), phosphoric esters of polyoxyethylenated phenols or alcohols, esters of fatty acids and of polyols, or the derivatives of the above compounds comprising sulfate, sulfonate and phosphate functional groups. The presence of at least one surface-active agent is generally indispensable when the active material and/or the inert carrier are not soluble in water and when the carrier agent for application is water.

The content of surface-active agent in the compositions according to the invention is advantageously between 5% and 40% by weight.

These compositions according to the invention are themselves in fairly diverse, solid or liquid forms.

The compounds of the invention can also be mixed with one or more compounds which are insecticides, fungicides, bactericides, acaricides, arthropodicides, nematocides, attractants or pheromones or other compounds possessing biological activity. The mixtures thus obtained have an activity with a broadened spectrum.

The mixtures with other fungicidal compounds are particularly advantageous, in particular the mixtures with acibenzolar-S-methyl, benalaxyl, benomyl, blasticidin-S, bromuconazole, captafol, captan, carbendazim, carboxin, carpropamid, chlorothalonil, copper-based fungicidal compositions, copper derivatives, such as copper hydroxide and copper oxychloride, cyazofamid, cymoxanil, cyproconazole, cyprodinil, dichloran, diclocymet, diethofencarb, difenoconazole, diflumetorim, dimethomorph, diniconazole, dodemorph, dodine, edifenphos, epoxiconazole, ethaboxam, ethirimol, famoxadone, fenamidone, fenarimol, fenbuconazole, fenhexamid, fenpiclonil, fenpropidin, fenpropimorph, ferimzone, fluazinam, fludioxonil, flumetover, fluquinconazole, flusilazole, flusulfamide, flutolanil, flutriafol, folpel, furalaxyl, furametpyr, guazatine, hexaconazole, hymexazol, imazalil, iprobenfos, iprodione, iprovalicarb, isoprothiolane, kasugamycin, mancozeb, maneb, mefenoxam, mepanipyrim, metalaxyl and its enantiomeric forms, such as metalaxyl-M, metconazole, metiram-zinc, oxadixyl, pefurazoate, penconazole, pencycuron, phosphorous acid and its derivatives, such as fosetyl-Al, phthalide, probenazole, prochloraz, procymidone, propamocarb, propiconazole, prothioconazole, pyrimethanil, pyroquilon, quinoxyfen, silthiofam, simeconazole, spiroxamine, tebuconazole, tetraconazole, thiabendazole, thifluzamide, thiophanate, for example thiophanate-methyl, thiram, triadimefon, triadimenol, triazolopyrimidines, for example cloransulam-methyl, flumetsulam, florasulam or metosulam, tricyclazole, tridemorph, triticonazole, valinamide derivatives, such as, for example, iprovalicarb and benthiavalicarb, vinclozolin, zineb and zoxamide, and fungicides of the strobilurin family, such as, for example, azoxystrobin, fluoxastrobin, kresoxim-methyl, metominostrobin, discostrobin, dimoxystrobin, picoxystrobin, pyraclostrobin and trifloxystrobin.

It has been discovered, entirely surprisingly, that the compounds of formula (Ia) or (Ib) according to the invention are fungicidal compounds which are active with regard to a very broad range of phytopathogenic fungi on crops. This activity has been revealed during preventive treatments but also during curative treatments. Furthermore, this activity has been shown to be very advantageous, even when low doses of compounds of formula (Ia) or (Ib) are employed.

In an entirely surprising way for compounds possessing such an activity (broad spectrum of action and low doses employed), these compounds of formula (Ia) or (Ib) are not phytotoxic or are very slightly phytotoxic, that is to say that they have a very good selectivity with regard to the plants treated.

Finally, the compounds of formula (Ia) or (Ib) have a very favorable behavior with regard to the environment, in the sense that they are not ecotoxic or are very slightly ecotoxic.

Thus, another subject matter of the invention is a process for curatively or preventively combating phytopathogenic fungi on crops, characterized in that the seeds, the leaves or the stems of plants or the soils in which these plants are growing or are capable of growing are treated, by application, spraying or injection, with an effective (agronomically effective) and nonphytotoxic amount of an active material of formula (Ia) or (Ib) or one of their salts which are acceptable in agriculture or a metal or semimetal complex of this compound, also acceptable in agriculture, preferably in the form of a fungicidal composition according to the invention.

The term "effective and nonphytotoxic amount" is understood to mean an amount of composition according to the invention which is sufficient to make it possible to control or destroy the fungi present or capable of appearing on the crops and which does not result, for said crops, in any significant symptom of phytotoxicity. Such an amount is capable of varying within wide limits according to the fungi to be combated, the type of crop, the weather conditions and the compounds included in the fungicidal composition according to the invention. This amount can be determined by systematic tests in the field within the scope of a person skilled in the art.

The compositions according to the invention are also of use in treating seeds, for example of cereals (wheat, rye, triticale and barley, in particular), of potato, of cotton, of pea, of rape, of corn, of flax or seeds of forest trees (in particular conifers). The application techniques are well known to a person skilled in the art and they can be used without disadvantage in the context of the present invention. Mention may be made, for example, of coating, including film coating.

Generally, the dose of composition applied is advantageously such that the dose of active material is between 2 g and 200 g of active material per 100 kg of seed, preferably between 3 g and 150 g per 100 kg in the case of seed treatments.

In the case of plant treatments, doses of 10 g/ha to 1 000 g/ha, preferably 50 g/ha to 300 g/ha, are generally applied in leaf treatment. It should be understood that these doses are given purely by way of illustration for the requirements of the present invention.

Thus, a person skilled in the art will be able to evaluate the precise doses of active materials to be applied according to the nature and the degree of development of the crops, according to the nature of the diseases to be eradicated and their stage of infestation, and according to the edaphic and weather conditions present on the ground at the time of or before or after the treatment or treatments.

Likewise, the number and the frequency of the treatments can vary according to the same criteria mentioned above. Thus, a person skilled in the art will think it advisable to carry out one or more treatments preventively, that is to say before the appearance of the diseases, optionally in combination with one or more curative treatments intended to eradicate the diseases which have already appeared.

Finally, the invention relates to a method for preventively or curatively protecting plant propagation materials, and plants resulting therefrom, from fungal attacks, characterized in that said materials are covered with an effective and nonphytotoxic dose of a composition according to the invention.

Mention may be made, among the plant propagation materials affected, in particular of seeds and tubors.

As was indicated above, the methods for covering the plant propagation materials, in particular seeds, are well known in the art and involve in particular coating, including film coating, techniques.

Mention may be made, among the plants targeted by the method according to the invention, of, as nonlimiting examples:

wheat, as regards combating the following diseases of seeds: *fusarium* diseases (*Microdochium nivale* and *Fusarium roseum*), bunts (*Tilletia caries, Tilletia controversa* or *Tilletia indica*), *septoria* disease (*Septoria nodorum*) or loose smut (*Ustilago tritici*);

wheat, as regards combating the following diseases of the aerial parts of the plant: cereal eyespot (*Tapesia yallundae, Tapesia acuformis*), take-all (*Gaeumannomyces graminis*), foot rot (*F. culmorum, F. graminearum*), ear blight (*F. culmorum, F. graminearum, Microdochium nivale*), sharp eyespot (*Rhizoctonia cerealis*), powdery mildew (*Erysiphe graminis form a specie tritici*), rusts (*Puccinia striiformis* and *Puccinia recondita*) and *septoria* diseases (*Septoria tritici* and *Septoria nodorum*), or tan spot (*Drechslera tritici-repentis*);

wheat and barley, as regards combating bacterial and viral diseases, for example barley yellow dwarf virus;

barley, as regards combating the following diseases of the seeds: leaf stripe (*Pyrenophora graminea*), net blotch (*Pyrenophora teres*), spot blotch (*Cochliobolus sativus*), loose smut (*Ustilago nuda*) and *fusarium* diseases (*Microdochium nivale* and *Fusarium roseum*);

barley, as regards combating the following diseases of the aerial parts of the plant: eyespot (*Tapesia yallundae*), net blotch (*Pyrenophora teres*), spot blotch (*Cochliobolus sativus*), powdery mildew (*Erysiphe graminis forma specie hordei*), leaf rust (*Puccinia hordei*) and scald (*Rhynchosporium secalis*);

potato, as regards combating diseases of the tubor (in particular *Helminthosporium solani, Phoma tuberosa, Rhizoctonia solani* or *Fusarium solani*), late blight (*Phytopthora infestans*) and some viroses (virus Y);

potato, as regards combating the following diseases of the foliage: early blight (*Alternaria solani*) or late blight (*Phytophthora infestans*);

cotton, as regards combating the following diseases of the young plants resulting from the seeds: damping-off and collar rot (*Rhizoctonia solani, Fusarium oxysporum*) or black root rot (*Thielaviopsis basicola*);

protein-yielding crops, for example the pea, as regards combating the following diseases of the seeds: anthracnose (*Ascochyta pisi, Mycosphaerella pinodes*), *fusarium* disease (*Fusarium oxysporum*), grey mold (*Botrytis cinerea*) or downy mildew (*Peronospora pisi*);

oleaginous crops, for example rape, as regards combating the following diseases of the seeds: *Phoma lingam, Alternaria brassicae, Sclerotinia sclerotiorum;* corn, as regards combating the diseases of the seeds: (*Rhizopus* sp., *Penicillium* sp., *Trichoderma* sp., *Aspergillus* sp. and *Gibberella fujikuroi*);

flax, as regards combating the disease of the seeds: *Alternaria linicola;* forest trees, as regards combating damping-off (*Fusarium oxysporum, Rhizoctonia solani*);

rice, as regards combating the following diseases of the aerial parts: rice blast (*Magnaporthe grisea*) or sheath blight (*Rhizoctonia solani*);

vegetable crops, as regards combating the following diseases of the seedlings or young plantlets resulting from seeds: damping-off and collar rot (*Fusarium oxysporum, Fusarium roseum, Rhizoctonia solani, Pythium* sp.);

vegetable crops, as regards combating the following diseases of the aerial parts: gray mold (*Botrytis* sp.), powdery mildews (in particular *Erysiphe cichoracearum*, *Sphaerotheca fuliginea*, *Leveillula taurica*), fusarium diseases (*Fusarium oxysporum*, *Fusarium roseum*), cladosporium diseases (*Cladosporium* sp.), alternaria diseases (*Alternaria* sp.), anthracnose (*Colletotrichum* sp.), septoria diseases (*Septoria* sp.), diseases caused by *Rhizoctonia solani*, or downy mildews (for example, *Bremia lactucae*, *Perosonospora* sp., *Pseudoperonospora* sp, *Phytophthora* sp.);

fruit trees, as regards the diseases of the aerial parts: brown rot (*Monilia fructigena*), scab (*Venturia inaequalis*) or powdery mildew (*Podosphaera leucotricha*);

the vine, as regards the diseases of the foliage: in particular gray mold (*Botrytis cinerea*), powdery mildew (*Uncinula necator*), black rot (*Guignardia biwelli*) or downy mildew (*Plasmopara viticola*);

beetroot, as regards the following diseases of the aerial parts: *Cercospora* leaf spot (*Cercospora beticola*), powdery mildew (*Erysiphe beticola*) or *Ramularia* leaf spot (*Ramularia beticola*).

The present invention also relates to the treatment of genetically modified plants with the compounds according to the invention or the agrochemical compositions according to the invention. Genetically modified plants are plants which have had incorporated in a stable way, in their genomes, a heterologous gene encoding an advantageous protein.

The term "heterologous gene encoding an advantageous protein" is understood to essentially mean according to the invention the genes which confer, on the transformed plant, novel agronomic properties or the genes for improving the agronomic quality of the transformed plant.

The present invention relates more particularly to the treatment of genetically modified plants comprising a heterologous gene which confers, on the plant, properties of resistance to diseases. Preferably, the heterologous gene confers, on the genetically modified plant, a spectrum of activity complementary to the spectrum of activity of the compounds according to the invention.

The term "complementary spectrum" is understood to mean, according to the invention, a spectrum of activity for the heterologous gene distinct from the spectrum of activity of the compounds according to the invention, or a spectrum of activity relating to identical infectious agents but allowing identical or improved control for lower applicational doses of compounds according to the invention.

The following preparation examples illustrate a few preparation processes. It is clearly understood that the processes which follow can be directly adapted to the synthesis of all the compounds of the present invention.

EXAMPLE 1

Preparation of methyl 3-methylene-5-(phenylsulfonyl)-2,3,4,5-tetrahydro-1-benzoxepin-7-carboxylate Stage 1:

Preparation of methyl 4-{[2-(chloromethyl)-2-propenyl]oxy}-3-[(phenylsulfonyl)methyl]benzoate 3 g (8.62 mmol) of tetrabutylammonium iodide, 3.02 g (20.4 mmol) of potassium carbonate and then 2.36 ml (20.4 mmol) of 2-chloromethyl-3-chloro-1-propene are successively introduced into a solution of 2.5 g (8.16 mmol) of readily accessible 1-{4-hydroxy-3-[(phenylsulfonyl)methyl]phenyl}ethanone in 150 ml of N,N-dimethylformamide. The solution is stirred at ambient temperature for 20 hours and then water, ether and 1N hydrochloric acid are added, the reaction medium being cooled to 0° C. using a water bath and ice. The solid obtained by filtration is discarded, the phases are separated by settling and then the aqueous phase is extracted several times with ether. The combined organic phases are washed several times with an aqueous solution and then with brine. After drying and concentration under vacuum, the crude reaction product is purified by chromatography on silica gel (ethyl acetate/heptane 40/60) to provide 1.63 g (50%) of methyl 4-{[2-(chloromethyl)-2-propenyl]oxy}-3-[(phenyl-sulfonyl)methyl]benzoate in the form of a white solid; M.p.=92–93° C. (M.p. denotes the melting point of the compounds).

Stage 2:

Preparation of methyl 3-methylene-5-(phenylsulfonyl)-2,3,4,5-tetrahydro-1-benzoxepin-7-carboxylate 1.33 ml of 1.06M lithium bis(trimethylsilyl)amide in tetrahydrofuran are added to 478 mg (1.21 mmol) of methyl 4-{[2-(chloromethyl)-2-propenyl]oxy}-3-[(phenylsulfonyl)methyl]benzoate dissolved in 39 ml of tetrahydrofuran. The solution is stirred for 5 minutes and then water, 1N hydrochloric acid and dichloromethane are added to the reaction medium. After separating, the aqueous phase is extracted three times with dichloromethane. The combined organic phases are washed with brine, dried and then concentrated under vacuum. The crude reaction product is purified by chromatography on silica gel (ethyl acetate/heptane 40/60) to provide 259 mg (60%) of methyl 3-methylene-5-(phenylsulfonyl)-2,3,4,5-tetrahydro-1-benzoxepin-7-carboxylate in the form of a white solid; $^1$H NMR (300 MHz, CDCl$_3$): 2.98 (dd, J=13.9 and 7.1 Hz, 1H), 3.21 (dd, J=13.9 and 7.1 Hz, 1H), 3.86 (s, 3H), 4.20 (d, J=13.4 Hz, 1H), 4.45 (t, J=7.35 Hz, 1H), 4.73 (d, J=13.4 Hz, 1H), 4.99 (s, 1H), 5.09 (s, 1H), 6.98 (d, J=8.28 Hz, 1H), 7.43 (m, 2H), 7.62 (m, 3H), 7.76 (d, J=2.07 Hz, 1H), 7.94 (dd, J=8.46 and 2 Hz, 1H).

EXAMPLE 2

Preparation of methyl 3-oxo-5-(phenylsulfonyl)-2,3,4,5-tetrahydro-1-benzoxepin-7-carboxylate 259 mg (0.72 mol) of methyl 3-methylene-5-(phenylsulfonyl)-2,3,4,5-tetrahydro-1-benzoxepin-7-carboxylate, prepared according to example 1, in solution of 20 ml of dichloromethane, are introduced into a 50 ml three-necked flask. An ozone/oxygen mixture is bubbled in at −78° C. When the color of the reaction medium becomes purple-blue, oxygen is bubbled in in order to purge the excess ozone and then an excess of dimethyl sulfide (2 ml) is added when the solution again becomes colorless. The reaction medium is stirred at ambient temperature for 14 hours and then water is added. A 1N hydrochloric acid solution is added in order to obtain a pH of 2, the phases are separated by settling and the aqueous phase is extracted three times with dichloromethane. The combined organic phases are washed twice using a solution of pH=2, are then dried and are finally concentrated under vacuum. 259 mg (99%) of methyl 3-oxo-5-(phenylsulfonyl)-2,3,4,5-tetrahydro-1-benzoxepin-7-carboxylate are obtained without additional purification in the form of a white solid; M.p.=128–130° C.

EXAMPLE 3

Preparation of methyl 3-methylene-2,3,4,5-tetrahydro-1-benzoxepin-7-carboxylate 728 mg (0.95 mmol) of 3% sodium amalgam are added portionwise at 0° C. to a suspension of 85 mg (0.23 mmol) of methyl 3-methylene-5-(phenylsulfonyl)-2,3,4,5-tetrahydro-1-benzoxepin-7-carboxylate, prepared according to example 1, and of 116 mg (0.95 mmol) of sodium hydrogenphosphate in 10 ml of a 1/1 methanol/tetrahydrofuran binary mixture. The reaction medium is subsequently stirred at ambient temperature for 4 hours. After addition of water and dichloromethane and filtering off the mercury, the phases are separated and the aqueous phase is extracted 3 times with dichloromethane. The combined organic phases are washed with a slightly acidic aqueous solution and then with brine. After drying and then concentrating under vacuum, 49 mg (98%) of methyl 3-methylene-2,3,4,5-tetrahydro-1-benzoxepin-7-carboxylate are obtained without additional purification in the form of an oil; $^1$H NMR (300 MHz, CDCl$_3$): 2.53. (m, 2H), 2.93 (m, 2H), 3.89 (s, 3H), 4.49 (s, 2H), 5.0 (d, J=4.1 Hz, 2H), 7.0 (d, J=8.1 Hz, 1H), 7.86 (m, 2H).

EXAMPLE 4

Preparation of methyl 3-oxo-2,3,4,5-tetrahydro-1-benzoxepin-7-carboxylate

In a way identical to example 2, 49 mg (97%) of methyl 3-oxo-2,3,4,5-tetrahydro-1-benzoxepin-7-carboxylate are obtained, in the form of an oil, from 50 mg of methyl 3-methylene-2,3,4,5-tetrahydro-1-benzoxepin-7-carboxylate, prepared according to example 3; $^1$H NMR (300 MHz, CDCl$_3$): 3.0 (m, 2H), 3.14 (m, 2H), 3.9 (s, 3H), 4.55 (s, 2H), 7.0 (d, J=8.3 Hz, 1H), 7.86 (m, 2H).

EXAMPLE 5

Preparation of methyl 3-(chloromethylene)-2,3,4,5-tetrahydro-1-benzoxepin-7-carboxylate 0.08 ml (0.2 mmol) of a 1.9M solution of n-butyllithium in hexane is added dropwise to a suspension of 76 mg (0.22 mmol) of chloromethyltriphenylphosphonium chloride in 1.7 ml of tetrahydrofuran cooled to 0° C. The solution is stirred for one hour and then 40 mg (0.18 mmol) of methyl 3-oxo-2,3,4,5-tetrahydro-1-benzoxepin-7-carboxylate, prepared according to example 4, in 2.5 ml of tetrahydrofuran are added at 0° C. via a hollow tube. The solution is stirred at ambient temperature for 1 h 30 and then water is added. After concentrating the solution, dichloromethane is added. The phases are separated and then the aqueous phase is extracted with dichloromethane. The combined organic phases are then washed using brine, are then dried and are finally concentrated under vacuum. The crude reaction product is then purified by chromatography on silica gel (ethyl acetate/heptane 10/90) to provide 11 mg (24%) of methyl 3-(chloromethylene)-2,3,4,5-tetrahydro-1-benzoxepin-7-carboxylate in the form of a mixture of two isomers in a Z/E ratio (70/30); $^1$H NMR (300 MHz, CDCl$_3$): 2.6 (m, 2H), 2.99 (m, 2H), 3.9 (s, 3H), 4.79 (s, 2H), 6.07 (s, 1H), 7.04 (d, J=8.3 Hz, 1H), 7.84 (m, 2H).

EXAMPLE 6

Preparation of methyl 5-benzyl-3-methylene-5-(phenylsulfonyl)-2,3,4,5-tetrahydro-1-benzoxepin-7-carboxylate 0.072 ml (1.1 equivalents) of 1,3-dimethyl-3,4,5,6-tetrahydro-2(1H)-pyrimidinone and then 0.6 ml (1.1 equivalents) of 1.06M lithium bis(trimethylsilyl)amide in tetrahydrofuran are added at ambient temperature to 195 mg (0.55 mmol) of methyl 3-methylene-5-(phenylsulfonyl)-2,3,4,5-tetrahydro-1-benzoxepin-7-carboxylate, prepared according to example 1, in solution in 5 ml of tetrahydrofuran. The reaction medium then assumes a dark yellow color. After stirring for 15 minutes, 0.073 ml (1.1 equivalents) of benzyl bromide is added. After stirring for 5 minutes, water, 1N hydrochloric acid and dichloromethane are added. After separating the organic and aqueous phases, the aqueous phase is extracted three times with dichloromethane. The combined organic phases are washed with brine, are dried and are finally concentrated under vacuum. The crude reaction product is then purified by chromatography on silica gel (ethyl acetate/heptane 25/75) to provide 211 mg (86%) of methyl 5-benzyl-3-methylene-5-(phenylsulfonyl)-2,3,4,5-tetrahydro-1-benzoxepin-7-carboxylate in the form of a white solid; M.p.=164–165° C.

EXAMPLE 7

Preparation of methyl 5-benzyl-3-oxo-5-(phenylsulfonyl)-2,3,4,5-tetrahydro-1-benzoxepin-7-carboxylate In a way identical to example 2, 72 mg (99%) of methyl 5-benzyl-3-oxo-5-(phenylsulfonyl)-2,3,4,5-tetrahydro-1-benzoxepin-7-carboxylate are obtained, in the form of a yellow-white solid, from 75 mg (0.16 mmol) of methyl 5-benzyl-3-methylene-5-(phenylsulfonyl)-2,3,4,5-tetrahydro-1-benzoxepin-7-carboxylate, prepared according to example 6; M.p.=181–185° C.

EXAMPLE 8

Preparation of methyl 5-benzyl-3-methylene-2,3,4,5-tetrahydro-1-benzoxepin-7-carboxylate In a way identical to example 3, 70 mg (82%) of methyl 5-benzyl-3-methylene-2,3,4,5-tetrahydro-1-benzoxepin-7-carboxylate are obtained, in the form of an oil, after purification on silica gel (ethyl acetate/heptane 20/80), from 126 mg (0.28 mmol) of methyl 5-benzyl-3-methylene-5-(phenylsulfonyl)-2,3,4,5-tetrahydro-1-benzoxepin-7-carboxylate, prepared according to example 6; percentage analysis: calculated C 77.90%; H 6.54%; found C 77.91%; H 6.47%.

EXAMPLE 9

Preparation of methyl 5-benzyl-3-oxo-2,3,4,5-tetrahydro-1-benzoxepin-7-carboxylate In a way identical to example 2, 35 mg (99%) of methyl 5-benzyl-3-oxo-2,3,4,5-tetrahydro-1-benzoxepin-7-carboxylate are obtained, in the form of an oil, from 35 mg (0.11 mmol) of methyl 5-benzyl-3-methylene-2,3,4,5-tetrahydro-1-benzoxepin-7-carboxylate, prepared according to example 8; $^1$H NMR (300 MHz, CDCl$_3$): 3 (m, 4H), 3.44 (m, 1H), 3.9 (s, 3H), 4.43 (s, 1H), 7.1 (m, 3H), 7.3 (m, 3H), 7.91 (m, 2H).

EXAMPLE 10

Preparation of methyl 5-benzyl-3-(chloromethylene)-2,3,4,5-tetrahydro-1-benzoxepin-7-carboxylate 1.1 equivalents of n-butyllithium are added to a suspension of 40 mg (0.12 mmol) of chloromethyltriphenylphosphonium chloride in 3 ml of tetrahydrofuran cooled to 0° C. After stirring for one hour, the ylide is added at 0° C. via a hollow tube to 30 mg (0.1 mmol) of methyl 5-benzyl-3-oxo-2,3,4,5-tetrahydro-1-benzoxepin-7-carboxylate, prepared according to example 9. After stirring at ambient temperature for 30 minutes, water, 1N hydrochloric acid and dichloromethane are added. The phases are separated by settling and then the aqueous phase is extracted three times with dichloromethane. The combined organic phases are washed with brine, are then dried and are finally concentrated under vacuum. The crude reaction product is then purified by chromatography on silica gel (ethyl acetate/heptane 5/95) to provide 18 mg (53%) of methyl 5-benzyl-3-(chloromethylene)-2,3,4,5-tetrahydro-1-benzoxepin-7-carboxylate in the form of a mixture of two isomers in a Z/E ratio (60/40); exact mass (CI): calculated 343.11009; found 343.11027.

EXAMPLE 11

Preparation of methyl 5-allyl-3-methylene-5-(phenylsulfonyl)-2,3,4,5-tetrahydro-1-benzoxepin-7-carboxylate 0.023 ml (1.1 equivalents) of 1,3-dimethylpropyleneurea and then 0.189 ml (1.1 equivalents) of 1.06M lithium bis(trimethylsilyl)amide in tetrahydrofuran are added at ambient temperature to 61 mg (0.17 mmol) of methyl 3-methylene-5-(phenylsulfonyl)-2,3,4,5-tetrahydro-1-benzoxepin-7-carboxylate, prepared according to example 1, in solution in 1.8 ml of tetrahydrofuran. The reaction medium then assumes a dark yellow color. After stirring for 15 minutes, 0.0165 ml (1.1 equivalents) of allyl bromide is added. After stirring for 5 minutes, water, 1N hydrochloric acid and dichloromethane are added. After separating the organic and aqueous phases, the aqueous phase is extracted three times with dichloromethane. The combined organic phases are washed with brine, are dried and are finally concentrated under vacuum. The crude reaction product is then purified by chromatography on silica gel (ethyl acetate/heptane 25/55) to give 51 mg (67%) of methyl 5-allyl-3-methylene-5-(phenylsulfonyl)-2,3,4,5-tetrahydro-1-benzoxepin-7-carboxylate in the form of an oil; $^1$H NMR (300 MHz, CDCl$_3$): 3.25 (m, 4H), 3.9 (s, 3H), 4.25 (d, J=14.3 Hz, 1H), 4.6 (d, J=14.3 Hz, 1H), 4.93 (s, 1H), 5.10 (s, 1H), 5.21 (m, 2H), 5.83 (m, 1H), 6.86 (d, J=8.5 Hz, 1H), 7.4 (m, 4H), 7.57 (m, 1H), 7.95 (dd, J=8.46 and 2 Hz, 1H), 8.21 (d, J=2.07 Hz, 1H).

EXAMPLE 12

Preparation of methyl 5-ethyl-3-methylene-5-(phenylsulfonyl)-2,3,4,5-tetrahydro-1-benzoxepin-7-carboxylate 0.030 ml (1.1 equivalents) of 1,3-dimethylpropyleneurea and then 0.246 ml (1.1 equivalents) of 1.06M lithium bis(trimethylsilyl)amide in tetrahydrofuran are added at ambient temperature to 80 mg (0.22 mmol) of methyl 3-methylene-5-(phenylsulfonyl)-2,3,4,5-tetrahydro-1-benzoxepin-7-carboxylate, prepared according to example 1, in solution in 2.2 ml of tetrahydrofuran. The reaction medium then assumes a dark yellow color. After stirring for 15 minutes, 0.0185 ml (1.1 equivalents) of ethyl bromide is added. After stirring for 5 minutes, water, 1N hydrochloric acid and dichloromethane are added. After separating the organic and aqueous phases, the aqueous phase is extracted three times with dichloromethane. The combined organic phases are washed with brine, are dried and are finally concentrated under vacuum. The crude reaction product is then purified by chromatography on silica gel (ethyl acetate/heptane 25/75) to give 56 mg (58%) of methyl 5-ethyl-3-methylene-5-(phenylsulfonyl)-2,3,4,5-tetrahydro-1-benzoxepin-7-carboxylate in the form of an oil; $^1$H NMR (300 MHz, CDCl$_3$): 0.97 (t, J=7.3 Hz, 3H), 2.41 (q, J=7.3 Hz, 2H), 3.83 (s, 3H), 4.28 (d, J=14.7 Hz, 1H), 4.58 (d, J=14.7 Hz, 1H), 4.86 (s, 1H), 5.02 (s, 1H), 6.82 (d, J=8.5 Hz, 1H), 7.35 (m, 5H), 7.85 (dd, J=8.46 and 2 Hz, 1H), 8.08 (d, J=2.07 Hz, 1H).

EXAMPLE 13

Preparation of 1-[3-methylene-5-(phenylsulfonyl)-2,3,4,5-tetrahydro-1-benzoxepin-7-yl]ethanone Stage 1:

Preparation of 1-{4-{[2-(chloromethyl)-2-propenyl]oxy}-3-[(phenylsulfonyl)methyl]ethanone 3.18 g (21.5 mmol) of tetrabutylammonium iodide, 3.02 g (21.5 mmol) of potassium carbonate and then 2.6 ml (21.5 mmol) of 2-chloromethyl-3-chloro-1-propene are successively introduced into 2.5 g (8.62 mmol) of 1-{4-hydroxy-3-[(phenylsulfonyl)methyl]phenyl}ethanone in solution in 150 ml of N,N-dimethylformamide. The solution is stirred at ambient temperature for 20 hours and then water, ether and 1N hydrochloric acid are added, the reaction medium being cooled to 0° C. using a water bath and ice. The precipitate obtained is filtered off and then discarded. The phases are separated by settling and then the aqueous phase is extracted several times with ether. The combined organic phases are washed several times with an aqueous solution of pH=2 and then with brine. After drying and concentrating under vacuum, the crude reaction product is purified by chromatography on silica gel (ethyl acetate/heptane 40/60) to give 1.75 g (53%) of 1-{4-{[2-(chloromethyl)-2-propenyl]oxy}-3-[(phenylsulfonyl)methyl]ethanone in the form of a white solid; M.p.=95–96° C.

Stage 2:

Preparation of 1-[3-methylene-5-(phenylsulfonyl)-2,3,4,5-tetrahydro-1-benzoxepin-7-yl]ethanone 3.56 ml (2 equivalents) of 1.06M lithium bis(trimethylsilyl)amide in tetrahydrofuran are added to 675 mg (1.78 mmol) of 1-{4-{[2-(chloromethyl)-2-propenyl]oxy}-3-[(phenylsulfonyl)methyl]ethanone in solution in 58 ml of tetrahydrofuran. The solution is stirred for 5 minutes and then water, 1N hydrochloric acid and dichloromethane are added. After separating, the aqueous phase is extracted three times with dichloromethane. The combined organic phases are washed with brine, are dried and are then concentrated under vacuum. The crude reaction product is purified by chromatography on silica gel (ethyl acetate/heptane 35/65) to provide 388 mg (63%) of 1-[3-methylene-5-(phenylsulfonyl)-2,3,4,5-tetrahydro-1-benzoxepin-7-yl]ethanone in the form of a white solid; M.p.=124–125° C.

EXAMPLE 14

Preparation of 7-acetyl-5-(phenylsulfonyl)-4,5-dihydro-1-benzoxepin-3(2H)-one

In a way identical to example 2, 35 mg (98%) of 7-acetyl-5-(phenylsulfonyl)-4,5-dihydro-1-benzoxepin-3(2H)-one are obtained, in the form of a white solid, from 60 mg (0.17 mmol) of 1-[3-methylene-5-(phenylsulfonyl)-2,3,4,5-tetrahydro-1-benzoxepin-7-yl]ethanone, prepared according to example 13; M.p.=167–168° C.

EXAMPLE 15

Preparation of 1-(3-methylene-2,3,4,5-tetrahydro-1-benzoxepin-7-yl)ethanol 3.14 mg (6.82 mmol) of 5% sodium amalgam are added portionwise at 0° C. to 389 mg (1.14 mmol) of 1-[3-methylene-5-(phenylsulfonyl)-2,3,4,5-tetrahydro-1-benzoxepin-7-yl]ethanone, prepared according to example 13, and 648 mg (4.55 mmol) of sodium hydrogenphosphate in suspension in 50 ml of a 1/1 methanol/tetrahydrofuran binary mixture. The reaction medium is subsequently stirred at ambient temperature for 4 hours. After addition of water and of dichloromethane and filtering off the mercury, the phases are separated and the aqueous phase is extracted three times with dichloromethane. The combined organic phases are washed with a slightly acidic aqueous solution and then with brine. Purification on silica gel (ethyl acetate/heptane 30/70) makes it possible to obtain 188 mg of 1-(3-methylene-2,3,4,5-tetrahydro-1-benzoxepin-7-yl)ethanol as a mixture with its pinacol dimer.

EXAMPLE 16

Preparation of 7-acetyl-4,5-dihydro-1-benzoxepin-3(2H)-one 4.7 mg (0.023 mmol) of ruthenium chloride trihydrate are added at 0° C. to 188 mg of 1-(3-methylene-2,3,4,5-tetrahydro-1-benzoxepin-7-yl)ethanol as a mixture with its pinacol dimer, prepared according to example 15, and 1.28 g (5.99 mmol) of sodium periodate in solution in a carbon tetrachloride/acetonitrile/water (2/2/3) ternary mixture. After stirring at ambient temperature for 24 hours, a saturated sodium thiosulfate solution and dichloromethane are added. After separating the phases, the aqueous phase is extracted 3 times with dichloromethane. The combined organic phases are washed with brine, are then dried and are finally concentrated under vacuum. Rapid filtration through silica gel (ethyl acetate/heptane 30/70) provides 87 mg (55%) of 7-acetyl-4,5-dihydro-1-benzoxepin-3(2H)-one in the form of a white solid; M.p.=80–82° C.

EXAMPLE 17

Preparation of 1-[3-(chloromethylene)-2,3,4,5-tetrahydro-1-benzoxepin-7-yl]ethanone In a way identical to example 10, 49 mg (71%) of 1-[3-(chloromethylene)-2,3,4,5-tetrahydro-1-benzoxepin-7-yl]ethanone are obtained, in the form of a mixture of Z/E isomers (65/35), after purification by chromatography on silica gel (ethyl acetate/heptane 15/85), from 49 mg (0.24 mmol) of 7-acetyl-4,5-dihydro-1-benzoxepin-3(2H)-one, prepared according to example 16; $^1$H NMR (300 MHz, CDCl$_3$): 2.57 (s, 3H), 2.59 (m, 2H), 2.98 (m, 2H), 4.8 (s, 2H), 6.07 (s, 1H), 7.05 (d, J=8.3 Hz, 1H), 7.76 (m, 2H).

EXAMPLE 18

Preparation of 1-[5-benzyl-3-methylene-5-(phenylsulfonyl)-2,3,4,5-tetrahydro-1-benzoxepin-7-yl]ethanone 0.152 ml (2.2 equivalents) of 1,3-dimethylpropyleneurea and then 1.286 ml (2.2 equivalents) of 1.06M lithium bis(trimethylsilyl)amide in tetrahydrofuran are added at ambient temperature to 200 mg (0.58 mmol) of 1-[3-methylene-5-(phenylsulfonyl)-2,3,4,5-tetrahydro-1-benzoxepin-7-yl]ethanone, prepared according to example 13, in solution in 5.8 ml of tetrahydrofuran. The reaction medium then assumes a dark yellow color. After 15 minutes, 0.0698 ml (1 equivalent) of benzyl bromide is added. Water is immediately added, and 1N hydrochloric acid and dichloromethane. After separating the organic and aqueous phases, the aqueous phase is extracted 3 times with dichloromethane. The combined organic phases are washed with brine, are dried and are finally concentrated under vacuum. The crude reaction product is purified by chromatography on silica gel (ethyl acetate/heptane 30/70) to provide 245 mg (97%) of 1-[5-benzyl-3-methylene-5-(phenylsulfonyl)-2,3,4,5-tetrahydro-1-benzoxepin-7-yl]ethanone in the form of a white solid; M.p.=131–132° C.

EXAMPLE 19

Preparation of 1-[5-benzyl-3-methylene-5-(phenylsulfonyl)-2,3,4,5-tetrahydro-1-benzoxepin-7-yl]ethanone 3.17 ml (2 equivalents) of 1.06M lithium bis(trimethylsilyl)amide in tetrahydrofuran are added at ambient temperature to 600 mg (1.59 mmol) of 1-{4-{[2-(chloromethyl)-2-propenyl]oxy}-3-[(phenylsulfonyl)-methyl}ethanone, prepared according to stage 1 of example 13, in solution in tetrahydrofuran. After stirring at ambient temperature for 5 minutes, 0.383 ml (2.2 equivalents) of 1,3-dimethylpropyleneurea and then 1.587 ml (1 equivalent) of 1.06M sodium bis(trimethylsilyl)amide in tetrahydrofuran are added. The reaction medium is stirred for 10 minutes and then 0.188 ml (1.587 mmol) of benzyl bromide is added. Immediately afterwards, water, 1N hydrochloric acid and dichloromethane are added. After separating the organic and aqueous phases, the aqueous phase is extracted three times with dichloromethane. The combined organic phases are washed with brine, are dried and are finally concentrated under vacuum. The crude reaction product is then purified by chromatography on silica gel (ethyl acetate/heptane 30/70) to provide 366 mg (53%) of 1-[5-benzyl-3-methylene-5-(phenylsulfonyl)-2,3,4,5-tetrahydro-1-benzoxepin-7-yl]ethanone in the form of a white solid; M.p.=131–132° C.

EXAMPLE 20

Preparation of 7-acetyl-5-benzyl-5-(phenylsulfonyl)-4,5-dihydro-1-benzoxepin-3(2H)-one In a manner identical to example 2, 211 mg (98%) of 7-acetyl-5-benzyl-5-(phenylsulfonyl)-4,5-dihydro-1-benzoxepin-3(2H)-one are obtained, in the form of a white solid, from 215 mg (0.5 mmol) of 1-[5-benzyl-3-methylene-5-(phenylsulfonyl)-2,3,4,5-tetrahydro-1-benzoxepin-7-yl]ethanone, prepared according to example 18; M.p.=154–157° C.

EXAMPLE 21

Preparation of 7-acetyl-5-benzyl-4,5-dihydro-1-benzoxepin-3(2H)-one

In a way identical to examples 15 and 16, 112 mg (47%) of 7-acetyl-5-benzyl-4,5-dihydro-1-benzoxepin-3(2H)-one are obtained, in the form of a white solid, from 366 mg (0.85 mmol) of 1-[5-benzyl-3-methylene-5-(phenylsulfonyl)-2,3,4,5-tetrahydro-1-benzoxepin-7-yl]ethanone, prepared according to example 18; M.p.=82–83° C.

EXAMPLE 22

Preparation of 1-[5-benzyl-3-(chloromethylene)-2,3,4,5-tetrahydro-1-benzoxepin-7-yl]ethanone In a way identical to example 10, 68 mg (85%) of 1-[5-benzyl-3-(chloromethylene)-2,3,4,5-tetrahydro-1-benzoxepin-7-yl]ethanone are obtained, in the form of a mixture of Z/E isomers (65/35), after purification by chromatography on silica gel (ethyl acetate/heptane 15/85), from 75 mg (0.255 mmol) of 7-acetyl-5-benzyl-4,5-dihydro-1-benzoxepin-3(2H)-one, prepared according to example 21; $^1$H NMR (300 MHz, CDCl$_3$): 2.48 (s, 3H), 2.6 (m, 2H), 2.95 (m, 2H), 3.29 (m, 1H), 4.45 (d, J=14.7 Hz, 1H), 5.10 (d, J=14.7 Hz, 1H), 5.94 (s, 1H), 7.12 (m, 6H), 7.61 (d, J=2.07 Hz, 1H), 7.76 (m, 2H).

EXAMPLE 23

Preparation of 3-methylene-2,3-dihydro-1-benzoxepin

Stage 1:

Preparation of 2-{[2-(chloromethyl)-2-propenyl]oxy}benzaldehyde 45 g (0.3 mol) of sodium iodide, 16.5 (0.12 mol) of potassium carbonate and 17.36 ml (0.15 mol) of 3-chloro-2-chloromethyl-1-propene are added to 10.4 ml (0.1 mol) of 2-hydroxybenzaldehyde in solution in acetone. The mixture is left at reflux of the solvent for 12 hours and then the solvent is evaporated. The medium is diluted in ether and the organic phases are subsequently washed successively with a saturated sodium sulfite solution and with brine and are then dried over magnesium sulfate. Purification by chromatography on silica gel (ethyl ether/heptane 30/70) provides 21.1 g (70%) of 2-{[2-(chloromethyl)-2-propenyl]oxy}benzaldehyde; $^1$H NMR (300 MHz, CDCl$_3$): 10.46 (s, 1H), 7.82 (dd, J=8.4 and 2.4 Hz, 1H), 7.5 (dd, J=2.4 Hz and 8.4 Hz, 1H), 7.00 (m, 2H), 5.49 and 5.32 (2s, 2H), 4.78 (s, 2H), 4.01 (s, 2H).

Stage 2:

Preparation of 3-methylene-2,3-dihydro-1-benzoxepin 2.69 g (10.29 mmol) of triphenylphosphine are added to a solution of 2.83 g (9.36 mmol) of the preceding iodide in solution in acetonitrile. After refluxing for 12 hours, followed by cooling the medium, 1.67 ml (9.36 mmol) of sodium methoxide (30% in methanol) are introduced dropwise. The solution is heated at reflux for 1 hour. After the usual extracting and washing treatments, the crude product is purified by chromatography on silica gel (ethyl ether/heptane 10/90) to give 902 mg (61%) of 3-methylene-2,3-dihydro-1-benzoxepine; $^1$H NMR (300 MHz, CDCl$_3$): 7.25–7.20 (m, 2H), 7.15–7 (m, 2H), 6.49 (d, J=11.7 Hz, 1H), 6.38 (d, J=11.7 Hz, 1H), 5.25 and 5.08 (2s, 2H), 4.62 (s, 2H).

EXAMPLE 24

Preparation of 3-(hydroxymethyl)-2,3-dihydro-1-benzoxepin-3-ol 160 mg (1 mmol) of 3-methylene-2,3-dihydro-1-benzoxepin, prepared according to example 23, are added to a mixture of 250 mg (1 mmol) of osmium tetroxide and 95 mg (1 mmol) of methanesulfonamide dissolved in 10 ml of a 1/1 water/tert-butanol mixture. After 12 hours at ambient temperature, 1.5 g of sodium bisulfite are introduced and the medium is stirred for one hour. Extraction with dichloromethane and then purification (purification is carried out by chromatography on silica gel (dichloromethane/methanol: 95/5)) provides 192 mg (95%) of 3-(hydroxymethyl)-2,3-dihydro-1-benzoxepin-3-ol in the form of a white solid; $^1$H NMR (300 MHz, CDCl$_3$): 7.28–7.18 (m, 2H), 7.08–6.9 (m, 2H), 6.41 (d, J=12 Hz, 1H), 5.85 (d, J=11.2 Hz, 1H), 4.14 (d, J=11.7 Hz, 1H), 4.14 (d, J=11.7 Hz, 1H), 3.72–3.62 (m, 2H), 2.69 (broad s, 1H, OH), 2.28 (broad s, 1H, OH).

EXAMPLE 25

Preparation of 1-benzoxepin-3(2H)-one

4×28.5 mg (0.55 mmol) of sodium periodate are added in four equal portions over 30 minutes to 106 mg (0.55 mmol) of 3-(hydroxymethyl)-2,3-dihydro-1-benzoxepin-3-ol, prepared according to example 24, in solution in 3 ml of a 3/7 dioxane/water mixture. After stirring at ambient temperature for 2 hours, the medium is filtered through celite and the solid is discarded. After the usual extracting and washing treatments, purification by chromatography on silica gel (dichloromethane) provides 61 mg (70%) of 1-benzoxepin-3(2H)-one; $^1$H NMR (300 MHz, CDCl$_3$): 7.45–7.35 (m, 2H), 7.15–7.25 (m, 3H), 6.38 (d, J=8.7 Hz, 1H), 4.55 (s, 2H).

EXAMPLE 26

Preparation of 3-(chloromethylene)-2,3-dihydro-1-benzoxepin 1.1 eq. of n-butyllithium are added to 104 mg (0.3 mmol) of chloromethyltriphenylphosphonium chloride in solution in tetrahydrofuran cooled to 0° C. After stirring for one hour, 40 mg (0.25 mmol) of 1-benzoxepin-3(2H)-one, prepared according to example 25, are added at ambient temperature and the mixture is left for 1 hour. After the usual treatments and evaporating the solvent under reduced pressure, the crude reaction product is taken up in pentane in order to precipitate triphenylphosphine oxide, to give 25 mg (52%) of 3-(chloromethylene)-2,3-dihydro-1-benzoxepin in the form of two isomers as a Z/E mixture (90/10); $^1$H NMR (300 MHz, C$_6$D$_6$) 6.98–6.78 (m, 4H), 6.02 (d, J=11.8 Hz, 1H), 5.80 (d, J=11.8 Hz, 1H), 5.68 (s, 1H), 4.65 (4.06) (s, 2H).

EXAMPLE 27

Preparation of 7-acetyl-1-benzoxepin-3(2H)-one 0.084 ml (1.05 equivalents) of 1,8-diazabicyclo[5.4.0]undec-7-ene is added at ambient temperature, under nitrogen, to 184 mg (0.53 mmol) of 7-acetyl-5-(phenylsulfonyl)-4,5-dihydro-1-benzoxepin-3(2H)-one, prepared according to example 14, in suspension in 20 ml of dichloromethane. From the addition of the base, the medium becomes translucent and slightly yellow. After addition of water and 1N hydrochloric acid, the phases are separated by settling and then the aqueous phase is extracted three times with dichloromethane. The combined organic phases are washed with a saturated sodium hydrogencarbonate solution and then brine. After drying and then concentrating under vacuum, 90 mg (83%) of 7-acetyl-1-benzoxepin-3(2H)-one are obtained in the form of a white solid; M.p.=92–93° C.

EXAMPLE 28

Preparation of 1-[3-(chloromethylene)-2,3-dihydro-1-benzoxepin-7-yl]ethanone

In a way identical to example 10, 55 mg (82%) of 1-[3-(chloromethylene)-2,3-dihydro-1-benzoxepin-7-yl]ethanone are obtained, in the form of a yellow-white solid comprising two Z/E isomers as a mixture in an 80/20 ratio, after purification by chromatography on silica gel (ethyl acetate/heptane 10/90), from 58 mg (0.28 mol) of 7-acetyl-1-benzoxepin-3(2H)-one, prepared according to example 27; M.p.=85–90° C.

EXAMPLE 29

Preparation of 7-acetyl-5-benzyl-1-benzoxepin-3(2H)-one

In a way identical to example 27, 95 mg (81%) of 7-acetyl-5-benzyl-1-benzoxepin-3(2H)-one are obtained, in the form of a yellow-white solid, from 173 mg (0.398 mmol) of 7-acetyl-5-benzyl-5-(phenylsulfonyl)-4,5-dihydro-1-benzoxepin-3(2H)-one, prepared according to example 20; M.p.=97–98° C.

EXAMPLE 30

Preparation of 1-[5-benzyl-3-(chloromethylene)-2,3-dihydro-1-benzoxepin-7-yl]ethanone In a way identical to example 10, 45 mg (67%) of 1-(5-benzyl-3-(chloromethylene)-2,3-dihydro-1-benzoxepin-7-yl]ethanone are obtained, in the form of a yellow-white solid comprising two Z/E isomers as a mixture in an 80/20 ratio, after purification by chromatography on silica gel (ethyl acetate/heptane 5/95) from 7-acetyl-5-benzyl-5-(phenylsulfonyl)-4,5-dihydro-1-benzoxepin-3(2H)-one prepared according to example 29; M.p.=89–94° C.

EXAMPLE 31

Preparation of methyl 3-oxo-2,3-dihydro-1-benzoxepin-7-carboxylate 0.084 ml (1.05 equivalents) of 1,8-diazabicyclo[5.4.0]undec-7-ene is added at ambient temperature to 217 mg (0.6 mmol) of methyl 3-oxo-5-(phenylsulfonyl)-2,3,4,5-tetrahydro-1-benzoxepin-7-carboxylate, prepared according to example 2, in suspension in 20 ml of dichloromethane. From the addition of the base, the medium becomes translucent and slightly yellow. After addition of water and 1N hydrochloric acid, the phases are separated by settling and then the aqueous phase is extracted three times with dichloromethane. The combined organic phases are washed with a saturated sodium hydrogencarbonate solution and then with brine. After drying and then concentrating under vacuum, 90 mg (68%) of methyl 3-oxo-2,3-dihydro-1-benzoxepin-7-carboxylate are obtained in the form of a white solid; M.p.=89–93° C.

EXAMPLE 32

Preparation of methyl 3-(chloromethylene)-2,3-dihydro-1-benzoxepin-7-carboxylate 1.3 equivalents of n-butyllithium are added to a suspension of 122 mg (0.35 mmol) of chloromethyltriphenylphosphonium chloride in tetrahydrofuran cooled to 0° C. After stirring for one hour, the ylide is added at 0° C., via a hollow tube, to 55 mg (0.25 mmol) of methyl 3-oxo-2,3-dihydro-1-benzoxepin-7-carboxylate, prepared according to example 31. Immediately afterwards, water, 1N hydrochloric acid and dichloromethane are added. The phases are separated and then the aqueous phase is extracted three times with dichloromethane. The combined organic phases are washed with brine, are then dried and are finally concentrated under vacuum. The crude reaction product is then purified by chromatography on silica gel (ethyl acetate/heptane 5/95) to provide 61 mg (96%) of methyl 3-(chloromethylene)-2,3-dihydro-1-benzoxepin-7-carboxylate in the form of a yellow-white solid comprising two Z/E isomers as a mixture in an 85/15 ratio; M.p.=72–77° C.

EXAMPLE 33

Preparation of methyl 5-benzyl-3-oxo-2,3-dihydro-1-benzoxepin-7-carboxylate

In a way identical to example 27, 24.5 mg (77%) of methyl 5-benzyl-3-oxo-2,3-dihydro-1-benzoxepin-7-carboxylate are obtained, in the form of a white solid, from 47 mg (0.1 mmol) of methyl 5-benzyl-3-oxo-5-(phenylsulfonyl)-2,3,4,5-tetrahydro-1-benzoxepin-7-carboxylate, prepared according to example 7; $^1$H NMR (300 MHz, CDCl$_3$): 3.9 (s, 3H), 4.05 (s, 2H), 4.57 (s, 2H), 6.35 (s, 1H), 7.24 (m, 6H), 7.98 (dd, J=8.5 and J=2.25 Hz, 1H), 8.33 (d, J=2.07 Hz, 1H).

EXAMPLE 34

Preparation of methyl 5-benzyl-3-(chloromethylene)-2,3-dihydro-1-benzoxepin-7-carboxylate In a way identical to example 10, 33 mg (60%) of methyl 5-benzyl-3-(chloromethylene)-2,3-dihydro-1-benzoxepin-7-carboxylate are obtained, in the form of a mixture of two Z/E isomers (80/20), after purification by chromatography on silica gel (ethyl acetate/heptane 5/95), from 50 mg (0.162 mmol) of methyl 5-benzyl-3-oxo-2,3-dihydro-1-benzoxepin-7-carboxylate, prepared according to example 33; exact mass (IC): calculated 341.09444; found 341.09452.

EXAMPLE 35

Preparation of methyl 3-methylene-2,3-dihydro-1-benzoxepin-7-carboxylate

Stage 1:

Preparation of methyl 3-formyl-4-hydroxybenzoate 24 ml of trifluoroacetic acid are added at 0° C. to a mixture of 4.56 g (30 mmol) of methyl 1-hydroxybenzoate and 8.64 g (60 mmol) of hexamethylenetetramine. The solution is brought to reflux and is stirred for 2 hours. After cooling, the solution is diluted with water to 50 ml. The solution is stirred overnight at ambient temperature and is then extracted with ether. The combined organic phases are then washed with water and then with brine. After drying over sodium sulfate and concentrating under vacuum, the crude reaction product is purified by chromatography on silica gel (ethyl acetate/heptane 10/90) to give 2 g (37%) of methyl 3-formyl-4-hydroxybenzoate in the form of a white solid; $^1$H NMR (300 MHz, CDCl$_3$): 11.30 (broad s, 1H), 9.90 (s, 1H), 8.26 (d, J=2.1 Hz, 1H), 8.12 (dd, J=2.1 Hz and 8.7 Hz, 1H), 6.96 (d, J=8.7 Hz, 1H), 3.88 (s, 3H).

Stage 2:

Preparation of methyl 4-{[2-(chloromethyl)-2-propenyl]oxy}-3-formylbenzoate 45 ml of dimethylformamide and then 1.15 ml (9.95 mmol) of 2-chloromethyl-3-chloro-1-propene are added under argon to 717 mg (3.98 mmol) of methyl 3-formyl-4-hydroxybenzoate as a mixture with 1.055 g (9.95 mmol) and 440 mg (1.195 mmol) of tetrabutylammonium iodide. The solution is stirred for 26 hours and then water is added. In order to break the emulsion, the pH is brought to 7 using a 1N hydrochloric acid solution. The aqueous phase is extracted several times with ether and then the combined organic phases are washed several times with water and with brine. After drying over magnesium sulfate and concentrating under vacuum, the crude reaction product is purified by chromatography on silica gel (ethyl acetate/heptane 20/80) to give 560 mg (52%) of methyl 4-{[2-(chloromethyl)-2-propenyl]oxy}-3-formylbenzoate in the form of a white solid; 1H NMR (300 MHz, CDCl$_3$): 10.44 (s, 1H), 8.45 (d, J=2.4 Hz, 1H), 8.18 (dd, J=2.4 Hz and 8.4 Hz, 1H), 7.04 (d, J=8.4 Hz, 1H), 5.44 and 5.39 (2s, 2H), 4.79 (s, 2H), 4.19 (s, 2H), 3.87 (s, 3H).

Stage 3:

Preparation of methyl 4-{[2-(iodomethyl)-2-propenyl]oxy}-3-formylbenzoate 375 mg (2.5 mmol) of sodium iodide are added to 560 mg (2.08 mmol) of methyl 4-{[2-(chloromethyl)-2-propenyl]oxy}-3-formylbenzoate in solution in 20 ml of acetone. The solution is brought to reflux and is stirred for 5 hours with the exclusion of light. After the usual treatments, 680 mg (91%) of methyl 4-{[2-(iodomethyl)-2-propenyl]oxy}-3-formylbenzoate are obtained in the form of a white solid which turns yellow in light; $^1$H NMR (300 MHz, CDCl$_3$): 10.48 (s, 1H), 8.48 (d, J=2.4 Hz, 1H), 8.21 (dd, J=2.4 Hz and 8.7 Hz, 1H), 7.07 (d, J=8.7 Hz, 1H), 5.54 (s, 1H), 5.35 (s, 1H), 4.87 (s, 2H), 4.04 (s, 2H), 3.89 (s, 3H, m).

Stage 4:

Preparation of methyl 3-methylene-2,3-dihydro-1-benzoxepine-7-carboxylate 333 mg (1 mmol) of a 60/40 mixture of methyl 4-{[2-(iodomethyl)-2-propenyl]oxy}-3-formylbenzoate and of methyl 4-{[2-(chloromethyl)-2-propenyl]oxy}-3-formylbenzoate and then 297 mg (1.133 mmol) of triphenylphosphine are successively introduced into the 50 ml single-necked flask. The combined mixture is subjected to a stream of nitrogen and then 20 ml of acetonitrile are introduced via a hollow tube. After complete dissolution, the solution is brought to reflux overnight. After cooling the solution, 0.23 ml (1 mmol) of a solution of sodium methoxide in methanol is added dropwise and the medium is stirred for a further one hour. After the usual treatments, 120 mg (54%) of methyl 3-methylene-2,3-dihydro-1-benzoxepin-7-carboxylate are obtained in the form of a white solid; $^1$H NMR (300 MHz, CDCl$_3$): 7.95 (d, J=1.8 Hz, 1H), 7.82 (dd, J=1.8 Hz and 8.4 Hz, 1H), 7.01 (d, J=8.4 Hz, 1H), 6.51 (d, J=12 Hz, 1H), 6.38 (d, J=12 Hz, 1H), 5.28 and 5.11 (2s, 2H), 4.61 (s, 2H), 3.89 (s, 3H).

The following examples of general formula (Xa) for which R$_1$, R$_2$, R$_3$, R$_4$ and R$_5$ are all the hydrogen atom are prepared in a way identical to examples 23 and 35 and illustrate the present invention:

(unless otherwise specified, the NMR spectra are recorded in deuterated chloroform at 300 MHz)

| Example | Y | M.p. or $^1$H NMR |
|---|---|---|
| 36 | OCH$_3$ | 6.93(d, J=8.1Hz, 1H), 6.73(s, 1H), 6.72(m, 1H), 5.21 and 5.05 (2s, 2H), 4.56(s, 2H), 3.78(s, 3H) |
| 37 | NO$_2$ | 8.12(d, J=3Hz, 1H), 7.99(dd, J=3Hz and 9Hz, 1H), 7.05(d, J=9Hz, 1H), 6.58(d, J=11.7Hz, 1H), 6.35(d, J=11.7Hz, 1H), 5.35 and 5.18(2s, 2H), 4.62(s, 2H) |
| 38 | Br | 7.30(d, J=3Hz, 1H), 7.24(dd, J=3Hz and 9Hz, 1H), 6.88(d, J=9Hz, 1H), 6.49(d, J=11.7Hz, 1H), 6.25(d, J=11.7Hz, 1H), 5.27 and 5.10(2s, 2H), 4.57(s, 2H) |
| 39 | I | >230° C. |

EXAMPLE 40

Preparation of 3-methylene-2,3-dihydro-1-benzoxepin-7-carboxylic acid 1.2 g of potassium hydroxide pellets are added to 4 g (18.5 mmol) of methyl 3-methylene-2,3-dihydro-1-benzoxepin-7-carboxylate, prepared according to example 35, in solution in 20 ml of 80% aqueous ethanol. The medium is brought to reflux for 4 hours and then, after cooling, is treated with 1N hydrochloric acid until precipitation. The solid is filtered off and dried to give 3.3 g (88%) of 3-methylene-2,3-dihydro-1-benzoxepin-7-carboxylic acid in the form of a white solid; M.p.=188° C.

EXAMPLE 41

Preparation of 3-methylene-N-phenyl-2,3-dihydro-1-benzoxepin-7-carboxamide 1.12 g (4.07 mmol) of 4-(4,6-dimethoxy-1,3,5-triazin-2-yl)-4-methylmorpholinium chloride and then 0.379 g (4.07 mmol) of aniline are successively added to 0.75 g (3.7 mmol) of 3-methylene-2,3-dihydro-1-benzoxepin-7-carboxylic acid, prepared according to example 40, in solution in 25 ml of methanol. The medium is stirred at ambient temperature for 24 h. After evaporating the methanol, the crude reaction product is purified by chromatography on silica gel (ethyl acetate/heptane 40/60) to give 185 mg (49%) of 3-methylene-N-phenyl-2,3-dihydro-1-benzoxepin-7-carboxamide in the form of a pink solid; M.p.=139° C.

The following examples of general formula (Xa) for which $R_1$, $R_2$, $R_3$, $R_4$ and $R_5$ are all the hydrogen atom are prepared in a way identical to example 41 and illustrate the present invention:

| Example | Y | M.p. |
|---|---|---|
| 42 | benzyl-NH-C(O)-C(CH3)2- | 134° C. |
| 43 | 3,5-dichlorophenyl-NH-C(O)-C(CH3)2- | 131° C. |
| 44 | (CH3)2N-C(O)-C(CH3)2- | 105° C. |

EXAMPLE 45

Preparation of methyl 3-hydroxy-3-(hydroxymethyl)-2,3-dihydro-1-benzoxepin-7-carboxylate 21 g (7 equivalents) of AD-mix-α and 1.31 g (13.8 mmol) of methanesulfonamide dissolved in 75 ml of a 1/1 tert-butyl alcohol/water mixture are added at ambient temperature to 3 g (13.8 mmol) of methyl 3-methylene-2,3-dihydro-1-benzoxepin-7-carboxylate, prepared according to example 35, in suspension in 20 ml of a 1/1 tert-butyl alcohol/water mixture. The reaction medium is stirred for 4 days and is then treated with 2.6 g of sodium disulfite. The medium is reextracted with dichloromethane and the organic phases are washed with brine. After evaporating, the crude reaction product is purified by chromatography on silica gel (ethyl acetate/heptane 50/50) to give 3.2 g (100%) of methyl 3-hydroxy-3-(hydroxymethyl)-2,3-dihydro-1-benzoxepin-7-carboxylate in the form of a colorless honey; $^1$H NMR (300 MHz, CDCl$_3$): 7.88 (d, J=2.4 Hz, 1H), 7.81 (dd, J=2.4 Hz and 8.4 Hz, 1H), 6.98 (d, J=8.4 Hz, 1H), 6.37 (d, J=12 Hz, 1H), 5.88 (d, J=12 Hz, 1H), 4.24 (dd, J=1.2 Hz and 11.7 Hz, 1H), 4.01 (d, J=11.7 Hz, 1H), 3.87 (s, 3H), 3.69 and 3.60 (2d, J=11.4 Hz, 2H).

The following examples of general formula (IXa) for which $R_1$, $R_2$, $R_3$, $R_4$ and $R_5$ are all the hydrogen atom are prepared in a way identical to example 45 and illustrate the present invention:

| Example | Y | Mass (APCI) |
|---|---|---|
| 46 | benzyl-NH-C(O)-C(CH3)2- | M + 1: 326 |
| 47 | 3,5-dichlorophenyl-NH-C(O)-C(CH3)2- | M + 1: 381 |
| 48 | (CH3)2N-C(O)-C(CH3)2- | M + 1: 264 |

EXAMPLE 49

Preparation of methyl 3-oxo-2,3-dihydro-1-benzoxepin-7-carboxylate 116 mg (0.54 mmol) of sodium periodate are added at ambient temperature in 4 equal portions, every quarter of an hour, to 135 mg (0.54 mmol) of methyl 3-hydroxy-3-(hydroxymethyl)-2,3-dihydro-1-benzoxepin-7-carboxylate, prepared according to example 45, in solution in 16 ml of a 3/1 dioxane/water mixture. After the usual treatments, the crude reaction product is purified by chromatography on silica gel (ethyl acetate/heptane 25/75) to give 53 mg (45%) of methyl 3-oxo-2,3-dihydro-1-benzoxepin-7-carboxylate in the form of a white solid; M.p.=98° C.

The following examples of general formula (IIa) for which $R_1$, $R_2$, $R_3$, $R_4$ and $R_5$ are all the hydrogen atom are prepared in a way identical to examples 25 and 49 and illustrate the present invention:

| Example | Y | Mass (APCI) or $_1$H NMR |
|---|---|---|
| 50 | OCH$_3$ | 7.11(d, J=12Hz, 1H), 7.06(d, J=8.7Hz, 1H), 6.89(dd, J=2.7Hz and 8.7Hz, 1H), 6.83(d, J=2.7Hz, 1H), 6.33(d, J=12Hz, 1H), 4.49 (s, 2H), 3.79(s, 3H). |
| 51 | NO$_2$ | 8.32(d, J=3Hz, 1H), 8.23(dd, J=3Hz and 8.7Hz, 1H), 7.29(d, J=8.7Hz, 1H), 7.24(d, J=11.7Hz, 1H), 6.51(d, J=11.7Hz, 1H), 4.63 (s, 2H) |

-continued

| Example | Y | Mass (APCI) or $_1$H NMR |
|---|---|---|
| 52 | Br | 7.50(d, J=3Hz, 1H), 7.46(dd, J=3Hz and 8.7Hz, 1H), 7.09(d, J=8.7Hz, 1H), 7.05(d, J=11.7Hz, 1H), 6.40(d, J=11.7Hz, 1H), 4.56 (s, 2H) |
| 53 | CON(Me)$_2$ | M+1=232, M−1=230 |

EXAMPLE 54

Preparation of methyl 3-(dichloromethylene)-2,3-dihydro-1-benzoxepin-7-carboxylate 0.046 ml (2 equivalents) of bromotrichloromethane is added to 50 mg (0.23 mmol) of methyl 3-oxo-2,3-dihydro-1-benzoxepin-7-carboxylate, prepared according to example 49, and 214 mg (0.92 mmol) of triphenylphosphine in suspension in 0.5 ml of acetonitrile, which is stirred beforehand at 0° C. for 2 hours. The reaction medium is protected from light and is again stirred at ambient temperature for 15 minutes. After the conventional treatments, purification on a column of silica gel (ethyl acetate/heptane 5/95) provides 48 mg (74%) of methyl 3-(dichloromethylene)-2,3-dihydro-1-benzoxepin-7-carboxylate in the form of a white solid; M.p.=119–121° C.

The following examples of general formula (Ia) for which $R_1$, $R_2$, $R_3$, $R_4$ and $R_5$ are all the hydrogen atom and of E and/or Z stereochemistry are prepared in a way identical to example 32 and illustrate the present invention:

| Example | Y | Z (E/Z) | Mass (APCI) or $^1$H NMR |
|---|---|---|---|
| 55 | OMe | =CHCl (10/90) | 6.93(d, J=8.5Hz, 1H), 6.62(d, J=2Hz, 1H), 6.60(dd, J=2Hz and 8.5Hz, 1H), 5.98(d, J=11.8Hz, 1H), 5.83(6.15)(d, J=11.8Hz, 1H), 5.71(5.4)(s, 1H, l), 4.69(4.10)(s, 2H), 3.28(3.27)(s, 3H) |
| 56 | NO$_2$ | =CHCl (20/80) | 8.14(8.18)(d, J=2.7Hz, 1H), 8.03(8.04)(dd, J=2.7Hz and 9Hz, 1H), 7.07(d, J=9Hz, 1H), 6.56(6.95)(d, J=12Hz, 1H), 6.48(6.58)(d, J=12Hz, 1H), 6.45(s, 1H), 4.92(4.62)(s, 1H) |
| 57 | NO$_2$ | =CHPr (20/80) | 8.11(d, J=2.7Hz, 1H), 7.97 (dd, J=2.7Hz and 8.7Hz, 1H), 7.04(d, J=8.7Hz, 1H), 6.48(d, J=11.7Hz, 1H), 6.22(d, J=11.7Hz, 1H), 5.84(5.61)(t, J=7.5Hz, 1H), 4.73(s, 2H), 2.26(dt, J=7.5Hz and 7.5Hz, 2H), 1.35–1.45(m, 2H), 0.93(t, J=6.9Hz, 3H) |
| 58 | Br | =CHCl (10/90) | 7.34(d, J=2.7Hz, 1H), 7.25 (dd, J=2.7Hz and 9Hz, 1H), 6.90(d, J=9Hz, 1H), 6.36(d, J=12Hz, 1H), 6.24(6.58)(d, J=12Hz, 1H), 6.35(s, 1H), 4.84 (4.53)(s, 1H) |

EXAMPLE 59

Preparation of 3-(methoxyimino)-N,N-dimethyl-2,3-dihydro-1-benzoxepin-7-carboxamide 37 mg of N-methylhydroxylamine are added to 150 mg (0.65 mmol) of N,N-dimethyl-3-oxo-2,3-dihydro-1-benzoxepin-7-carboxamide, prepared according to example 53, in solution in 1 ml of methanol, and the medium is stirred at ambient temperature for 2 hours. After evaporating the methanol, followed by the conventional treatments, the crude product is purified to provide 65 mg (38%) of 3-(methoxyimino)-N,N-dimethyl-2,3-dihydro-1-benzoxepin-7-carboxamide, as an equimolecular mixture of the E and Z isomers, in the form of a yellow oil:mass (APCI) M+1:261

The following examples of general formula (Ia) for which $R_1$, $R_2$, $R_3$, $R_4$ and $R_5$ are all the hydrogen atom and of E and/or Z stereochemistry are prepared in a way identical to example 59 and illustrate the present invention:

| Example | Y | Z (E/Z) | Mass (APCI) |
|---|---|---|---|
| 60 | COOMe | =NMe(Ph) (75/25) | M + 1 = 323 |
| 61 | COOMe | =NOCH$_2$Ph (66/34) | M + 1 = 324 |
| 62 | COOMe | =NN(Me)$_2$ (80/20) | M + 1 = 261 |

EXAMPLE 63

Preparation of 3-(chloromethylene)-2,3-dihydro-1-benzoxepin-7-carboxylic acid 145 mg (2.6 mmol) of potassium hydroxide pellets are added to 0.5 g (2 mmol) of methyl 3-(chloromethylene)-2,3-dihydro-1-benzoxepin-7-carboxylate, prepared according to example 32, in solution in 8 ml of 80% aqueous ethanol, and the medium is brought to reflux for 3 hours. After cooling, the medium is brought to acidity by addition of 1N hydrochloric acid. The precipitate is filtered off and then washed with diisopropyl ether to provide 300 mg (63%) of 3-(chloromethylene)-2,3-dihydro-1-benzoxepin-7-carboxylic acid in the form of a white solid comprising two Z/E isomers as a mixture in an 85/15 ratio; M.p.>260° C.

EXAMPLE 64

Preparation of 3-(chloromethylene)-N-phenyl-2,3-dihydro-1-benzoxepin-7-carboxamide 127 mg (0.46 mmol) of 4-(4,6-dimethoxy-1,3,5-triazin-2-yl)-4-methylmorpholinium chloride and then 39 mg (0.42 mmol) of aniline are added to 100 mg (0.42 mmol) of 3-(chloromethylene)-2,3-dihydro-1-benzoxepin-7-carboxylic acid, prepared according to example 63, in solution in 4 ml of methanol, and the medium is stirred at ambient temperature for 3 hours. The methanol is evaporated and the crude reaction product is purified by chromatography on silica gel (ethyl acetate/heptane 40/60) to give 20 mg (15%) of 3-(chloromethylene)-N-phenyl-2,3-dihydro-1-benzoxepin-7-carboxamide in the form of a pink solid comprising two Z/E isomers as a mixture in an 85/15 ratio; mass (APCI) M+1=312.

The following examples of general formula (Ia) for which $R_1$, $R_2$, $R_3$, $R_4$ and $R_5$ are all the hydrogen atom and of E and/or Z stereochemistry are prepared in a way identical to example 64 and illustrate the present invention:

| Example | Y | Z (E/Z) | Mass (APCI) |
|---|---|---|---|
| 65 | CONHCH$_2$Ph | =CHCl (15/85) | M + 1 = 326 |
| 66 | CON(Me)$_2$ | =CHCl (20/80) | M + 1 = 264 |
| 67 | 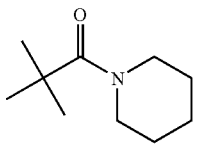 | =CHCl (20/80) | M + 1 = 305 |
| 68 | COOiPr | =CHCl (15/85) | M − 1 = 278 |
| 69 | 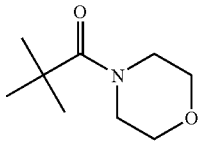 | =CHCl (15/85) | M + 1 = 307 |
| 70 | COOCH$_2$Ph | =CHCl (15/85) | M + 1 = 326 |

EXAMPLE 71

Preparation of [3-(chloromethylene)-2,3-dihydro-1-benzoxepin-7-yl]methanol 2.72 ml (2.72 mmol) of a lithium diisobutylaluminum hydride solution are added at a temperature of −78° C. to 217 mg (0.87 mmol) of methyl 3-(chloromethylene)-2,3-dihydro-1-benzoxepin-7-carboxylate, prepared according to example 32, in solution in 10 ml of dichloromethane. The solution is stirred at this temperature for 1 hour. A conventional treatment makes it possible to isolate 211 mg (100%) of [3-(chloromethylene)-2,3-dihydro-1-benzoxepin-7-yl]methanol in the form of a white solid comprising two Z/E isomers as a mixture in a 90/10 ratio; $^1$H NMR (C$_6$D$_6$): 6.98 (d, J=8.2 Hz, 1H), 6.97 (m, 1H), 6.90 (dd, J=8.2 Hz and 2.2 Hz, 1H), 6.07 (d, J=11.8 Hz, 1H), 5.86 (d, J=11.8 Hz, 1H), 5.74 (s, 1H), 4.68 (s, 2H), 4.28 (4.1) (s, 2H).

EXAMPLE 72

Preparation of 3-(chloromethylene)-2,3-dihydro-1-benzoxepin-7-carbaldehyde 84 mg (0.62 mmol) of 4-methylmorpholine N-oxide monohydrate and 207 mg of 4 Å molecular sieve are added to 92 mg (0.415 mmol) of [3-(chloromethylene)-2,3-dihydro-1-benzoxepin-7-yl]methanol, prepared according to example 71, in solution in 1 ml of dichloromethane. 14.6 mg (0.041 mmol) of tetrapropylammonium perruthenate are added to the suspension at 0° C. After stirring at ambient temperature for 1 hour, the reaction medium is purified by chromatography on silica gel (ethyl acetate/heptane 30/70) to give 70 mg (76%) of 3-(chloromethylene)-2,3-dihydro-1-benzoxepin-7-carbaldehyde in the form of a mixture of 2 Z/E isomers in an 85/15 ratio; $^1$H NMR (300 MHz, CDCl$_3$) Z isomer: 4.90 (s, 2H), 6.41 (m, 3H), 7.14 (d, J=8.3 Hz, 1H), 7.70 (dd, J=8.3 and 2 Hz, 1H), 7.75 (d, J=2.07 Hz, 1H), 9.91 (s, 1H).

EXAMPLE 73

Preparation of 1-[3-(chloromethylene)-2,3-dihydro-1-benzoxepin-7-yl]ethanone oxime 12.3 mg (0.15 mmol) of sodium acetate and then 10.4 mg (0.15 mmol) of hydroxylamine hydrochloride are added at ambient temperature to 30 mg (0.136 mmol) of 3-(chloromethylene)-2,3-dihydro-1-benzoxepin-7-carbaldehyde, prepared according to example 72, in solution in 2 ml of methanol. The solution is stirred for 24 hours and is then hydrolyzed. A conventional treatment makes it possible to obtain 35 mg (100%) of 1-[3-(chloromethylene)-2,3-dihydro-1-benzoxepin-7-yl]ethanone oxime in the solid form; $^1$H NMR: 7.9–8.3 (broad s, OH), 8.10 (8.05) (s, 1H), 7.35–7.45 (m, 2H), 7.03 (7.00) (d, J=8.4 Hz, 1H), 6.84 (d, J=11.7 Hz, 1H), 6.35 (s, 3H), 4.88 (4.57)(s, 2H).

EXAMPLE 74

Preparation of 3-(chloromethylene)-7-[4-(2-methyl-1,3-dioxolan-2-yl)-1-butenyl]-2,3-dihydro-1-benzoxepin 0.206 ml (0.41 mmol) of a 1.9M n-butyllithium solution is added dropwise to 207 mg (0.435 mmol) of [3-(2-methyl-1,3-dioxolan-2-yl)propyl](triphenyl)phosphonium iodide in suspension in 3.2 ml of tetrahydrofuran cooled to 0° C. The medium is stirred for one hour and then the ylide is added at 0° C., via a hollow tube, to 48 mg (0.22 mmol) of 3-(chloromethylene)-2,3-dihydro-1-benzoxepin-7-carbaldehyde, prepared according to example 72, in solution in 3.6 ml of tetrahydrofuran. The medium is stirred at ambient temperature for 25 minutes and then water and dichloromethane are added. The phases are separated and the aqueous phase is extracted with dichloromethane. The combined organic phases are then washed with brine, are then dried and are then finally concentrated under vacuum. The crude reaction product is purified by chromatography on silica gel (ethyl acetate/heptane 10/90) to give 47 mg (71%) of 3-(chloromethylene)-7-[4-(2-methyl-1,3-dioxolan-2-yl)-1-butenyl]-2,3-dihydro-1-benzoxepin in the form of a mixture of four diastereoisomers in a Z/E (60/40) ratio for the unsaturated chain and a Z/E ratio (85/15) for the chloromethylene functional group; $^1$H NMR (300 MHz, CDCl$_3$) ZZ isomer: 1.32 (s, 3H), 1.81 (m, 2H), 2.44 (m, 2H), 3.9 (m, 4H), 4.86 (s, 2H), 5.63 (m, 1H), 6.31 (m, 4H), 6.96 (m, 3H).

EXAMPLE 75

Preparation of EZ-6-[3-(chloromethylene)-2,3-dihydro-1-benzoxepin-7-yl]-5-hexen-2-one 6 mg (0.023 mmol) of bis(acetonitrile)palladium(II) chloride are added to 79 mg (0.237 mmol) of 3-(chloromethylene)-7-[4-(2-methyl-1,3-dioxolan-2-yl)-1-butenyl]-2,3-dihydro-1-benzoxepin, prepared according to example 74, in solution in 1.5 ml of dichloromethane. After stirring at ambient temperature for 3 hours, 0.5 ml of acetone and a catalytic amount of para-toluenesulfonic acid are added. The reaction medium is then stirred for 30 minutes. The crude reaction product is purified by chromatography on silica gel (ethyl acetate/heptane 10/90) to provide 55 mg (80%) of 6-[3-(chloromethylene)-2,3-dihydro-1-benzoxepin-7-yl]-5-hexen-2-one in the form of a mixture of isomers in an EZ/EE ratio (85/15) for the chloromethylene functional group; $^1$H NMR (300 MHz, CDCl$_3$) EZ isomer: 2.18 (s, 3H), 2.45 (m, 2H), 2.61 (m, 2H), 4.86 (s, 2H), 6.10 (m, 1H), 6.33 (m, 4H), 6.96 (m, 3H).

EXAMPLE 76

Preparation of EE-6-[3-(chloromethylene)-2,3-dihydro-1-benzoxepin-7-yl]-5-hexen-2-one A crystal of iodine is added to 55 mg (0.19 mmol) of EZ-6-[3-(chloromethylene)-2,3-dihydro-1-benzoxepin-7-yl]-5-hexen-2-one, prepared according to example 75, in solution in a 7/1 heptane/dichloromethane mixture. The reaction medium is heated at 100° C. for 50 minutes. After cooling, a saturated sodium thiosulfate solution is added, as is dichloromethane. The phases are separated and then the aqueous phase is extracted with dichloromethane. The combined organic phases are then washed with brine, are then dried and are finally concentrated under vacuum. The crude reaction product is purified by chromatography on silica gel (ethyl acetate/heptane 10/90) to give 50 mg (92%) of 6-[3-(chloromethylene)-2,3-dihydro-1-benzoxepin-7-yl]-5-hexen-2-one in the form of a mixture of isomers in an EZ/EE ratio (30/70) for the chloromethylene functional group; exact mass (IC): calculated 288.09171; found 288.09937.

EXAMPLE 77

Preparation of 1-(3-methylene-2,3-dihydro-1-benzoxepin-7-yl)ethanone

Stage 1:

Preparation of 5-acetyl-2-{[2-(chloromethyl)-2-propenyl]oxy}benzaldehyde 6.02 g (16.31 mmol) of tetrabutylammonium iodide, 6.17 g (2.5 equivalents) of sodium carbonate and, finally, 6.7 ml (58.2 mmol) of 2-chloromethyl-3-chloro-1-propene are successively added to 3.82 g (23 mmol) of 5-acetyl-2-hydroxybenzaldehyde, prepared according to Tromelin, A. et al., Synthesis, (1985), 1074–1076, and then Laali, K. et al., Journal of Organic Chemistry, 58, (1993), 1385–1392, in solution in 250 ml of N,N-dimethylformamide. The medium is stirred for 21 hours. After addition of water and 1N hydrochloric acid, the solution is extracted with dichloromethane. The organic phase is subsequently washed, then dried and, finally, concentrated under vacuum. The crude reaction product is purified by chromatography on silica gel (ethyl acetate/heptane 20/80) to give 3.06 g (52%) of 5-acetyl-2-{[2-(chloromethyl)-2-propenyl]oxy}benzaldehyde in the form of a yellow-white solid; $^1$H NMR (300 MHz, CDCl$_3$): 10.49 (s, 1H), 8.38 (d, J=2.1 Hz, 1H), 8.18 (dd, J=2.1 Hz and 8.7 Hz, 1H), 7.08 (d, J=8.7 Hz, 1H), 5.46 and 5.41 (2s, 2H), 4.83 (s, 2H), 4.21 (s, 2H), 2.58 (s, 3H).

Stage 2:

Preparation of 5-acetyl-2-{[2-(iodomethyl)-2-propenyl]oxy}benzaldehyde 531 mg (3.54 mmol) of sodium iodide are added to 894 mg (3.54 mmol) of 5-acetyl-2-{[2-(chloromethyl)-2-propenyl]oxy}benzaldehyde in solution in 10 ml of distilled acetone. The medium is brought to reflux and is stirred for 5 hours. Water is added and then the solution is concentrated. After the addition of water and dichloromethane, the phases are separated by settling and then the aqueous phase is extracted with dichloromethane. The combined organic phases are washed, dried and then concentrated under vacuum to give 1.22 g (100%) of 5-acetyl-2-{[2-(iodomethyl)-2-propenyl]oxy}benzaldehyde in the form of a white solid which turns yellow in air; $^1$H NMR (300 MHz, CDCl$_3$): 10.46 (s, 1H), 8.34 (d, J=2.4 Hz, 1H), 8.15 (dd, J=2.4 Hz and 8.7 Hz, 1H), 7.08 (d, J=8.7 Hz, 1H), 5.52 and 5.32 (2s, 2H), 4.86 (s, 2H), 4.01 (s, 2H), 2.54 (s, 3H).

Stage 3:

Preparation of 1-(3-methylene-2,3-dihydro-1-benzoxepin-7-yl)ethanone 973 mg (3.575 mmol) of triphenylphosphine are added under argon to 1.118 g (3.25 mmol) of 5-acetyl-2-{[2-(iodomethyl)-2-propenyl]oxy}benzaldehyde in solution in 30 ml of acetonitrile. The medium is brought to reflux and is stirred for 14 hours. After cooling the solution, 0.743 ml (3.25 mmol) of a 25% solution of sodium methoxide in methanol is added. The medium is stirred at ambient temperature for 3 hours and then water is added. After concentrating the solution under vacuum, dichloromethane is added. The phases are then separated and the aqueous phase is extracted with dichloromethane. The combined organic phases are washed, are then dried and are finally concentrated under vacuum. The crude reaction product is purified by chromatography on silica gel (ethyl acetate/heptane 10/90) to give 377 mg (58%) of 1-(3-methylene-2,3-dihydro-1-benzoxepin-7-yl)ethanone in the form of a white solid; $^1$H NMR (300 MHz, CDCl$_3$): 7.86 (d, J=2.1 Hz, 1H), 7.75 (dd, J=2.1 Hz and 8.4 Hz, 1H), 7.03 (d, J=8.4 Hz, 1H), 6.51 (d, J=11.7 Hz, 1H), 6.38 (d, J=11.7 Hz, 1H), 5.28 and 5.11 (2s, 2H), 4.61 (s, 2H), 2.56 (s, 3H).

EXAMPLE 78

Preparation of 1-β-hydroxy-3-(hydroxymethyl)-2,3-dihydro-1-benzoxepin-7-yl]ethanone 89 mg (1 equivalent) of osmium tetroxide and methanesulfonamide, dissolved at ambient temperature in 10 ml of a 1/1 tert-butanol/water mixture, are added at 0° C. to 190 mg (0.95 mmol) of 1-(3-methylene-2,3-dihydro-1-benzoxepin-7-yl)ethanone, prepared according to example 77. The medium is vigorously stirred for 3.5 days and then 1.78 g of sodium metabisulfite (1780 mg) are added portionwise at ambient temperature. Dichloromethane is added, the phases are separated by settling and then the aqueous phase is extracted with dichloromethane. The combined organic phases are then washed with brine, dried over magnesium sulfate and concentrated under vacuum to give 157 mg (70%) of 1-β-hydroxy-3-(hydroxymethyl)-2,3-dihydro-1-benzoxepin-7-yl]ethanone in the form of an oil; $^1$H NMR (300 MHz, CDCl$_3$): 7.79 (d, J=2.1 Hz, 1H), 7.74 (dd, J=2.1 Hz and 8.4 Hz, 1H), 7.00 (dd, J=8.4 Hz and 1.5 Hz), 6.38 (dd, J=1.5 Hz and 12 Hz, 1H), 5.90 (d, J=12 Hz, 1H), 4.26 and 4.00 (2d, J=12 Hz, 2H), 3.69 and 3.59 (2d, J=11.4 Hz, 2H), 2.54 (s, 3H).

EXAMPLE 79

Preparation of 7-acetyl-1-benzoxepin-3(2H)-one 145 mg (0.68 mmol) of sodium periodate are added, in four equal parts, to 157 mg (0.67 mmol) of 1-β-hydroxy-3-(hydroxymethyl)-2,3-dihydro-1-benzoxepin-7-yl]ethanone, prepared according to example 78, in solution in 10 ml of a 3/1 dioxane/water mixture. After stirring for 5.5 hours, the solution is filtered through a cotton filter and the white solid is washed with dichloromethane. After separating the filtrate by settling, the aqueous phase is extracted with dichloromethane. The combined organic phases are washed, dried and finally concentrated under vacuum. The crude reaction product is then purified by chromatography on silica gel (ethyl acetate/heptane 30/70) to give 106 mg (78%) of 7-acetyl-1-benzoxepin-3(2H)-one in the form of a white solid; $^1$H NMR (300 MHz, CDCl$_3$): 8.02 (d, J=2.1 Hz, 1H), 7.96 (dd, J=2.1 Hz and 8.4 Hz, 1H), 7.25 (d, J=12 Hz, 1H), 7.22 (d, J=8.4 Hz, 1H), 6.44 (d, J=2 Hz, 1H), 4.59 (s, 2H), 2.61 (s, 3H).

EXAMPLE 80

Preparation of 1-[3-(chloromethylene)-2,3-dihydro-1-benzoxepin-7-yl]ethanone 1.1 equivalents of n-butyllithium are added to 309 mg (0.89 mmol) of chloromethyltriphenylphosphonium chloride in 5 ml of tetrahydrofuran cooled to 0° C. After stirring for one hour, 150 mg (0.74 mmol) of 7-acetyl-1-benzoxepin-3(2H)-one, prepared according to example 79, are added at ambient temperature. The medium is stirred for a further 1 hour. After the usual treatments and evaporating the solvent under reduced pressure, the crude reaction product is taken up in pentane in order to precipitate triphenylphosphine oxide. Evaporation of the solvents provides 95.5 mg (55%) of 1-[3-(chloromethylene)-2,3-dihydro-1-benzoxepin-7-yl] ethanone in the form of a mixture of two Z/E isomers in a 90/10 ratio; $^1$H NMR (C$_6$D$_6$): 7.85 (d, 1H, J=2.2 Hz), 7.76 (dd, 2.2 Hz and 8.4 Hz), 7.04 (d, 8.4 Hz), 6.85 (d, J-=11.8 Hz, 1H), 6.57 (d, J=11.8 Hz, 1H), 6.16 (s, 1H), 4.57 (4.87) (s, 2H), 2.56 (s, 3H).

The following examples of general formula (Ia) of E and/or Z stereochemistry, for which R$_1$, R$_2$, R$_3$, R$_4$ and R$_5$ are all the hydrogen atom and Y is the acetyl radical, are prepared in a way identical to example 80 and illustrate the present invention:

| Example | Z (E/Z) | NMR |
|---|---|---|
| 81 | =CH(COOMe) (40/60) | 8.05(d, J=12Hz, 1H), 7.73(d, J=2.1Hz, 1H), 7.64(d, J=2.1Hz, 1H), 7.54(dd, J=2.1Hz and 8.4Hz, 1H), 7.43(dd, J=2.1Hz and 8.4Hz, 1H), 6.82(dd, J=1.8Hz and 8.4Hz, 1H), 6.24(d, J=12.6Hz, 1H), 6.09 (d, J=11.4Hz, 1H), 5.90(d, J=11.4Hz, 1H), 5.70(s, 1H), 5.39 (s, 1H), 5.34(s, 2H), 4.08(s, 2H), 3.37(s, 3H), 3.32(s, 3H), 2.07(s, 3H), 2.06(s, 3H) |
| 82 | =CH(SMe) (75/25) | 7.86(d, J=2.1Hz, 1H), 7.83(d, J=2.1Hz, 1H), 7.73(dd, J=2.1Hz and 8.4Hz, 1H), 7.73(dd, J=2.1Hz and 8.4Hz, 1H), 7.05(d, J=8.4Hz, 1H), 7.00(d, J=8.4Hz, 1H), 6.67(d, J=11.4Hz, 1H), 6.43(d, J=11.4Hz, 1H), 6.39(d, J=11.7Hz, 1H), 6.31 (s, 1H), 6.22(d, J=11.7Hz, 1H), 6.09(s, 1H), 4.74(s, 2H), 4.55(s, 2H), 2.56(s, 3H), 2.38(s, 3H) |
| 83 | =CHMe (80/20) | 7.88(d, J=2.1Hz, 1H), 7.84(d, J=2.1Hz, 1H), 7.74(dd, J=2.1Hz and 8.4Hz, 1H), 7.73(dd, J=2.1Hz and 8.4Hz, 1H), 7.02(d, J=8.4Hz, 1H), 7.01(d, J=8.4Hz, 1H), 6.73(d, J=11.7Hz, 1H), 6.42(d, J=11.4Hz, 1H), 6.24(d, J=11.4Hz, 1H), 5.85 (q, J=7.5Hz, 1H), 5.62(q, J=7.2Hz, 1H), 4.72(s, 2H), 4.54(s, 2H), 2.57 (s, 3H), 1.88(d, J=7.5Hz, 1H), 1.86 (d, J=7.5Hz, 1H) |
| 84 | =CHPh (90/10) | 7.89(d, J=2.1Hz), 7.75(J=2.1Hz and 8.4Hz, 1H), 7.2–7.4(m, 5H), 7.06(d, J=8.4Hz, 1H), 7.03(d, J=8.4Hz, 1H), 6.86(d, J=11.7Hz, 1H), 6.81(s, 1H), 6.62(d, J=11.7Hz, 1H), 6.54(s, 1H), 6.51 (d, J=11.7Hz, 1H), 6.44(d, J=11.7Hz), 4.89(s, 2H), 4.72(s, 2H), 2.58(s, 3H) |
| 85 | =CH(OMe) (44/56) | 7.85(d, J=2.1Hz, 1H), 7.81(d, J=2.1Hz, 1H), 7.70(dd, J=2.1Hz and 8.4Hz, 1H), 7.68(dd, J=2.1Hz and 8.4Hz, 1H), 7.01(d, J=8.4Hz, 1H), 6.98(d, J=8.4Hz, 1H), 6.79(d, J=11.7Hz, 1H), 6.35(s, 1H), 6.29 (d, J=11.7Hz, 1H), 6.21(d, J=11.4Hz, 1H), 6.16(d, J=11.4Hz, 1H), 6.08(s, 1H), 4.76(s, 2H), 4.48 (s, 2H), 3.76(s, 3H), 3.74(s, 3H), 2.56(s, 6H) |
| 86 | =CH(CN) (40/60) | 7.91(d, J=2.1Hz, 1H), 7.85(dd, J=2.1Hz and 8.7Hz, 1H), 7.12(dd, J=1.8Hz and 8.4Hz, 1H), 7.13(dd, J=1.8Hz and 8.4Hz, 1H), 6.95(d, J=12.5Hz, 1H), 6.72(d, J=12.5Hz, 1H), 6.80(d, J=12.5Hz, 1H), 6.58 (d, J=12.5Hz, 1H), 5.22(s, 1H), 5.43(s, 1H), 4.66(s, 2H), 4.93(s, 2H), 2.58(s, 3H) |

Biological Test:

General Description

The test is carried out on isolated fungi in a culture medium, in 96-well microplates. The products are dissolved in acetonitrile and are then diluted to 1/50$^{th}$ in methanol, so as to distribute 50 μl for a dose of 50 ppm in each well. Once the compounds are distributed, the microplates are dried under a stream of nitrogen at 40° C. The culture medium and the inoculum are subsequently added.

The growth of the fungi is measured after culturing for 5 days at 20° C. by reading the optical density at 620 nm or 405 nm, depending on the strains. The effectiveness of the product is the percentage of inhibition of the growth of the fungi calculated according to Abbott's formula, the absorbance of the growth control wells and the absorbance of the treated wells being taken as reference values.

EXAMPLE B1

At a dose of 50 ppm, complete or good (at least 70%) inhibition of *Botrytis cinerea* is observed with the compounds described in the following examples: 28, 32, 47, 65, 68 and 70.

EXAMPLE B2

At a dose of 50 ppm, complete or good (at least 70%) inhibition of *Septoria nodorum* is observed with the compounds described in the following examples: 5, 28, 29, 30, 32, 33, 34, 40, 55, 57, 63, 65, 67, 68, 70, 72, 82 and 86.

EXAMPLE B3

At a dose of 50 ppm, complete or good (at least 70%) inhibition of *Monilia fructigena* is observed with the compounds described in the following examples: 28, 32 and 70.

EXAMPLE B4

At a dose of 50 ppm, complete or good (at least 70%) inhibition of *Phytophthora cinnamomi* is observed for the compounds described in the following example: 70.

EXAMPLE B5

At a dose of 50 ppm, complete or good (at least 70%) inhibition of *Magnaporthe orysae* is observed with the compounds described in the following examples: 28 and 32.

EXAMPLE B6

At a dose of 50 ppm, complete or good (at least 70%) inhibition of *Rhizoctonia solani* is observed with the compounds described in the following examples: 28, 32, 55, 68 and 70.

EXAMPLE B7

At a dose of 50 ppm, complete or good (at least 70%) inhibition of *Mycosphaerella graminacola* is observed with the compounds described in the following examples: 28, 32, 55 and 70.

EXAMPLE B8

At a dose of 50 ppm, complete or good (at least 70%) inhibition of *Venturia pirina* is observed with the compounds described in the following example: 28.

What is claimed is:
1. A compound of general formula (Ia) or (Ib):

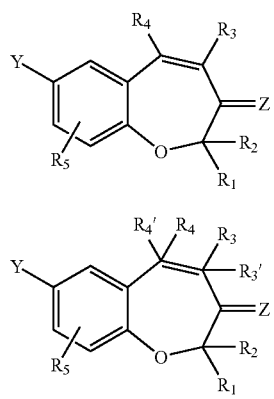

in which:
Y is selected from the group consisting of a halogen atom selected from the group consisting of fluorine, chlorine, bromine and iodine, the formyl radical, the carboxyl radical, an alkoxy radical, the linear or branched alkyl part comprising from 1 to 6 carbon atoms, a cycloalkoxy radical, the cycloalkyl part comprising from 3 to 7 carbon atoms, a hydroxyalkyl radical, the linear or branched alkyl part comprising from 1 to 6 carbon atoms, the nitro radical, an alkylcarbonyl radical, the linear or branched alkyl part comprising from 1 to 6 carbon atoms, a cycloalkylcarbonyl radical, the cycloalkyl part comprising from 3 to 7 carbon atoms, an alkoxycarbonyl radical, the linear or branched alkyl part comprising from 1 to 6 carbon atoms, a cycloalkoxycarbonyl radical, the cycloalkyl part comprising from 3 to 7 carbon atoms, a heterocyclyloxycarbonyl radical, an alkylcarbonyloxy radical, the linear or branched alkyl part comprising from 1 to 6 carbon atoms, a cycloalkylcarbonyloxy radical, the cycloalkyl part comprising from 3 to 7 carbon atoms, an —$SR_1$, —$SOR_1$, —$SO_2R_1$, —$C(O)NR_1R_6$, —$C(O)NR_1(OR_2)$, —$C(O)NR_1(NR_2R_6)$, —$C(S)NR_1R_6$, —$NR_1C(O)NR_2R_6$, —$NR_1C(S)NR_2R_6$, —$OC(O)NR_1R_6$, —$NR_1R_6$, —$NR_1(OR_2)$, —$C(R_1)=NR_6$, —$C(R_1)=NR_6(OR_2)$, —$C(R_1)=NR_6(NR_2R_6)$ or —$N=NR_1R_6$ radical, a linear or branched alkyl radical comprising from 1 to 20 carbon atoms, a cycloalkyl radical comprising from 3 to 7 carbon atoms, an aryl, aryloxy, heteroaryl, heteroaryloxy, arylalkyl, arylalkyloxy, heteroarylalkyl, heteroarylalkyloxy, arylcarbonyl, heteroarylcarbonyl, arylcarbonyloxy or heteroarylcarbonyloxy radical, the hydroxyl radical and the cyano radical;
Z is a divalent radical selected from the group consisting of =O, =$CR_1X$, =CXX', =$CR_1$(CN), =$CR_1R_2$, =$CR_1(OR_2)$, =$CR_1$—$C(O)R_2$, =$CR_1$—$C(O)OR_2$, =$CR_1(SR_2)$, =$CR_1(NR_2R_6)$, =$NR_1$, =$N(OR_1)$ and =$N(NR_1R_6)$;
X and X' are identical or different and are selected from the group consisting of fluorine, chlorine, bromine and iodine;
$R_1$, $R_2$, $R_3$, $R_3'$, $R_4$ and $R_4'$ are identical or different and are selected from the group consisting of hydrogen, a linear or branched alkyl radical comprising from 1 to 20 carbon atoms, a cycloalkyl radical comprising from 3 to 7 carbon atoms, an aryl radical, an arylalkyl radical, a heteroaryl radical and a heteroarylalkyl radical;
the two substituents $R_1$ and $R_2$ can together form a saturated or unsaturated ring or heterocycle comprising 3 to 8 atoms;
the two substituents $R_3$ and $R_4$ can together form a saturated or unsaturated ring or heterocycle comprising 3 to 8 atoms,
$R_5$ is selected from the group consisting of the hydrogen atom, the hydroxyl radical, a linear or branched alkyl radical comprising from 1 to 6 carbon atoms, a halogen atom selected from the group consisting of fluorine, chlorine, bromine and iodine, the formyl radical, the carboxyl radical, an alkoxy radical, the linear or branched alkyl part comprising from 1 to 6 carbon atoms, a cycloalkoxy radical, the cycloalkyl part comprising from 3 to 7 carbon atoms, the nitro radical, an alkylcarbonyl radical, the linear or branched alkyl part comprising from 1 to 6 carbon atoms, a cycloalkylcarbonyl radical, the cycloalkyl part comprising from 3 to 7 carbon atoms, an alkoxycarbonyl radical, the linear or branched alkyl part comprising from 1 to 6 carbon atoms, a cycloalkoxycarbonyl radical, the cycloalkyl part comprising from 3 to 7 carbon atoms, a heterocyclyloxycarbonyl radical, a cycloalkoxycarbonyl radical, the cycloalkyl part comprising from 3 to 7 carbon atoms, an alkylcarbonyloxy radical, the linear or branched alkyl part comprising from 1 to 6 carbon atoms, a cycloalkylcarbonyloxy radical, the cycloalkyl part comprising from 3 to 7 carbon atoms, an —SR$_1$, —SOR$_1$, —SO$_2$R$_1$, —C(O)NR$_1$R$_6$, —NR$_1$R$_6$, —NR$_1$C(O)NR$_1$R$_6$, —NR$_1$(OR$_2$), —C(R$_1$)=NR$_6$ or —N=NR$_1$R$_2$ radical, a linear or branched alkyl radical comprising from 1 to 6 carbon atoms, a linear or branched alkenyl radical comprising from 1 to 6 carbon atoms, a cycloalkyl radical comprising from 3 to 7 carbon atoms, an aryl, aryloxy, heteroaryl, heteroaryloxy, arylalkyl, arylalkyloxy, heteroarylalkyl, heteroarylalkyloxy, arylcarbonyl, heteroarylcarbonyl, arylcarbonyloxy or heteroarylcarbonyloxy radical, the cyanato radical, the thiocyanato radical, the azido radical and the cyano radical;

R$_6$ is selected from the group consisting of the hydrogen atom, a linear or branched alkyl radical comprising from 1 to 6 carbon atoms, a phenyl radical, a naphthyl radical, a phenylalkyl radical, the alkyl part being linear or branched and comprising from 1 to 6 carbon atoms, a naphthylalkyl radical, the alkyl part being linear or branched and comprising from 1 to 6 carbon atoms, an alkylcarbonyl radical, the linear or branched alkyl part comprising from 1 to 6 carbon atoms, an alkoxycarbonyl radical, the linear or branched alkyl part comprising from 1 to 6 carbon atoms, an N,N'-dialkylaminocarbamoyl radical, the linear or branched alkyl parts comprising from 1 to 6 carbon atoms, an alkylsulfonyl radical, the linear or branched alkyl part comprising from 1 to 6 carbon atoms, an arylsulfonyl radical and an N,N'-dialkylaminosulfonyl radical, the linear or branched alkyl parts comprising from 1 to 6 carbon atoms;

with the restriction that, for the compound of formula (Ia),
when Z represents the =CHCl radical and R$_1$, R$_2$, R$_3$, R$_4$ and R$_5$ each represent a hydrogen atom, then Y cannot represent the methylcarbonyl radical or the methoxycarbonyl radical, the formyl radical, the hydroxymethyl radical, the carboxyl radical, the bromo radical or the cyano radical,
when Z represents the =CH$_2$ radical and R$_1$, R$_2$, R$_3$, R$_4$ and R$_5$ each represent a hydrogen atom, then Y cannot represent the methoxycarbonyl or the bromo radical,
when Z represents the =O radical and R$_1$, R$_2$, R$_3$, R$_4$ and R$_5$ each represent a hydrogen atom, then Y cannot represent the bromo radical;
and that, for the compounds of formula (Ib),
when Z represents the =CHCl radical and R$_1$, R$_2$, R$_3$, R$_3$', R$_4$, R$_4$' and R$_5$ each represent a hydrogen atom, then Y cannot represent the methylcarbonyl radical,
when Z represents the =O radical and R$_2$, R$_3$, R$_3$', R$_4$, R$_4$' and R$_5$ each represent a hydrogen atom, then Y and R$_1$ cannot represent, both or independently of one another, a hydrogen atom or an alkyl radical comprising 1 to 4 carbon atoms;
and to their possible geometrical and/or optical isomers, to their possible tautomeric forms and to their salts, N-oxides and metal and semimetal complexes.

2. The compound as claimed in claim 1, for which R$_3$ represents the hydrogen atom.

3. The compound as claimed in claim 2, for which R$_2$ represents the hydrogen atom.

4. The compound as claimed in claim 1, for which R$_1$ represents the hydrogen atom.

5. The compound as claimed in claim 1, for which R$_1$, R$_2$, R$_3$, R$_3$' and R$_4$' each represent the hydrogen atom.

6. The compound of formula (Ib) as claimed in claim 1, for which R$_4$' represents the hydrogen atom.

7. A process for the preparation of a compound of formula (Ia)

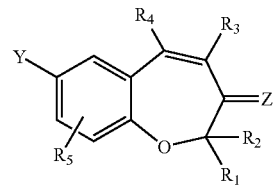

(Ia)

in which Y is selected from the group consisting of hydrogen, a halogen atom selected from the group consisting of fluorine, chlorine, bromine and iodine, the formyl radical, the carboxyl radical, an alkoxy radical, the linear or branched alkyl part comprising from 1 to 6 carbon atoms, a cycloalkoxy radical, the cycloalkyl part comprising from 3 to 7 carbon atoms, a hydroxyalkyl radical, the linear or branched alkyl part comprising from 1 to 6 carbon atoms, the nitro radical, an alkylcarbonyl radical, the linear or branched alkyl part comprising from 1 to 6 carbon atoms, a cycloalkylcarbonyl radical, the cycloalkyl part comprising from 3 to 7 carbon atoms, an alkoxycarbonyl radical, the linear or branched alkyl part comprising from 1 to 6 carbon atoms, a cycloalkoxycarbonyl radical, the cycloalkyl part comprising from 3 to 7 carbon atoms, a heterocyclyloxycarbonyl radical, an alkylcarbonyloxy radical, the linear or branched alkyl part comprising from 1 to 6 carbon atoms, a cycloalkylcarbonyloxy radical, the cycloalkyl part comprising from 3 to 7 carbon atoms, an —SR$_1$, —SOR$_1$, —SO$_2$R$_1$, —C(O)NR$_1$R$_6$, —C(O)NR$_1$(OR$_2$), —C(O)NR$_1$(NR$_2$R$_6$), —C(S)NR$_1$R$_6$, —NR$_1$C(O)NR$_2$R$_6$, —NR$_1$C(S)NR$_2$R$_6$, —OC(O)NR$_1$R$_6$, —NR$_1$R$_6$, —NR$_1$(OR$_2$), —C(R$_1$)=NR$_6$, —C(R$_1$)=NR$_6$(OR$_2$), —C(R$_1$)=NR$_6$(NR$_2$R$_6$) or —N=NR$_1$R$_6$ radical, a linear or branched alkyl radical comprising from 1 to 20 carbon atoms, a linear or branched alkenyl radical comprising from 1 to 20 carbon atoms, a cycloalkyl radical comprising from 3 to 7 carbon atoms, an aryl, aryloxy, heteroaryl, heteroaryloxy, arylalkyl, arylalkyloxy, heteroarylalkyl, heteroarylalkyloxy, arylcarbonyl, heteroarylcarbonyl, arylcarbonyloxy or heteroarylcarbonyloxy radical, the hydroxyl radical and the cyano radical;

R$_1$, R$_2$, R$_3$, R$_4$, R$_5$ and R$_6$ are as defined in claim 1, and Z is the divalent radical =CWW', for which W is a halogen atom or the R$_1$ radical and W' is a halogen atom or a radical selected from the group consisting of R$_2$, OR$_2$, SR$_2$ or NR$_1$R$_6$ radicals, all as defined in claim 1, (i) by reaction of a compound of formula (IIa):

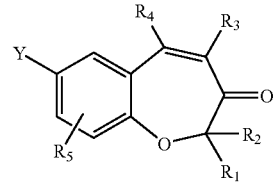

(IIa)

in which Y, R$_1$, R$_2$, R$_3$, R$_4$, R$_5$ and R$_6$ are as defined above,
with a Wittig reagent of formula (XIII):

(Ph)$_3$P$^+$—CHW(W')X''$^-$    (XIII)

in which W is a halogen atom or the R$_1$ radical and W' is a halogen atom or a radical selected from the group consisting of R$_2$, OR$_2$, SR$_2$ or NR$_1$R$_6$ radicals, and X'' is a halogen counterion, by the action of one or more equivalents of a base in an aprotic solvent at a temperature ranging from −78° C. to 50° C.;

(ii) starting from a compound of formula (IIa) in which Y, R$_1$, R$_2$, R$_3$, R$_4$, R$_5$ and R$_6$ are as defined above, prepared by elimination of a sulfinate group from a compound of formula (IIIa):

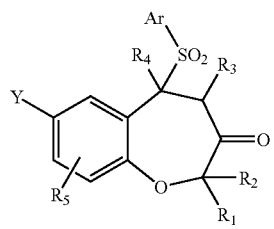
(IIIa)

in which Y, $R_1$, $R_2$, $R_3$, $R_4$, $R_5$ and $R_6$ are as defined above and Ar is a phenyl or toluyl radical, by the action of one or more equivalents of a base, optionally supported on a resin, in a solvent, over a time ranging from 0.1 to 48 h, at a temperature of between −80° C. and 180° C., optionally in the presence of a catalytic amount of an acid;

(iii) starting from a compound (IIIa) in which Y, $R_1$, $R_2$, $R_3$, $R_4$, $R_5$ and $R_6$ are as defined above and Ar is a phenyl or toluyl radical, prepared by oxidation of a compound of formula (IVa):

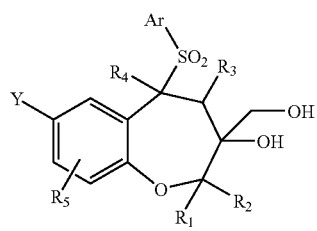
(IVa)

in which Y, $R_1$, $R_2$, $R_3$, $R_4$, $R_5$ and $R_6$ are as defined above and Ar is a phenyl or toluyl radical, by the action of one or more equivalents of an oxidizing agent, in an aromatic hydrocarbon, a halogenated hydrocarbon, an ester, a nitrile, a nitrogenous solvent, or a protic solvent, over a reaction time ranging from 0.1 to 48 h and at a temperature of between −80° C. and 180° C., optionally in the presence of a catalytic amount of an acid;

(iv) starting from a compound of general formula (IVa) in which Y, $R_1$, $R_2$, $R_3$, $R_4$, $R_5$ and $R_6$ are as defined above and Ar is a phenyl or toluyl radical, prepared by oxidation of a compound of formula (Va):

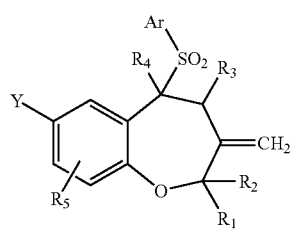
(Va)

in which Y, $R_1$, $R_2$, $R_3$, $R_4$, $R_5$ and $R_6$ are as defined above and Ar is a phenyl or toluyl radical, by the action of a catalytic amount of one or more equivalents of an oxidizing agent, in an aromatic or aliphatic hydrocarbon, a halogenated hydrocarbon, an ether, a ketone, an ester, a nitrile, a nitrogenous solvent, or a protic solvent, over a time ranging from 0.1 to 48 h and at a temperature ranging from −80° C. to 180° C., optionally in the presence of one or more equivalents of a cooxidant;

(v) starting from a compound of general formula (Va) in which Y, $R_1$, $R_2$, $R_3$, $R_4$, $R_5$ and $R_6$ are as defined above and Ar is a phenyl or toluyl radical, prepared by cyclization of a compound of formula (VIa):

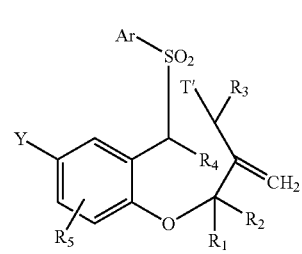
(VIa)

in which Y, $R_1$, $R_2$, $R_3$, $R_4$, $R_5$ and $R_6$ are as defined above, Ar is a phenyl or toluyl radical and T' is a halogen atom or a sulfonate, by the action of one or more equivalents of a base optionally supported on a resin, in the presence of a catalytic amount or of one or more equivalents of hexamethylphosphoramide or of dimethylpropyleneurea, in an ether, over a reaction time ranging from 0.1 to 48 h and at a temperature of between −80° C. and 180° C.;

(vi) starting from a compound of general formula (VIa) in which Y, $R_1$, $R_2$, $R_3$, $R_4$, $R_5$ and $R_6$ are as defined above, Ar is a phenyl or toluyl radical and T' is a halogen atom or a sulfonate, by condensation of a compound of formula (VII):

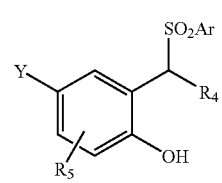
(VII)

in which Y, $R_4$, $R_5$ and $R_6$ are as defined above and Ar is a phenyl or toluyl radical, with a compound of formula (VIIIa):

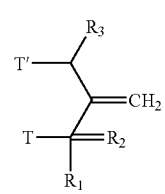
(VIIIa)

in which $R_1$, $R_2$ and $R_3$ are as defined above and T and T' are, independently of one another, a halogen atom or a sulfonate, by the action of one or more equivalents of a base, optionally supported on a resin, optionally in the presence of a catalytic amount of iodide salt, in an ether, a ketone, a nitrile, a dipolar aprotic solvent, or a protic solvent, over a reaction time ranging from 0.1 to 48 h and at a temperature ranging from −80° C. to 180° C.

8. The process for the preparation of a compound of formula (Ia) as claimed in claim 7, starting from the compound of formula (IIa) by reaction with a Wittig-Homer reagent of formula (XIV):

(EtO)$_2$P(O)CHWW'  (XIV)

in which W is the R$_1$ radical and W' is a radical selected from the group consisting of cyano, C(O)R$_2$ or C(O)OR$_2$ radicals, by the action of one or more equivalents of a base, or of an organometallic derivative, in an aprotic solvent, at a temperature ranging from −78° C. to 50° C.

9. The process for the preparation of a compound of general formula (IIIa) as claimed in claim 7, by oxidation of a compound of formula (Va) by the action of one or more equivalents of an oxidizing agent, optionally in the presence of dimethyl sulfide or of trimethylphosphine, in a halogenated hydrocarbon, a ketone, a nitrogenous solvent, or a protic solvent, over a reaction time ranging from 0.1 to 48 h and at a temperature ranging from −80° C. to 180° C.

10. The process of a preparation of a compound of general formula (IIa) as claimed in claim 7, starting from a compound of formula (Va) by the action of one or more equivalents of an oxidizing agent, followed by the action of a base.

11. A process for the preparation of a compound of formula (Ib) in which Y is selected from the group consisting of hydrogen, a halogen atom selected from the group consisting of fluorine, chlorine, bromine and iodine, the formyl radical, the carboxyl radical, an alkoxy radical, the linear or branched alkyl part comprising from 1 to 6 carbon atoms, a cycloalkoxy radical, the cycloalkyl part comprising from 3 to 7 carbon atoms, a hydroxyalkyl radical, the linear or branched alkyl part comprising from 1 to 6 carbon atoms, the nitro radical, an alkylcarbonyl radical, the linear or branched alkyl part comprising from 1 to 6 carbon atoms, a cycloalkylcarbonyl radical, the cycloalkyl part comprising from 3 to 7 carbon atoms, an alkoxycarbonyl radical, the linear or branched alkyl part comprising from 1 to 6 carbon atoms, a cycloalkoxycarbonyl radical, the cycloalkyl part comprising from 3 to 7 carbon atoms, a heterocycyloxycarbonyl radical, an alkylcarbonyloxy radical, the linear or branched alkyl part comprising from 1 to 6 carbon atoms, a cycloalkylcarbonyloxy radical, the cycloalkyl part comprising from 3 to 7 carbon atoms, an —SR$_1$, —SOR$_1$, —SO$_2$R$_1$, —C(O)NR$_1$R$_6$, —C(O)NR$_1$(OR$_2$), —C(O)NR$_1$(NR$_2$R$_6$), —C(S)NR$_1$R$_6$, —NR$_1$C(O)NR$_2$R$_6$, —NR$_1$C(S)NR$_2$R$_6$, —OC(O)NR$_1$R$_6$, —NR$_1$R$_6$, —NR$_1$(OR$_2$), —C(R$_1$)=NR$_6$, —C(R$_1$)=NR$_6$(OR$_2$), —C(R$_1$)=NR$_6$(NR$_2$R$_6$) or —N=NR$_1$R$_6$ radical, a linear or branched alkyl radical comprising from 1 to 20 carbon atoms, a linear or branched alkenyl radical comprising from 1 to 20 carbon atoms, a cycloalkyl radical comprising from 3 to 7 carbon atoms, an aryl, aryloxy, heteroaryl, heteroaryloxy, arylalkyl, arylalkyloxy, heteroarylalkyl, heteroarylalkyloxy, arylcarbonyl, heteroarylcarbonyl, arylcarbonyloxy or heteroarylcarbonyloxy radical, the hydroxyl radical and the cyano radical;

R$_1$, R$_2$, R$_3$, R$_3$', R$_4$, R$_5$ and R$_6$ are as defined in claim 1, R$_4$' is the hydrogen atom and Z is the divalent radical =CWW', for which W is a halogen atom or the R$_1$ radical and W' is a halogen atom or a radical selected from the group consisting of R$_2$, OR$_2$, SR$_2$ or NR$_1$R$_6$ radicals as defined in claim 1, (i) by reaction of a compound of formula (IIb):

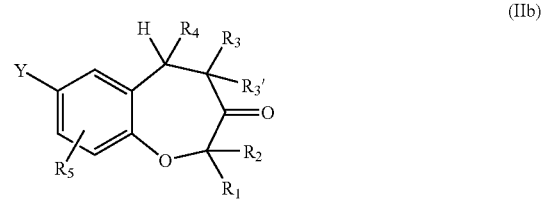

(IIb)

in which Y, R$_1$, R$_2$, R$_3$, R$_3$', R$_4$, R$_5$ and R$_6$ are as defined above, with a Wittig reagent of formula (XIII):

(Ph)$_3$P$^+$—CHW(W')X''$^-$  (XIII)

in which W is a halogen atom or the R$_1$ radical and W' is a halogen atom or a radical selected from the group consisting of R$_2$, OR$_2$, SR$_2$ or NR$_1$R$_6$ radicals, and X'' is a halogen counterion, by the action of one or more equivalents of a base, or of an organometallic derivative, in an aprotic solvent, at a temperature of −78° C. to 50° C.;

(ii) starting from a compound (IIb) in which Y, R$_1$, R$_2$, R$_3$, R$_3$', R$_4$, R$_5$ and R$_6$ are as defined above, by oxidation of a compound of formula (IXb):

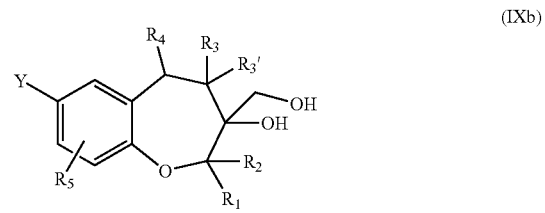

(IXb)

in which Y, R$_1$, R$_2$, R$_3$, R$_3$', R$_4$, R$_5$ and R$_6$ are as defined above, under conditions identical to the oxidation of the compound (IVa) to the compound (IIIa) as claimed in claim 7;

(iii) starting from a compound (IXb) in which Y, R$_1$, R$_2$, R$_3$, R$_3$', R$_4$, R$_5$ and R$_6$ are as defined above, by oxidation of the exocyclic double bond of a compound of formula (Xb):

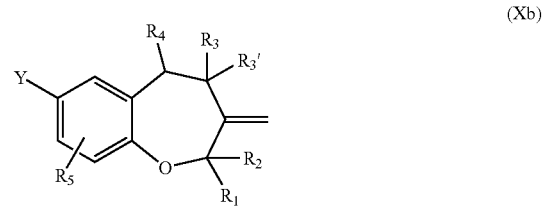

(Xb)

in which Y, R$_1$, R$_2$, R$_3$, R$_3$', R$_4$, R$_5$ and R$_6$ are as defined above, under conditions identical to the oxidation of the compound (Va) to the compound (IVa) as claimed in claim 7;

(iv) starting from a compound (Xb) in which Y, $R_1$, $R_2$, $R_3$, $R_3'$, $R_4$, $R_5$ and $R_6$ are as defined above and Ar is a phenyl or toluyl radical, by reduction of a compound of formula (Vb):

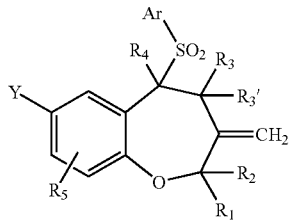
(Vb)

in which Y, $R_1$, $R_2$, $R_3$, $R_3'$, $R_4$, $R_5$ and $R_6$ are as defined above and Ar is a phenyl or toluyl radical, by the action of one or more equivalents of a reducing agent, with optional addition of one or more equivalents of mercuric chloride, trialkyltin hydrides, or samarium iodide, in a halogenated hydrocarbon, an ether, or a protic solvent, over a time ranging from 0.1 to 48 h and at a temperature ranging from −80° C. to 180° C., optionally in the presence of a catalytic amount of an acid;

(v) starting from a compound (Vb) in which Y, $R_1$, $R_2$, $R_3$, $R_3'$, $R_4$, $R_5$ and $R_6$ are as defined above and Ar is a phenyl or toluyl radical, by cyclization of a compound of formula (VIb):

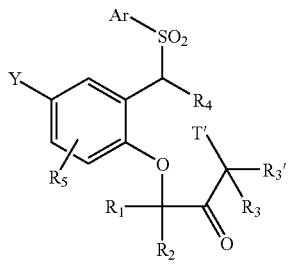
(VIb)

in which Y, $R_1$, $R_2$, $R_3$, $R_3'$, $R_4$, $R_5$ and $R_6$ are as defined above, Ar is a phenyl or toluyl radical and T' is a halogen atom or a sulfonate, by the action of one or more equivalents of a base, optionally supported on a resin, optionally in the presence of a catalytic amount or of one or more equivalents of hexamethylphosphoramide or of dimethylpropyleneurea, in an ether, over a time ranging from 0.1 to 48 h and at a temperature of between −80° C. and 180° C.;

(vi) starting from a compound (VIb) in which Y, $R_1$, $R_2$, $R_3$, $R_3'$, $R_4$, $R_5$ and $R_6$ are as defined above, Ar is a phenyl or toluyl radical and T' is a halogen atom or a sulfonate, by condensation of a compound of formula (VII), in which Y, $R_4$, $R_5$ and $R_6$ are as defined in claim 1 and Ar is a phenyl or toluyl radical, with a compound of formula (VIIIb):

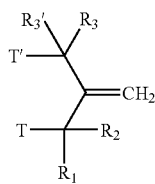
(VIIIb)

in which $R_1$, $R_2$, $R_3$ and $R_3'$ are as defined above and T and T' are, independently of one another, a halogen atom or a sulfonate, by the action of one or more equivalents of a base, optionally supported on a resin, in the presence of a catalytic or noncatalytic amount of iodide salt, in an ether, a ketone, a nitrile, a dipolar aprotic solvent, or a protic solvent, over a reaction time ranging from 0.1 to 48 h and at a temperature ranging from −80° C. to 180° C.

12. The preparation of a compound of formula (Ib) as claimed in claim 11, by reaction of a compound of formula (IIb) with a Wittig-Homer reagent of formula (XIV):

$$(EtO)_2P(O)CHWW'$$ (XIV)

in which W is the $R_1$ radical and W' is a radical selected from the group consisting of cyano, $C(O)R_2$ or $C(O)OR_2$ radicals, by the action of one or more equivalents of a base, or of an organometallic derivative, in an aprotic solvent, at a temperature of −78° C. to 50° C.

13. A process for the preparation of a compound of formula (IIa) in which Y, $R_1$, $R_2$, $R_3$, $R_4$, $R_5$ and $R_6$ are as defined in claim 1 and Ar is a phenyl or toluyl radical, by oxidation of a compound of formula (Xb) in which Y, $R_1$, $R_2$, $R_3$, $R_4$, $R_5$ and $R_6$ are as defined in claim 1 and Ar is a phenyl or toluyl radical, by the action of one or more equivalents of an oxidizing agent and under conditions identical to the oxidation of the compound (Va) to the compound (IIIa) as claimed in claim 7.

14. A process for the preparation of a compound of formula (Ia) in which Y, $R_1$, $R_2$, $R_3$, $R_4$, $R_5$ and $R_6$ are as defined in claim 1 and Z is the divalent radical =CWW', for which W is a halogen atom or the $R_1$ radical and W' is a halogen atom or a radical selected from the group consisting of $R_2$, $OR_2$, $SR_2$, $NR_1R_6$, cyano, $C(O)R_2$ or $C(O)OR_2$ radicals, the exocyclic double bond being of E stereochemistry, by isomerization of a compound (Ia) in which Y, $R_1$, $R_2$, $R_3$, $R_4$, $R_5$ and $R_6$ are as defined above and Z is a divalent radical =CWW', for which W is a halogen atom or the $R_1$ radical and W' is a halogen atom or a radical selected from the group consisting of $R_2$, $OR_2$, $SR_2$, $NR_1R_6$, cyano, $C(O)R_2$ or $C(O)OR_2$ radicals, the exocyclic double bond being of Z stereochemistry, by heating, in a solvent and under ultraviolet radiation, optionally in the presence of a catalyst, at a temperature ranging from 0° C. to the boiling point of the solvent, which is an aliphatic hydrocarbon, an aromatic hydrocarbon, an ether, a halogenated hydrocarbon, an ester, a nitrile, an alcohol, a dipolar aprotic solvent, or water.

15. A process of the preparation of a compound of formula (Ib) in which Y, $R_1$, $R_2$, $R_3$, $R_3'$, $R_4$, $R_4'$, $R_5$ and $R_6$ are as defined in claim 1 and Z is the divalent radical =CWW', for which W is a halogen atom or the $R_1$ radical and W' is a halogen atom or a radical selected from the group consisting of $R_2$, $OR_2$, $SR_2$, $NR_1R_6$, cyano, $C(O)R_2$ or $C(O)OR_2$ radicals, the exocyclic double bond being of E stereochemistry, by isomerization of the compound of general formula (Ib) in which Y, $R_1$, $R_2$, $R_3$, $R_3^1$, $R_4$, $R_4'$, $R_5$ and $R_6$ are as defined in the general formula and Z is the divalent radical =CWW', for which W is a halogen atom or the $R_1$ radical and W' is a halogen atom or a radical selected from the group consisting of $R_2$, $OR_2$, $SR_2$, $NR_1R_6$, cyano, $C(O)R_2$ or $C(O)OR_2$ radicals, the exocyclic double bond being of Z stereochemistry, by heating, in a solvent and under ultraviolet radiation, optionally in the presence of a catalyst, in an aliphatic hydrocarbon, an aromatic hydrocarbon, an ether, a halogenated hydrocarbon, an ester, a nitrile, an alcohol, a dipolar aprotic solvent, or water.

16. A process for the preparation of a compound of formula (Ia) in which $R_1$, $R_2$, $R_3$, $R_4$, $R_5$ and $R_6$ are as defined in claim 1, Z is the divalent radical =CWW', for which W is a halogen atom or the $R_1$ radical and W' is a halogen atom or a radical selected from the group consisting of $R_2$, $OR_2$, $SR_2$ or $NR_1R_6$ radicals, and Y is the alkylcarbonyl, arylcarbonyl or heteroarylcarbonyl radical, by regioselective reaction of a compound of formula (IIa) defined in claim 7, in which $R_1$, $R_2$, $R_3$, $R_4$, $R_5$ and $R_6$ are as defined above and Y is the alkylcarbonyl, arylcarbonyl or heteroarylcarbonyl radical, with a Wittig reagent of formula (XIII), in which W is a halogen atom or the $R_1$ radical and W' is a halogen atom or a radical selected from the group consisting of $R_2$, $OR_2$, $SR_2$ or $NR_1R_6$ radicals, and X" is a halogen counterion, under conditions identical to those of claim 7.

17. A process for the preparation of a compound of formula (Ia) in which $R_1$, $R_2$, $R_3$, $R_4$, $R_5$ and $R_6$ are as defined in claim 1, Z is the divalent radical =CWW', for which W is the $R_1$ radical and W' is a radical selected from the group consisting of cyano, $C(O)R_2$ or $C(O)OR_2$ radicals, and Y is the alkylcarbonyl, arylcarbonyl or heteroarylcarbonyl radical, by regioselective reaction of a compound of formula (IIa), in which $R_1$, $R_2$, $R_3$, $R_4$, $R_5$ and $R_6$ are as defined in claim 1 and Y is the alkylcarbonyl, arylcarbonyl or heteroarylcarbonyl radical, with a Wittig-Horner reagent of formula (XIV), in which W is a $R_1$ radical and W' is a radical selected from the group consisting of cyano, $C(O)R_2$ or $C(O)OR_2$ radicals, under conditions identical to those of claim 7.

18. A process for the preparation of a compound of formula (Ib) in which $R_1$, $R_2$, $R_3$, $R_3'$, $R_4$, $R_4'$, $R_5$ and $R_6$ are as defined in claim 1, Z is the divalent radical =CWW', for which W is a halogen atom or the $R_1$ radical and W' is a halogen atom or a radical selected from the group consisting of $R_2$, $OR_2$, $SR_2$ or $NR_1R_6$ radicals, and Y is the alkylcarbonyl, arylcarbonyl or heteroarylcarbonyl radical, by regioselective reaction of a compound of formula (IIb), in which $R_1$, $R_2$, $R_3$, $R_3'$, $R_4$, $R_4'$, $R_5$ and $R_6$ are as defined above and Y is the alkylcarbonyl, arylcarbonyl or heteroarylcarbonyl radical, with a Wittig reagent of formula (XIII), in which W is a halogen atom or the $R_1$ radical and W' is a halogen atom or a radical selected from the group consisting of $R_2$, $OR_2$, $SR_2$ or $NR_1R_6$ radicals, and X" is a halogen counterion, under conditions identical to those of claim 11.

19. A process for the preparation of a compound of formula (Ib) in which $R_1$, $R_2$, $R_3$, $R_3'$, $R_4$, $R_4'$, $R_5$ and $R_6$ are as defined in claim 1, Z is the divalent radical =CWW', for which W is the $R_1$ radical and W' is a radical selected from the group consisting of cyano, $C(O)R_2$ or $C(O)OR_2$ radicals, and Y is the alkylcarbonyl, arylcarbonyl or heteroarylcarbonyl radical, by regioselective reaction of a compound of formula (IIb), in which $R_1$, $R_2$, $R_3$, $R_3'$, $R_4$, $R_4'$, $R_5$ and $R_6$ are as defined above and Y is the alkylcarbonyl, arylcarbonyl or heteroarylcarbonyl radical, with a Wittig-Horner reagent of formula (XIV), in which W is the $R_1$ radical and W' is a radical selected from the group consisting of cyano, $C(O)R_2$ or $C(O)OR_2$ radicals, under conditions identical to those of claim 11.

20. A process for the preparation of a compound of formula (IIa) in which Y, $R_1$, $R_2$, $R_3$, $R_4$, $R_5$ and $R_6$ are as defined in claim 1, (i) by oxidation of a compound of formula (IXa):

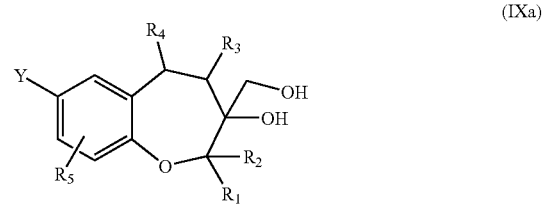

(IXa)

in which Y, $R_1$, $R_2$, $R_3$, $R_4$, $R_5$ and $R_6$ are as defined above, under conditions identical to those of the oxidation of the compound (IVa) to the compound (IIIa) of claim 7;

(ii) starting from a compound of formula (IXa) in which Y, $R_1$, $R_2$, $R_3$, $R_4$, $R_5$ and $R_6$ are as defined above, prepared by oxidation of the exocyclic double bond of a compound of formula (Xa):

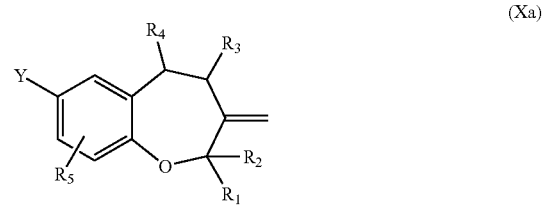

(Xa)

in which Y, $R_1$, $R_2$, $R_3$, $R_4$, $R_5$ and $R_6$ are as defined above, under conditions identical to those of the oxidation of the compound (Va) to the compound (IVa) of claim 7;

(iii) starting from a compound of formula (Xa) in which Y, $R_1$, $R_2$, $R_3$, $R_4$, $R_5$ and $R_6$ are as defined above, prepared by cyclization of a compound of formula (XIa):

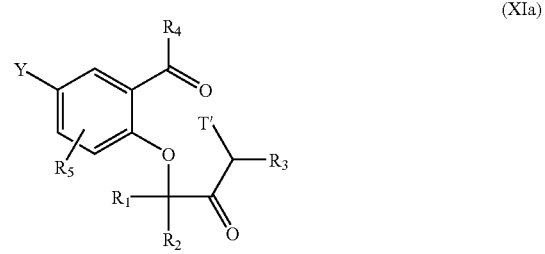

(XIa)

in which Y, $R_1$, $R_2$, $R_3$, $R_4$, $R_5$ and $R_6$ are as defined above, by the successive action of one or more equivalents of triphenylphosphine at reflux of the solvent and then addition of one or more equivalents of a base, or of an organometallic derivative, in an ether, a nitrile, or a dipolar aprotic solvent, over a time ranging from 0.1 to 48 h and at a temperature ranging from −80° C. to 180° C.;

(iv) starting from a compound of formula (XIa) in which Y, $R_1$, $R_2$, $R_3$, $R_4$, $R_5$ and $R_6$ are as defined above, prepared by condensation of a compound of formula (XIIa):

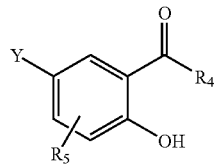

(XIIa)

in which Y, $R_4$, $R_5$ and $R_6$ are as defined above,
with a compound of formula (VIIIa) as defined in claim 7, in which $R_1$, $R_2$ and $R_3$ are as defined above and T and T' are, independently of one another, a halogen atom,
by the action of one or more equivalents of a base under conditions identical to those of the condensation of the compound (VII) with the compound (VIIIa) of claim 7.

21. A process for the preparation of a compound of formula (IIa) in which Y, $R_1$, $R_2$, $R_3$, $R_4$, $R_5$ and $R_6$ are as defined in claim 1, by ozonolyis of the exocyclic double bond of a compound of formula (Xa) in which Y, $R_1$, $R_2$, $R_3$, $R_4$, $R_5$ and $R_6$ are as defined above, under conditions identical to those of the ozonolysis of the compound (Va) to the compound (IIIa) of claim 7.

22. A process for the preparation of a compound of formula (IIIa) in which Y, $R_1$, $R_2$, $R_3$, $R_5$ and $R_6$ are as defined in claim 1, Ar is a phenyl or toluyl radical and $R_4$ is selected from the group consisting of alkyl, arylalkyl or heteroarylalkyl radicals, by alkylation of a compound of formula (IIIa), in which Y, $R_1$, $R_2$, $R_3$, $R_5$ and $R_6$ are as defined above, Ar is a phenyl or toluyl radical and $R_4$ is a hydrogen atom,
with an alkyl halide, respectively arylalkyl halide or heteroarylalkyl halide,
by the action of one or several equivalents of an organic or inorganic base, optionally supported on a resin, in the presence of a catalytic amount or of one or several equivalents of hexamethylphosphoramide or of dimethylpropyleneurea, at a temperature ranging from −80° C. to 180° C., in an aliphatic hydrocarbon, an aromatic hydrocarbon, halobenzenes, an ether, a halogenated hydrocarbon, an ester, a nitrile, a dipolar aprotic solvent, or water, over a time ranging from 0.1 to 48 h.

23. A process for the preparation of a compound of formula (IIIb) in which Y, $R_1$, $R_2$, $R_3$, $R_3'$, $R_5$ and $R_6$ are as defined in claim 1, Ar is a phenyl or toluyl radical and $R_4$ is selected from the group consisting of alkyl, arylalkyl or heteroarylalkyl radicals, by alkylation of a compound of formula (IIIb), in which Y, $R_1$, $R_2$, $R_3$, $R_3'$, $R_5$ and $R_6$ are as defined above, Ar is a phenyl or toluyl radical and $R_4$ is a hydrogen atom, with an alkyl halide, respectively arylalkyl halide or heteroarylalkyl halide, by the action of one or several equivalents of an organic or inorganic base, optionally supported on a resin, in the presence of a catalytic amount or of one or several equivalents of hexamethylphosphoramide or of dimethylpropyleneurea, at a temperature ranging from −80° C. to 180° C., in an aliphatic hydrocarbon, an aromatic hydrocarbon, halobenzenes, an ether, a halogenated hydrocarbon, an ester, a nitrile, a dipolar aprotic solvent, or water, over a time ranging from 0.1 to 48 h.

24. A process for the preparation of a compound of formula (Va) in which Y, $R_1$, $R_2$, $R_3$, $R_5$ and $R_6$ are as defined in claim 1, Ar is a phenyl or toluyl radical and $R_4$ is selected from the group consisting of alkyl, arylalkyl or heteroarylalkyl radicals, by alkylation of a compound of formula (Va), in which Y, $R_1$, $R_2$, $R_3$, $R_5$ and $R_6$ are as defined above, Ar is a phenyl or toluyl radical and $R_4$ is a hydrogen atom,
with an alkyl halide, respectively arylalkyl halide or heteroarylalkyl halide,
by the action of one or several equivalents of an organic or inorganic base, optionally supported on a resin, in the presence of a catalytic amount or of one or several equivalents of hexamethylphosphoramide or of dimethylpropyleneurea, at a temperature ranging from −80° C. to 180° C., in an aliphatic hydrocarbon, an aromatic hydrocarbon, halobenzenes, an ether, a halogenated hydrocarbon, an ester, a nitrile, a dipolar aprotic solvent, or water, over a time ranging from 0.1 to 48 h.

25. A process for the preparation of a compound of formula (Vb) in which Y, $R_1$, $R_2$, $R_3$, $R_3'$, $R_5$ and $R_6$ are as defined in claim 1, Ar is a phenyl or toluyl radical and $R_4$ is selected from the group consisting of alkyl, arylalkyl or heteroarylalkyl radicals, by alkylation of a compound of formula (Vb), in which Y, $R_1$, $R_2$, $R_3$, $R_5$ and $R_6$ are as defined above, Ar is a phenyl or toluyl radical and $R_4$ is a hydrogen atom,
with an alkyl halide, respectively arylalkyl halide or heteroarylalkyl halide,
by the action of one or several equivalents of an organic or inorganic base, optionally supported on a resin, in the presence of a catalytic amount or of one or several equivalents of hexamethylphosphoramide or of dimethylpropyleneurea, at a temperature ranging from −80° C. to 180° C., in an aliphatic hydrocarbon, an aromatic hydrocarbon, halobenzenes, an ether, a halogenated hydrocarbon, an ester, a nitrile, a dipolar aprotic solvent, or water, over a time ranging from 0.1 to 48 h.

26. The compound as claimed in claim 1 for which $R_2$ represents the hydrogen atom.

* * * * *